(12) United States Patent
Imbimbo

(10) Patent No.: US 12,378,293 B2
(45) Date of Patent: Aug. 5, 2025

(54) PRODUCTION OF NERVE GROWTH FACTOR (NGF) AND OF MUTEINS THEREOF

(71) Applicant: Chiesi Farmaceutici SpA, Parma (IT)

(72) Inventor: Bruno Pietro Imbimbo, Parma (IT)

(73) Assignee: Chiesi Farmaceutici SpA, Parma (IT)

( * ) Notice: Subject to any disclaimer, the term of this patent is extended or adjusted under 35 U.S.C. 154(b) by 1029 days.

(21) Appl. No.: 17/050,252

(22) PCT Filed: Apr. 26, 2019

(86) PCT No.: PCT/EP2019/060733
§ 371 (c)(1),
(2) Date: Oct. 23, 2020

(87) PCT Pub. No.: WO2019/207106
PCT Pub. Date: Oct. 31, 2019

(65) Prior Publication Data
US 2021/0079053 A1     Mar. 18, 2021

(30) Foreign Application Priority Data

Apr. 27, 2018   (EP) .................................. 18169859

(51) Int. Cl.
| C07K 14/48 | (2006.01) |
| C07K 1/16  | (2006.01) |
| C12N 9/76  | (2006.01) |
| A61K 38/00 | (2006.01) |

(52) U.S. Cl.
CPC ............. *C07K 14/48* (2013.01); *C07K 1/165* (2013.01); *C12N 9/6427* (2013.01); *A61K 38/00* (2013.01)

(58) Field of Classification Search
None
See application file for complete search history.

(56) References Cited

U.S. PATENT DOCUMENTS

| 7,205,387 B2 * | 4/2007 | Wang .................... C07K 16/40 530/300 |
| 2018/0086805 A1 * | 3/2018 | Cattaneo ................. C12P 21/06 |

FOREIGN PATENT DOCUMENTS

| CN | 108314723 A * | 7/2018 |
| WO | WO 1998/021234 A2 | 5/1998 |
| WO | WO-0022119 A1 | 4/2000 |
| WO | WO-2008006893 A1 | 1/2008 |
| WO | WO 2013/092776 A1 | 6/2013 |
| WO | WO 2019/207106 A1 | 10/2019 |

OTHER PUBLICATIONS

Capsoni, et al., PLoS One, 7(5):1-16 (2012) (Year: 2012).*
Chevalier, S., et al., "Expression and functionality of the trkA proto-oncogene product/NGF receptor in undifferentiated hematopoietic cells," *Blood* 83(6):1479-1485, American Society of Hematology, United States (Mar. 1994).
D'Onofrio, A., et al., "NGF and proNGF Regulate Functionally Distinct mRNAs in PC12 Cells: An Early Gene Expression Profiling," *PLoS One* 6(6):e20839, Public Library of Science, United States (Jun. 2011), 13 pages.
Della Seta, D., et al., "NGF Effects on Hot Plate Behaviors in Mice," *Pharmacology Biochemistry and Behavior* 49(3):701-705, Elsevier, United States (Nov. 1994).
Dyck, P. J., et al., "Intradermal Recombinant Human Nerve Growth Factor Induces Pressure Allodynia and Lowered Heat-Pain Threshold in Humans," *Neurology* 48(2):501-505, Lippincott Williams & Wilkins, United States (Feb. 1997).
Einarsdottir, E., et al., "A mutation in the nerve growth factor beta gene (NGFB) causes loss of pain perception," *Human Molecular Genetics* 13(8):799-805, Oxford University Press, United Kingdom (published online Feb. 2004, published in print Apr. 2004).
Eng, M., et al., "Formulation development and primary degradation pathways for recombinant human nerve growth factor," *Analytical Chemistry* 69(20):4184-4190, American Chemical Society, United States (Oct. 1997).
Hao, J., et al., "Intracerebroventricular infusion of nerve growth factor induces pain-like response in rats," *Neuroscience Letters* 286(3):208-212, Elsevier, Netherlands (Jun. 2000).
Kurokawa, Y., et al., "Overproduction of bacterial protein disulfide isomerase (DsbC) and its modulator (DsbD) markedly enhances periplasmic production of human nerve growth factor in *Escherichia coli*," *J Biol Chem* 276(17):14393-14399, Elsevier, Netherlands (published online Jan. 2001, published in print Apr. 2001).
Larsson, E., et al., "Nerve growth factor R221W responsible for insensitivity to pain is defectively processed and accumulates as proNGF," *Neurobiology of Disease* 33(2):221-228, Elsevier, Netherlands (published online Nov. 2008, published in print Feb. 2009).
Levi-Montalcini, R., "The Nerve Growth Factor and the Neuroscience Chess Board," *Progress in Brain Research* 146:525-527, Elsevier, Netherlands (Jan. 2004).
Lewin, G. R., et al., "Peripheral and Central Mechanisms of NGF-Induced Hyperalgesia," *The European Journal of Neuroscience* 6(12):1903-1912, Wiley-Blackwell, France (Dec. 1994).
Mai, M., et al., "Outcome Prediction in Mathematical Models of Immune Response to Infection," *PLoS One* 10(8):e0135861, Public Library of Science, United States (Aug. 2015), 15 pages.

(Continued)

Primary Examiner — David W Berke-Schlessel
(74) Attorney, Agent, or Firm — Element IP, PLC

(57) ABSTRACT

The present invention relates to a process for production of nerve growth factor (NGF) and muteins thereof, in particular muteins of human NGF. The process of the present invention yields nerve growth factor (NGF) and muteins thereof, e.g. from recombinant sources, at high purity. Aspects related to the process of the present invention, such as muteins obtainable thereby, are also described. The respective muteins may be characterized e.g. by improved detectability and/or reduced nociceptive activity, compared to wildtype human NGF.

8 Claims, 22 Drawing Sheets
Specification includes a Sequence Listing.

(56) References Cited

OTHER PUBLICATIONS

Malerba, F., et al., "Functional Characterization of Human ProNGF and NGF Mutants: Identification of NGF P61SR100E as a "Painless" Lead Investigational Candidate for Therapeutic Applications," *PLoS One 10*(9):e0136425, Public Library of Science, United States (Sep. 2015), 34 pages.

McArthur, J. C., et al., "A Phase II Trial of Nerve Growth Factor for Sensory Neuropathy Associated with HIV Infection." *Neurology 54*(5):1080-1088, Lippincott Williams & Wilkins, United States (Mar. 2000).

Pearson, W. R., "An introduction to sequence similarity ("homology") searching," *Current Protocols in Bioinformatics 42*(Chapter 3):3.1.1-3.1.8, John Wiley & Sons, Inc., United States (Jun. 2013).

Rattenholl, A., et al., "The Pro-Sequence Facilitates Folding of Human Nerve Growth Factor From *Escherichia coli* Inclusion Bodies," *European Journal of Biochemistry 268*(11):3296-3303, Springer, United Kingdom (Jun. 2001).

Rattenholl, A., "Untersuchungen zur Pro-Sequenz-vermittelten Faltung von rekombinantem, humanen Nervenwachstumsfaktor," Dissertation to Obtain the Academic Degree Doctor Rerum Naturalium (Dr. rer. Nat.), submitted to the Mathematical, Natural-Scientific, Technical Faculty of the Martin-Luther-Universität Halle-Wittenberg, Germany (Jun. 2001).

Reichardt, L. F., "Neurotrophin-regulated signalling pathways," *Philosophical Transactions of the Royal Society B: Biological Sciences 361*(1473):1545-1564, The Royal Society Publishing, United Kingdom (published online Aug. 2006).

Ruiz, G., et al., "Behavioral and histological effects of endoneurial administration of nerve growth factor: possible implications in neuropathic pain," *Brain Research 1011*(1):1-6, Elsevier, Netherlands (published online Apr. 2004).

Schenck, K., et al., "The Role of Nerve Growth Factor (NGF) and Its Precursor Forms in Oral Wound Healing," *International Journal of Molecular Sciences 18*(2):386, Multidisciplinary Digital Publishing Institute, Switzerland (Feb. 2017), 12 pages.

Svensson, P., et al., "Injection of nerve growth factor into human masseter muscle evokes long-lasting mechanical allodynia and hyperalgesia," *Pain 104*(1-2):241-247, Lippincott Williams & Wilkins, United States (Jul. 2003).

UniProtKB, "UniProtKB—P01138 (NGF_Human)," Accession No. P01138, accessed at https://www.uniprot.org/uniprot/P01138, accessed on Jun. 24, 2021, 10 pages.

Wiesmann, C., et al., "Crystal Structure of Nerve Growth Factor in Complex with the Ligand-Binding Domain of the TrkA Receptor," *Nature 401*(6749):184-188, Nature Publishing Group, United Kingdom (Sep. 1999).

Yang, Z., et al., "Highly Efficient Production of Soluble Proteins from Insoluble Inclusion Bodies by a Two-Step-Denaturing and Refolding Method," *PLoS One 6*(7):e22981, Public Library of Science, United States (Jul. 2011), 8 pages.

European Patent Office, International Search Report in International Application No. PCT/EP2019/060733 (Jun. 21, 2019).

European Patent Office, Written Opinion of The International Searching Authority in International Application No. PCT/EP2019/060733 (Jun. 21, 2019).

* cited by examiner

Fig. 5B

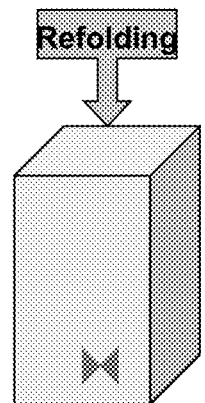

Refolding

Refolding via pulsed dilution at 4°C (overnight)
Refolding buffer: 1M Arg, 5mM EDTA, 0.1 M NaCl, 50mM Tris/HCl, pH 9.5
Redox system: GSSG (1mM) and GSH (5mM)
30-70 fold dilution to reach a final protein concentration of 0.4-0.6 g/L (based on total protein concentration in IB solubilizate as determined by Bradford)
Refolding pulse rate: 50-60 mg total protein / L / h; incubate the refolding reaction over night after the last addition
Scale: For refolding of IBs from one litre of fermentation culture, approx. 16 litre of Refolding reaction are required.

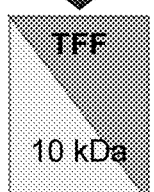

TFF 10 kDa

Ultrafiltration at 4°C: reducing of the final refolding volume
10 fold concentration; Afterwards, 5 mM $iPO_4$ are added and the pH is adjusted to 7 using 25 % HCl.
Diafiltration at 4°C: removal of Guanidine and Urea
Diabuffer: 1 M Arg, 10mM $iPO_4$ @ pH 7; 5 TOV

Dilution of diafiltered product at 4°C
For load onto the capturing column: adjusting the conductivity, by dilution with 5 mM iPO4, pH7 to 25 - 30mS/cm; Approx. 1 to 3-fold dilution required.

NOTE: Significant precipitation observed (likely caused by reduction of Arginine concentration)

Clarification

Separation of supernatant from precipitate
Centrifugation @ 15.000 x g ; 4 °C; 30'
Discard precipitate

CEX SP Sepharose FF

Capturing chromatography step at 4°C
CV: ~0.03 volumes of the load at a residence time > 15min
Binding buffer: 350mM Arg, 10mM $iPO_4$, pH 7
Elution buffer: 350mM Arg, 1M NaCl, 10mM $iPO_4$, pH 7
Step gradient: 40%B for 6 CV
Capacity: approx. 2.5 g total protein per L stationary phase
Pro-NGF mutein purity: approx. 60%
Yield: From one litre fermentation culture, approx. 400 mg pro-NGF are yielded.

Fig. 5C

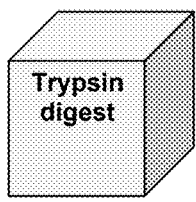

Trypsinization of pro-NGF mutein at 4°C for 6 h
Addition of 2 M $CaCl_2$ to a final concentration of 20 mM
Trypsin to pro-NGF ratio 1:150
    (corresponds to 1.6 U trypsin per mg pro-NGF mutein)
Incubate 6 hours @ 2-8°C
pro-NGF mutein to NGF mutein mass recovery: around 60%

For load onto the polishing column: adjusting the pH and conductivity by dilution with 50 mM iPO4, pH 6 to ~ 30mS/cm. Therefore, product has to be diluted approx. 3-fold. Afterwards, the pH of the product is adjusted to 6.0 using 2 M citrate.

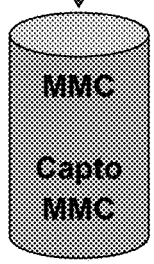

Polishing chromatography step at 4°C
Capacity: > 12 g/L
Residence time: 15 min
Binding buffer: 200mM Arg, 50mM $iPO_4$ @ pH 6, 4°C
Elution buffer: 200mM Arg, 50mM $iPO_4$ @ pH9, 4°C
Step gradient:    Wash:      25 % B
                    Elution:     100 % B
Recovery: 60-70 % (total protein)

For STIC membrane: adjusting the pH to 8.4 and conductivity by dilution with $H_2O$ to 15 mS/cm

STIC-membrane chromatography
Loading ratio: 10 mL / cm²
Flow rate: 15 membrane volumes per minute

Adjustment of the final product concentration
Target NGF concentration: 1.0 g/L
Diafiltration: against acetate buffer
Diabuffer: 50mM NaAc/HAc pH 5.5
Turn over volumes: 5
Final conductivity: ~ 3.5 mS/cm
Yield: Approx. 85 %

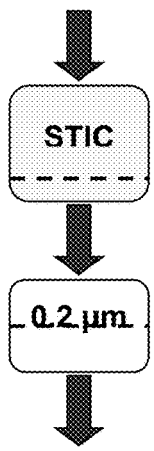

STIC-membrane chromatography
Loading ratio: 10 mL / cm²
Flow rate: 15 membrane volumes per minute

Sterile filtration
PES membrane

 Product is frozen at -70°C and should be stored at < -15 °C
Fig. 6
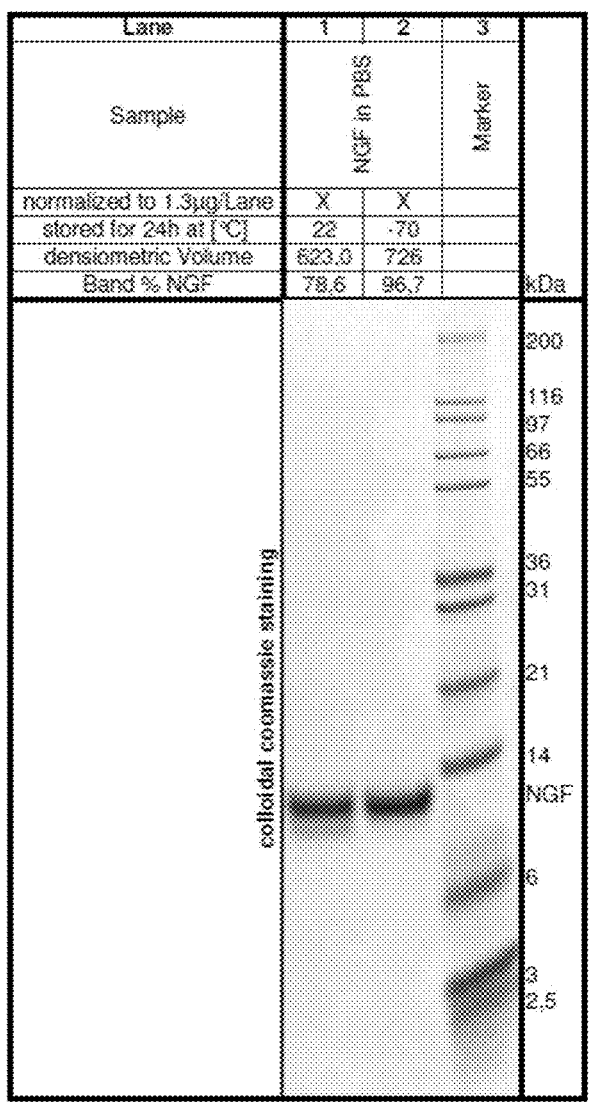

Fig. 14B

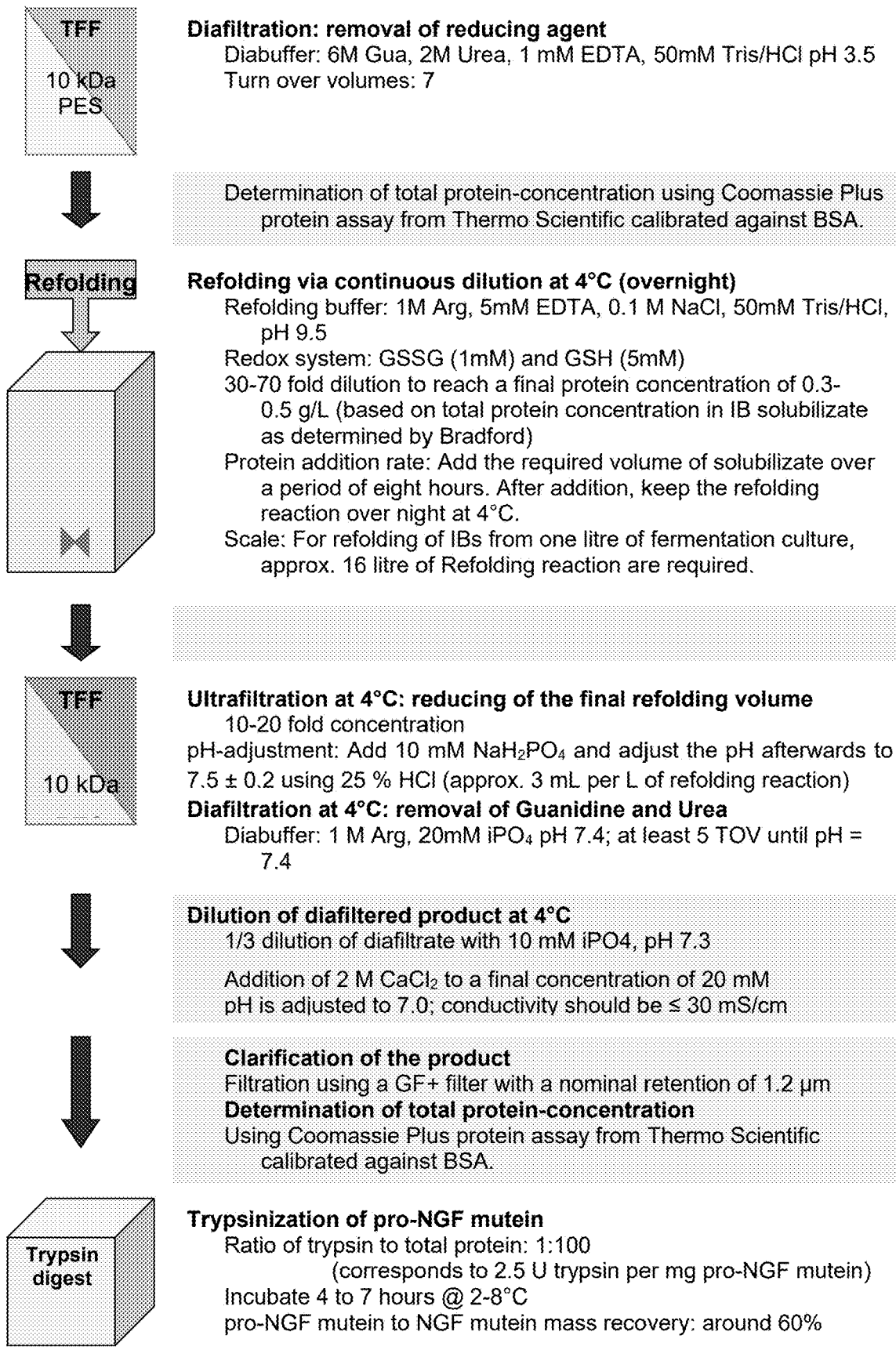

Diafiltration: removal of reducing agent
Diabuffer: 6M Gua, 2M Urea, 1 mM EDTA, 50mM Tris/HCl pH 3.5
Turn over volumes: 7

Determination of total protein-concentration using Coomassie Plus protein assay from Thermo Scientific calibrated against BSA.

Refolding via continuous dilution at 4°C (overnight)
Refolding buffer: 1M Arg, 5mM EDTA, 0.1 M NaCl, 50mM Tris/HCl, pH 9.5
Redox system: GSSG (1mM) and GSH (5mM)
30-70 fold dilution to reach a final protein concentration of 0.3-0.5 g/L (based on total protein concentration in IB solubilizate as determined by Bradford)
Protein addition rate: Add the required volume of solubilizate over a period of eight hours. After addition, keep the refolding reaction over night at 4°C.
Scale: For refolding of IBs from one litre of fermentation culture, approx. 16 litre of Refolding reaction are required.

Ultrafiltration at 4°C: reducing of the final refolding volume
10-20 fold concentration
pH-adjustment: Add 10 mM $NaH_2PO_4$ and adjust the pH afterwards to 7.5 ± 0.2 using 25 % HCl (approx. 3 mL per L of refolding reaction)
Diafiltration at 4°C: removal of Guanidine and Urea
Diabuffer: 1 M Arg, 20mM $iPO_4$ pH 7.4; at least 5 TOV until pH = 7.4

Dilution of diafiltered product at 4°C
1/3 dilution of diafiltrate with 10 mM iPO4, pH 7.3

Addition of 2 M $CaCl_2$ to a final concentration of 20 mM
pH is adjusted to 7.0; conductivity should be ≤ 30 mS/cm

Clarification of the product
Filtration using a GF+ filter with a nominal retention of 1.2 μm
Determination of total protein-concentration
Using Coomassie Plus protein assay from Thermo Scientific calibrated against BSA.

Trypsinization of pro-NGF mutein
Ratio of trypsin to total protein: 1:100
 (corresponds to 2.5 U trypsin per mg pro-NGF mutein)
Incubate 4 to 7 hours @ 2-8°C
pro-NGF mutein to NGF mutein mass recovery: around 60%

Fig. 14C

pH-adjustment & Clarification pH adjustment and removal of precipitate from solution
At the end of the incubation, carefully adjust the pH to 6.0 using 5 % HCl
The Filtration may be executed while the product is loaded onto the capturing column.

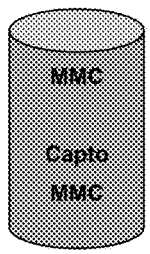

Capturing chromatography step at 4°C
Residence time: 8-15 min
Binding buffer: 350mM Arg, 20mM iPO$_4$, pH6.0 @ 4°C
Elution buffer: 350mM Arg, 50mM iPO$_4$, pH9.5 @ 4°C
Elution:     100 % B
Collect a single fraction
Yield: Approx. 10-20 mg NGF per L of refolding

Dilution of eluate from Capto MMC
For load onto the polishing column: Dilute the eluate with an equal volume of 50mM phosphoric acid to ≤ 15 mS/cm.
Afterwards, pH of the sample is carefully lowered to 6 using 5 % HCl

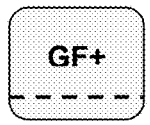
GF+

1.2 µm GF+ Filtration
Operated as on-line filter while applying the load onto the SP Sepharose HP. Before elution is started, the filter is removed.

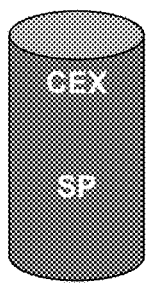

Polishing chromatography step at 4°C
Residence time: 5-10 min
Binding buffer: 50mM iPO$_4$, pH 6
Wash buffer: 50mM iPO4, 300 mM NaCl, pH 6
Elution buffer: 50mM iPO$_4$, 600 mM NaCl, pH 6
Elution Gradient: From 300 to 600 mM NaCl over 15 CV
Fractions: 0.5 CV
Pooling criteria: To be defined by the client
Yield: Approx. 4-8 mg NGF per L of refolding

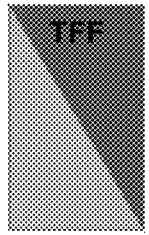
TFF

Adjustment of the final product concentration
Target NGF concentration: 0.7 ± 0.3 g/L
Diafiltration: against acetate buffer
Diabuffer: 50 mM acetate buffer, pH 5.5
Turn over volumes: 7

Desired buffer composition and NGF (mutein) concentration can be chosen

Fig. 15A

SEQ ID NO: 1

```
          10         20         30         40         50
    MSMLFYTLIT AFLIGIQAEP HSESNVPAGH TIPQAHWTKL QHSLDTALRR 60         70         80         90        100
    ARSAPAAAIA ARVAGQTRNI TVDPRLFKKR RLRSPRVLFS TQPPREAADT 110        120        130        140        150
    QDLDFEVGGA APFNRTH RSK R SSSHPIFHR GEFSVCDSVS VWVGDKTTAT

*
         160        170        180        190        200
    DIKGKEVMVL GEVNINNSVF KQYFFETKCR DPNPVDSGCR GIDSKHWNSY

+
         210        220        230        240
    CTTTHTFVKA LTMDGKQAAW RFIRIDTACV CVLSRKAVR R A
```

Fig. 15B

| Feature key | Position(s) | Length (aa) |
|---|---|---|
| pre-peptide | 1-18 | 18 |
| pro-peptide (comprising the Furin cleavage site RSKR) | 19-121 | 103 |
| beta-NGF (mature NGF) | 122-239 | 118 |
| C-terminal dipeptide | 240-241 | 2 |

Fig. 15C

SEQ ID NO: 2

```
         10         20         30         40         50
SSSHPIFHRG EFSVCDSVSV WVGDKTTATD IKGKEVMVLG EVNINNSVFK

*                                        +
         60         70         80         90        100
QYFFETKCRD PNPVDSGCRG IDSKHWNSYC TTTHTPVKAL TMDGKQAAWR 110        118
FIRIDTACVC VLSRKAVR
```

PRODUCTION OF NERVE GROWTH FACTOR (NGF) AND OF MUTEINS THEREOF

CROSS-REFERENCE TO RELATED APPLICATIONS

This application is a National Stage Entry of International Application Number PCT/EP2019/060733, which was filed on Apr. 26, 2019 and claimed priority to European Patent Application Number 18169859.8, which was filed on Apr. 27, 2018. The contents of each of the aforementioned applications are incorporated herein by reference in their entireties.

Reference to a Sequence Listing Submitted Electronically via EFS-Web

The content of the electronically submitted sequence listing (Name: SequenceListing.txt; Size: 3,808 bytes; and Date of Creation: Apr. 30, 2019), filed with the application, is incorporated herein by reference in its entirety.

INTRODUCTION

Field of the Invention

The present invention is suitable to provide nerve growth factor (NGF, also termed beta-NGF) or a mutein thereof, by an advantageous production process, in industrially relevant purity.

BACKGROUND OF THE INVENTION

Nerve growth factor (NGF) is a neurotrophin required for the development and survival of specific neuronal populations. NGF is a homodimeric peptide that naturally triggers proliferation and homeostasis of neurons. In the body, NGF binds with at least two types of receptors: the tropomyosine receptor kinase A (TrkA) and low-affinity NGF neurotrophin receptor p75 (LNGFR/p75$^{NTR}$/p75). Both are associated with certain disorders in humans and animals, although the respective mechanisms of action are likely different. Several therapeutic applications for NGF have been proposed but few have matured to the market.

However, many therapeutic uses of NGF which have been envisaged in the past have not matured to marketed therapeutic NGF products, and one reason can be seen in that NGF, besides the desired effect on proliferation and homeostasis of neurons, is associated with pain: it can, when administered topically or systemically, cause hyperalgesia (Lewin et al., 1994, Eur. J. Neurosci., vol. 6, p. 1903-1912; Della Seta et al., 1994, Pharmacol. Biochem. Behav., vol. 49, p. 701; Dyck et al, 1997, Neurology, vol. 48, 501-505; McArthur, et al., 2000, Neurology, vol. 54, p. 1080-1088; Svensson et al., 2003, Pain, vol. 104, p. 241-247; Ruiz et al., 2004, Brain Res., vol. 1011, p. 1-6). As a solution, mutant versions of NGF ("muteins") were developed, which are associated with reduced nociceptive activity ("painless NGF"), and which are characterized by at least one mutation in the domain of NGF which interacts with the TrkA receptor (WO 2008/006893 A1, Malerba et al. PLOS One, 2015, vol. 10, e0136425).

In mammalian cells, NGF is translated as a pre-proprotein in vivo. Human NGF, for example is translated as a pre-pro-protein consisting of 241 amino acids (SEQ ID NO: 1). The pre-sequence (18 amino acids) is cleaved off during translocation into the endoplasmic reticulum (ER), and the resulting proprotein is subsequently processed at its N-terminus (removal of the pro-sequence (103 amino acids) and at the C-terminus (removal of the last two amino acids, these correspond to RA at the end of SEQ ID NO: 1, bold in FIG. 15A)—for further information see e.g. WO 2000/022119 A1). Thus, mature human NGF (hNGF) is a polypeptide that consists of 118 amino acid residues; it is homologous to mature mouse NGF, in fact hNGF differs from mouse NGF only by 12 amino acid exchanges.

Painless NGF has been reported to be defectively processed (Larsson et al., Neurobiol. Dis., 2009, vol. 33, p. 221-228).

In some tissues of some species, e.g. in the mouse submaxillary gland, NGF is found in a high molecular weight complex consisting of beta-NGF and two further subunits, alpha-NGF and gamma-NGF; among these, only beta-NGF acts as neurotrophin, whereas alpha-NGF and gamma-NGF are serine proteases belonging to the kallikrein family (see e.g. Schenck et al., 2017, Int. J. Mol. Sci., vol. 18, p. 386). In the present document, unless the context dictates otherwise, the term "NGF" usually refers to the processed beta-subunit of the protein (about 26-kDa in many mammalian species), which is biologically active as a signaling molecule.

Mature and properly folded mature human NGF is characterized by three disulfide bridges (linking positions 136↔201, 179↔229, 189↔231, position numbers refer to SEQ ID NO: 1; see Wiesmann et al., 1999, Nature, vol. 401, p. 184-188).

Since human NGF is produced only in minute quantities in vivo, and mouse NGF is usually produced as a heterogeous mixture of various proteins (see WO 2000/022119 A1), the only meaningful possibility to produce NGF is by recombinant expression (WO 2000/022119 A1, WO 2008/006893 A1; Rattenholl et al., Eur. J. Biochem, 2001, vol. 268, p. 3296-3303, US 2018/0086805 A1). Furthermore, by recombinant expression, also variations of NGF characterized by one or more mutations ("muteins") could become available.

Several publications on the production of NGF or muteins thereof describe the recombinant production in bacteria (e.g. WO 2008/006893 A1; Rattenholl et al., Eur. J. Biochem, 2001, vol. 268, p. 3296-3303, WO 2013/092776 A1), although NGF produced by eukaryotic cells has also been produced and made commercially available for non-clinical use (e.g. Biosensis, Thebarton, Australia). It has, however, been reported that eukaryotic cell expression systems tend to provide very low amount of NGF protein (reviewed in WO 2000/022119 A1).

In contrast, bacterial cells, in particular *E. coli*, are capable of recombinant production of high amounts of NGF or muteins thereof, but, as is the case for many other recombinantly expressed genes, the production of recombinant NGFs or muteins thereof in bacteria results in a biologically inactive translation product which is then accumulated in the cell in the form of aggregates (so-called inclusion bodies (IBs) (WO 2000/022119 A1; US 2018/0086805 A1). In contrast to NGF, pro-NGF is known to be rather unstable and requires high efforts for refolding and purification at low recovery rates, which renders the process of NGF production via pro-NGF in bacteria relatively difficult and expensive. Thus, the main difficulties associated with bacteria-produced NGF or muteins thereof, via the respective pro-forms, concern the folding, the processing and the purification of the recombinant protein. It has also been hypothesized that the production of NGF via pro-NGF expression in prokaryotic systems may not work economically, based on the current market situation where the pro-NGF is about 20 times more expensive than NGF. According to one hypothesis, commercially available NGF may originate from periplasmic expression in bacteria, and indeed, periplasmic expression of NGF in *E. coli* has been reported in the literature (e.g. Kurokawa et al., 2001, J. Biol. Chem., vol. 276, p. 14393-14399).

Although the pro-sequence of NGF is not part of mature beta-NGF, and hence not required for its biological function, the presence of the covalently attached pro-sequence was shown to promote re-folding of recombinant NGF from inclusion bodies with concomitant disulfide bond formation of the mature part (beta-NGF). Thus, the presence of the covalently attached pro-sequence positively influences the yield and rate of re-folding when compared to the in vitro re-folding of mature NGF from inclusion bodies (Rattenholl et al., Eur. J. Biochem, 2001, vol. 268, p. 3296-3303).

Thus, when NGF or muteins thereof have been produced in inclusion bodies, correct folding is required, and this is normally achieved post-translationally, as is the cleavage from the covalently attached pro-sequence; sophisticated methods for folding, cleavage and purification have been proposed in the past, in particular for wild-type human NGF. Within scientific literature, refolding of pro-NGF is an often investigated process and this molecule often serves as model within studies investigating the formation of cysteine knots. Notably, most of published studies apply a general refolding regime which was previously established by Rattenholl et al. (2001, Eur. J. Biochem, vol. 268, p. 3296-3303). Within this original study, several parameters of protein refolding (e.g. temperature, refolding time, pH of refolding reaction, arginine, glutathione and protein concentration) were investigated in detail and the effect on the refolding efficiency was assessed. The protocol by Rattenholl et al. relies on the re-naturation of the pro-form, which has a very poor solubility, obtainable from inclusion bodies after recombinant production in prokaryotes, whereby pro-NGF is solubilized in a solution of a denaturing agent in a denaturing concentration, transferred into a solution which is not or weakly denaturing, so that the solubility is maintained and the dissolved denatured pro-NGF can assume a biologically active conformation, including formation of disulfide bonds as in native NGF, and afterwards the NGF is purified and the pro-sequence is removed proteolytically (WO 2000/022119 A1; Rattenholl et al., Eur. J. Biochem, 2001, vol. 268, p. 3296-3303). Notably, within this study it was found that a low protein concentration leads to a higher specific yield of correctly folded product as compared to a higher protein concentration. Exemplary, protein concentrations around 50 mg per liter of refolding reaction resulted in a specific yield of ~25% correctly folded pro NGF, while this fraction was reduced to 10% at protein concentrations of 500 mg per liter. Based on that, Rattenholl et al. suggest that the protein-concentration in the refolding solution has to be very low: according to Rattenholl et al., 15-20 mg of correctly folded protein per liter of refolding reaction are expected as yield. However, this would require a scale-up (e.g. beyond laboratory scale) for purification of even a few hundred mg recombinant protein.

Human pro-NGF contains a native cleavage site for the protease Furin ($Arg^1$-$Ser^2$-$Lys^3$-$Arg^4$; $R^1S^2K^3R^4$), and Furin cleaves pro-NGF at that site in vivo. However, Furin is not available at commercially relevant purity or quantity, and it has therefore been proposed to use, following expression of pro-NGF in *E. coli*, the protease Trypsin (EC 3.4.21.4), which is available commercially. Indeed, it has been initially reported that cleavage with Trypsin would yield satisfying biologically active, mature NGF, which can be eventually purified (Rattenholl et al., Eur. J. Biochem, 2001, vol. 268, p. 3296-3303), and Trypsin-based proteolysis of recombinantly expressed pro-NGF has meanwhile been adopted by others (e.g. D'Onofrio et al., 2011, PLoS One, vol. 6, e20839).

However, it was later shown that cleavage of the wild-type pro-NGF with trypsin to produce beta-NGF is associated with several drawbacks, as low amounts of trypsin would lead to inefficient cleavage, whereas high amounts of trypsin would further decrease the selectivity of the cleavage, as trypsin is capable of cleaving C-terminally of any arginine and lysine residue (R and K residue), so that by digestion of $R^1S^2K^3R^4$-containing pro-NGF by trypsin, several alternative digestion products would be obtained; thereby the use of trypsin as cleavage enzyme would lead to very low yields of correctly cleaved NGF, and to purification and yield problems, as the different cleavage products are not economically separated under standard conditions. As one solution, it was proposed to express a variant of pro-NGF, wherein the protease cleavage site $R^1S^2K^3R^4$ in the pro-peptide is substituted at least at positions $R^1$ and $K^3$ corresponding to positions 101 and 103 of the human wildtype pro-NGF sequence (SEQ ID NO: 1) by another amino acid (WO 2013/092776 A1). In one example, $R^1$ and $K^3$, respectively, are replaced by valine (V) and alanine (A), transforming the original Furin cleavage site $R^1S^2K^3R^4$ into $V^1S^2A^3R^4$, wherein Trypsin is capable of cleaving specifically only C-terminally of $R^4$; Trypsin-mediated cleavage of a respective pro-NGF can also be referred to as the "VSAR method".

Although WO 2013/092776 A1 is silent on suitability of the VSAR method, or on substitution of Arg-Ser-Lys-Arg ($R^1S^2K^3R^4$) in general, to muteins of NGF, the VSAR method has been initially proposed to be applicable to certain variants of pro-NGF muteins, although it was reported that the proteolysis conditions needed to be titrated with care (US 2018/0086805 A1). In the course of arriving at the present invention, the present inventors found that the VSAR technology, contrary to earlier suggestions, does not satisfactorily solve purity issues associated with the recombinant production of NGF or muteins thereof. Indeed, the purification of recombinantly expressed beta-NGF or muteins thereof, not only from host cell proteins (HCP), but also from trypsin (or other protease used for cleavage) is still a challenge; needless to say, it would be required that a proteolytic enzyme is absent from a final preparation of a pharmaceutical protein, in order to avoid proteolysis during storage of the protein.

As one result of the difficulties above, to date, muteins of NGF are still not available in commercially meaningful quantity and/or purity.

Problem to be Solved

Thus, an object of the present invention includes eliminating the disadvantages associated with the state of the art. Particular objects comprise the provision of a reliable method for obtaining NGF and, more particularly, a mutein thereof. It is a particular object of the present invention to provide an improved method for the preparation of NGF and muteins thereof, which is reliable and provides NGF or muteins thereof at a high purity grade.

Various drawbacks of the state of the art define further goals for improvement addressed by the present inventors, and these goals have arrived at by the contribution described and claimed herein.

SUMMARY OF THE INVENTION

The present invention generally relates to the provision of nerve growth factor or a mutein thereof, typically in industrially relevant purity and yield.

In a first aspect, the present invention relates to a process for production of nerve growth factor (NGF) or a mutein thereof.

Preferably, the NGF or mutein thereof is human NGF (hNGF) or a mutein thereof. A mutein of hNGF is particularly preferred. Particularly preferred is a mutein of NGF, wherein the mutein is characterized by more than 50%, preferably more than 60%, more preferably more than 70%, more preferably more than 80%, even more preferably more than 90%, and most preferably more than 95% sequence identity with wild type human NGF characterized by SEQ ID NO: 2, under the proviso that the mutein is characterized by at least one mutation, preferably amino acid substitution, at any of positions 95-101 of SEQ ID NO: 2.

Preferably, the mutein is characterized by one or more of the following:
a) it is therapeutically active,
b) it is selectively recognized by a specific reagent with regard to endogenous (e.g. human) NGF.

Preferably, the mutein is a mutein of human NGF (hNGF) and is characterized by at least the absence of proline at position 61, more preferably by the substitution of proline at position 61 by another amino acid. In a particularly preferred embodiment, proline at position 61 is substituted by serine.

Preferably, the mutein is a mutein of human NGF (hNGF) and is characterized by at least one mutation of the amino acid sequence associated with reduced nociceptive activity. More preferably said mutein is characterized by at least one mutation, preferably amino acid substitution, at any of positions 95-101. Even more preferably, said mutein is characterized by substitution of the arginine in position 100. Most preferably, arginine at position 100 of hNGF is substituted by glutamic acid.

The process for production of nerve growth factor (NGF) or a mutein thereof according to the present invention preferably comprises the following steps:
(a) obtaining a precursor of NGF or of the mutein thereof,
(d) purification,
wherein the purification comprises purification on a mixed mode stationary phase.

Purification, in the broadest sense, means that the NGF or mutein thereof is separated from other molecules, including other proteins, such as host cell proteins.

Preferably, the mixed mode chromatography comprises the use of a stationary phase having a charged group, preferably negatively charged group, and an aromatic group and/or a hydrophobic group.

It is also preferred in the present invention that the precursor of NGF or a mutein thereof is subjected to a step
(c) exposure to a protease.

Said exposure is typically carried out prior to step (d).

The process of the present invention is preferably also characterized in that no chromatographic purification is performed prior to the exposure to protease. Indeed, the present inventors have surprisingly found that the digestion with protease works well and efficient also in a crude fraction obtained from a host cell, i.e. when no chromatographic purification has been performed prior to the exposure to protease. Preferably the process is a process for production of a mutein of human NGF.

Preferably, the step of obtaining (a) comprises expression of NGF or a mutein thereof, preferably recombinant expression. More preferably the recombinant expression is in a host cell. After culturing the host cell, the NGF or mutein thereof is obtained in a fraction of the cell culture. The fraction may consist of the host cells, i.e. in case the protein is substantially not secreted from the host cells. This is the case e.g. when the NGF or mutein thereof is produced in inclusion bodies and/or otherwise in an intracellular compartment including the cytosol. Suitable host cells can be selected from prokaryotic and eukaryotic host cells, although prokaryotic host cells are preferred in typical embodiments. Preferred prokaryotic host cells include *Escherichia coli* (*E. coli*), preferably *E. coli* Rosetta (DE3). More preferably, the precursor of NGF or a mutein thereof is obtained in a conformation other than the native conformation and/or in aggregates, most preferably in inclusion bodies.

Preferably the process of the present invention comprises a step (b) of (re-)folding the NGF or mutein thereof.

In one preferred embodiment, steps (b) and (c) are carried out simultaneously. In another but not necessarily mutually exclusive embodiment, step (c) is carried out after step (b).

Preferably, in step (c) the protease is a protease capable of cleaving the precursor of NGF or of a mutein thereof in such a manner that mature NGF or a mutein thereof is released. In a particular embodiment, said protease is trypsin, preferably porcine trypsin, optionally recombinantly expressed.

Preferably, the step of purification (d) comprises the following steps, preferably in sequential order:
(d1) capturing,
(d2) polishing.

Preferably, the step of capturing (d1) is carried out by chromatography, preferably column chromatography. More preferably, said step of capturing (d1) is carried out using a cation exchange chromatography stationary phase or a mixed mode chromatography stationary phase. Even more preferably said step of capturing (d1) is carried out using a mixed mode chromatography stationary phase, which is preferably Capto® MMC.

Preferably, the step of polishing (d2) is carried out by chromatography, preferably column chromatography. More preferably, said step of polishing is carried out using a cation exchange chromatography stationary phase. Even more preferably said step of capturing (d1) is carried out using SP sepharose, preferably SP sepharose with a small particle size. SP is an abbreviation for sulfopropyl.

Optionally, the process according to the first aspect of the invention comprises an additional step of adjustment to final protein concentration and/preparation of a desired formulation.

In a second aspect, the present invention relates to the use of mixed mode chromatography in the preparation of nerve growth factor (NGF) or a mutein thereof. The mixed mode chromatography is useful in the preparation of NGF or a mutein thereof. In preferred embodiments, a precursor of NGF or a mutein thereof is exposed to a protease for the purpose of digestion, and the mixed mode chromatography is used in a step subsequent to exposure to the protease. In preferred embodiments, no chromatographic purification of NGF or mutein thereof is performed prior to said exposure to protease. Preferred aspects of the process according to the first aspect of the invention generally apply also to the second aspect of the invention. Preferably said use is specifically for production of a mutein of human NGF. Preferred muteins are those described herein.

In a third aspect, the present invention relates to a mutein of NGF obtainable by the process or by the use as described herein. Preferred muteins are those described herein. Preferably, the mutein is substantially free of impurities.

In a fourth aspect, the present invention relates to the therapeutic use of a mutein of NGF as described in the third aspect of the invention. Thus, the present invention also provides said mutein of NGF for use in a method for treatment of the human or animal body by therapy.

DETAILED DISCLOSURE OF THE INVENTION

This specification in its entirety, together with the claims and the figures, discloses specific and/or preferred embodiments and variants of the individual features of the invention. The present invention also contemplates as particularly preferred embodiments those embodiments, which are generated by combining two or more of the specific and/or preferred embodiments and variants described herein for the present invention. Thus, the present disclosure also includes all of the entities, compounds, features, steps, methods or compositions referred to or indicated in this specification, individually or collectively, and any and all combinations or any two or more of said entities, compounds, features, steps, methods or compositions. Thus, unless specifically stated otherwise herein or the context requires otherwise, reference to a single entity, compound, feature, step, method or composition shall be taken to encompass one and a plurality (i.e. more than one, such as two or more, three or more or all) of those entities, compounds, features, steps, methods or compositions. Unless specifically stated otherwise or the context requires otherwise, each embodiment, aspect and example disclosed herein shall be taken to be applicable to, and combinable with, any other embodiment, aspect or example disclosed herein.

The person of ordinary skill in the art will appreciate that the invention described herein is susceptible to variations and modifications other than those specifically described. Thus, the present disclosure is not limited in scope by the specific embodiments described herein, which are provided herein for the purposes of illustration and of exemplification. Functionally or otherwise equivalent entities, compounds, features, steps, methods or compositions are within the scope of the present disclosure. it will be apparent to the person of ordinary skill in the art that the present disclosure includes all variations and modifications of the entities, compounds, features, steps, methods or compositions literally described herein.

Each of the references cited herein (including all patents, patent applications, scientific publications, manufacturer's specifications, instructions, presentations, etc.), whether above or below, are hereby incorporated by reference in their entirety. Nothing herein is to be construed as an admission that the present invention would not be entitled to antedate a specific teaching and/or as an admission that a specific reference, other than the common general knowledge, contains information sufficiently clear and complete for it to be carried out by a person skilled in the art.

Generally, unless specifically defined otherwise, all technical and scientific terms used herein have the same meaning as commonly understood by one of ordinary skill in the art (e.g., in genetics, molecular biology, gene expression, cell biology, cell culture, immunology, neurobiology, chromatography, protein chemistry, and biochemistry). Textbooks and review articles published e.g. in English typically define the meaning as commonly understood by a person of ordinary skill in the art.

The expression "and/or", e.g., "X and/or Y" shall be understood to mean either "X and Y" or "X or Y" and shall be taken to provide explicit disclosure of "and", of "or" and of both meanings ("and" or "or").

As used herein, unless specified otherwise, the terms "about", "ca." and "substantially" all mean approximately or nearly, and in the context of a numerical value or range set forth herein preferably designates +/−10%, more preferably +/−5%, around the numerical value or range recited or claimed.

Unless expressly specified otherwise, the word "comprise", or variations such as "comprises" or "comprising" is used in the context of the present document to indicate that further members may optionally be present in addition to the members of the list introduced by "comprising". It is, however, contemplated as a specific embodiment of the present invention that the term "comprising" encompasses the possibility of no further members being present, i.e. for the purpose of this embodiment "comprising" is to be understood as having the meaning of "consisting of".

Unless expressly specified otherwise, all indications of relative amounts regarding the present invention are made on a weight/weight basis. Indications of relative amounts of a component characterized by a generic term are meant to refer to the total amount of all specific variants or members covered by said generic term. If a certain component defined by a generic term is specified to be present in a certain relative amount, and if this component is further characterized to be a specific variant or member covered by the generic term, it is meant that no other variants or members covered by the generic term are additionally present such that the total relative amount of components covered by the generic term exceeds the specified relative amount; more preferably no other variants or members covered by the generic term are present at all.

A "cell" is a biological entity composed of cytoplasm enclosed within a membrane. As used in connection with the process and the use according to the present invention, the term "cell" in certain described embodiments preferably refers to a prokaryotic cell.

As used herein, the terms "chromatography", "chromatographic" and the like generally refer to a technique suitable for the separation of a mixture, wherein the mixture is added to a non-liquid material called the "stationary phase" with the purpose to separate, at least partially, one or more constituents of the mixture. For that purpose, the stationary phase may be exposed to a fluid and/or the mixture may be dissolved in a fluid; said fluid contacted with the stationary phase may also referred to as "mobile phase". The term "mobile phase" as used herein, has the meaning typically used in the art and can refer to all fluids brought in contact with the stationary phase during chromatography, i.e. to wash fluids as well as to fluids (mixtures) comprising a protein of interest, such as one or more of the proteins described herein. In the present invention, the mixture subjected to chromatography, as specified herein, typically comprises one or more proteins, such as in particular the proteins described herein, such as NGF, muteins thereof, a precursor of NGF, a precursor of an NGF mutein, a protease, and/or host cell proteins (HCP). In general, any step that is "carried out by chromatography", as described herein, may synonymously referred to as a "chromatographic step".

A "stationary phase" typically comprises a typically comprises a base matrix, which is a water-insoluble material, usually in particle from or gel form, such as a resin. In many cases, including embodiments described herein, a stationary phase comprises a base matrix and a moiety that can bind to at least one component comprised in the mixture that is to be subjected to chromatography. The base matrix is normally a water-insoluble material, usually in particle from or gel form. Non-limiting examples of base matrices are sepharose and agarose, for example highly rigid agarose.

A "chromatographic step" as used herein, refers to the action of adding to a chromatography material (preferably a stationary phase) a liquid comprising at least one compound to be analyzed and/or to be purified, which is preferably a protein (and in the context of the present invention said protein is most preferably NGF of a mutein thereof), optionally washing the chromatography material with one or more wash solutions, and eluting said at least one compound. In that context, a process characterized by two chromatographic steps, for illustration, is characterized in that a liquid comprising at least one such compound to be analyzed and/or to be purified is added to a first chromatographic material, as above described, and, after elution therefrom, the liquid comprising at least one such compound is added to a second chromatographic material, from which it is also eluted, as above described. It is the aim of any "chromatographic step" that at least one component comprised in the mixture applied to a stationary phase, preferably in chromatography, binds to the stationary phase. Such compound may be one or more proteins described herein. The compound may be recovered from the stationary phase, e.g. by exchange of mobile phase and/or by continued exposure to the mobile phase over time.

The term "binds", when used with reference to chromatography, such as to describe the binding capacity of a stationary phase, is not particularly limited, but typically refers to non-covalent binding. Thus typically at least one component comprised in a mixture, such as at least one protein, binds non-covalently to the stationary phase. A chromatographic step optionally but preferably comprises the washing of the stationary phase to which the at least one component is bound. The at least one component may be at least one protein, such as at least one protein described herein.

The term "culture vessel" or "cell culture vessel" generally refers to a vessel that is suitable for cultivation of host cells. A particular type of culture vessel can be chosen by the skilled person, taking into consideration the type of host cell, scale of the culture, aeration and feed requirements, etc. . . . . These can be determined based on the common general knowledge and the guidance herein.

The terms "disulfide" and "disulfide bond" are used, in the context of the present invention, within the meaning commonly used in the art. In general, a "disulfide" refers to a functional group with the structure R—S—S—R'. The linkage is also called an "SS-bond" and is usually derived by the coupling of two thiol groups. Disulfide bonds in proteins are formed between the thiol groups of the cysteine residues by the process of oxidative folding; such a specific disulfide bond between the thiol groups of two cysteine residues can also be referred to as "disulfide bridge". Without wishing to be bound to a particular theory, it is normally understood in the art that, in In eukaryotic cells, disulfide bridges are formed in the lumen of the endoplasmic reticulum (and the mitochondrial intermembrane space) but not generally in the cytosol, and, regarding prokaryotes, disulfide bridges are formed in the periplasm (of respective organisms, particularly Gram-negative bacteria); disulfide bridges can also be found in proteins of the extracellular environment of both eukaryotic and prokaryotic cells.

The terms "express", "expressed" and "expression", "gene expression" and the like, as used herein, relate to the use of information from a gene in the synthesis of a functional gene product. Gene expression comprises at least the transcription, and optionally comprises one of more additional features, optionally selected from the open list comprising translation and post-translational modification. In the context of recombinant expression of a protein in a host cell, the term normally implies that the protein is produced by the host cell (in any compartment of the cell and/or secreted and/or incorporated in inclusion bodies), unless the context dictates otherwise.

The term "heterologous" as used herein describes something consisting of multiple different elements or origins. For example, in a non-human host cell which comprises a human gene (or gene encoding a mutein of a human gene) said gene is "heterologous" to the cell, and the cell may be capable of "heterologous" expression of the respective gene. Heterologous gene expression can also be referred to as "recombinant".

The term "inclusion body" has the meaning typically used in the art and is meant to refer to aggregates or particles found in the cytosol or in the periplasm of a host cell; inclusion bodies typically comprise protein, such as, in particular, protein expressed recombinantly in the host cell. Without wishing to be bound to any particular theory, it is understood that in the field of recombinant expression, inclusion bodies typically contain the recombinantly expressed protein but relatively little host cell protein (HCP), ribosomal components or DNA/RNA fragments. Without wishing to be bound to any particular theory, it is understood that inclusion bodies typically comprise, at least in part, protein that is not properly folded (misfolded protein), in particular misfolded recombinantly expressed protein. It is understood that inclusion bodies typically comprise protein in a non-properly folded form, i.e. in the context of the present invention they typically comprise a precursor of NGF or a mutein thereof in a non-properly folded form. The term "misfolded" generally describes a biomolecule, such as a nucleic acid or polypeptide, which is not on the native conformation, i.e. in a non-properly folded form By "isolated" is meant material that is substantially or essentially free from components that normally accompany it in its native state. For example, an "isolated peptide" or "isolated protein", as used herein, refers to a peptide or protein, respectively, which has been purified from the cellular and extracellular environment, such as tissue, which surround it in a naturally-occurring state, e.g., from the cell in which it has been expressed, such as a host cell. In an alternative description, an "isolated peptide" or "isolated protein" and the like, as used herein, refer to in vitro isolation and/or purification of a peptide or protein, respectively, from its natural cellular environment, and from association with other components of the environment in which the peptide or protein normally resides. In another example, an "isolated cell", as used herein, refers to a cell, which has been purified from the cellular and extracellular environment, such as tissue or cell colonies, which surround it in a naturally-occurring state, e.g., a host cell which has been removed from the environment that is normally adjacent to the cell. In accordance with the above definition of the word "isolated", "to isolate", as used herein, is the verb that describes the activity to obtain "isolated" material, such as e.g. an isolated cell or an isolated peptide or protein.

The term "neurotrophin" is used herein to refer to a substance that is capable of stimulating the growth of neurons and other cells, including NGF and muteins of NGF with such capabilities.

The term "nerve growth factor", abbreviated "NGF" or "beta-NGF" stands for a neurotrophic factor and neuropeptide involved in the regulation of growth, maintenance, proliferation, and survival of certain neurons and other cells, in accordance with the common meaning in the art (see e.g. Levi-Montalcini, 2004, Progress in Brain Research, vol. 146, p. 525-527). Unless the context dictates otherwise, the term nerve growth factor usually refers to the 2.5S, 26-kDa beta subunit of the protein, which is biologically active: wild-type NGF binds with at least two classes of receptors: the tropomyosine receptor kinase A (TrkA) and low-affinity NGF receptor (LNGFR/p75NTR). The term "NGF", unless specified otherwise, refers to NGF of any species, preferably mammalian species; however, human NGF is always preferred. "hNGF", as used herein stands for human NGF. Unless the context dictates otherwise, the terms "NGF" and "hNGF" refer to wild-type NGF, i.e. hNGF stands for wild-type NGF. The amino acid sequence of wild-type human NGF corresponds to positions 121-239 of SEQ ID NO: 1 (grey in FIG. 15A). The sequences of non-human NGF are available, e.g., in the scientific literature, through sequence searches, such as BLAST, using positions 121-239 of SEQ ID NO: 1 as bait, and in public protein databases such as Swissprot.

Particular when used in the context "NGF or mutein thereof", or the like, it is intended to mean that "NGF" and the "mutein" are alternatives, and that the term "NGF" is not itself a mutein of NGF, but a wild-type NGF, such as, in particular wild-type human NGF.

The terms "mature part" "mature portion", with reference to NGF or a mutein thereof, are used interchangeably with the term "beta-NGF" and refer to a polypeptide of NGF or of a NGF mutein (as the case may be) which is characterized in that it does not provide the pro-peptide (and hence, of course, not the pre-pro-peptide) of NGF or of a respective mutein. Preferably, the mature part does also not comprise a C-terminal cleavable peptide encoded by the wild-type NGF open reading frame; such C-terminal cleavable peptide, in the case of human NGF, consists of the two amino acid residues "RA" (240 and 241 in SEQ ID NO: 1). More particularly, the mature part is obtainable, without limitation, by cleavage of a pro-NGF with the protease Furin. Although Furin is not commercially available, at present, at high purities, the preceding sentence is to be understood broadly, as the Furin cleavage site as such is known, and thus the mature part is a polypeptide encoded by an open reading frame encoding NGF (or a mutein thereof), which does not comprise the Furin cleavage site. For example, the Furin cleavage site of human NGF, and of many orthologs, is well known to consist of the sequence $R^1S^2K^3R^4$ (one letter amino acid code, sequences numbered from N to C terminus; boxed in FIG. 15A)). In mature NGF, normally neither the Furin cleavage site nor any amino acid N-terminally of the Furin cleavage site is present. For illustration, the mature part of human NGF consists of the polypeptide represented by amino acid positions 122-239 of SEQ ID NO: 1. The mature part of non-human NGF may be identified, e.g. by sequence search and/or sequence analysis, wherein said mature part of human NGF is used for sequence alignment.

The term "precursor", as used herein with reference to NGF and a mutein thereof, refers to any peptide sequence from which NGF or a mutein thereof is obtainable through proteolytic cleavage. For illustration, both pro-NGF and pre-pro-NGF, as well as variants thereof, are typical examples of precursors of NGF; and both pro-NGF mutein and pre-pro-NGF mutein, as well as variants thereof, are typical examples of precursors of NGF mutein. The term "precursor" as used herein, can refer to precursors the most C-terminal amino acid residue of which is the most C-terminal residue of NGF, and also to precursors which extend at the C-terminus beyond the most C-terminal residue of NGF, as long as NGF is obtainable therefrom by proteolytic cleavage: although the naturally occurring precursor of wild-type human pro-NGF (SEQID NO: 1) comprises a C-terminal dipeptide (amino acid residues 240 and 241 in SEQ ID NO: 1, bold in FIG. 1), it is preferable that the precursor of NGF obtained and used in the present invention, and any mutein thereof, does not comprise a C-terminal cleavable peptide encoded by the wild-type NGF open reading frame; such C-terminal cleavable peptide, in the case of human NGF, consists of the two amino acid residues "RA" (240 and 241 in SEQ ID NO: 1). Particular when used in the context "precursor of NGF or mutein thereof", or the like, it is intended to mean that "precursor of NGF" and the "precursor of a mutein NGF" are alternatives, and that the term "precursor of NGF" is not itself a precursor of a mutein of NGF, but a precursor of wild-type NGF, such as, in particular a precursor of wild-type human NGF.

The terms "NGF mutein" and "mutein of NGF", or, with reference to NGF "mutein thereof", are used herein interchangeably to refer to a polypeptide which is characterized by at least one mutation, compared to wild-type NGF, as further described in detail herein.

The terms "pre-peptide" or "pre-sequence", as used herein, generally interchangeably refer to a polypeptide sequence encoded by part of the NGF open reading frame, N-terminally directly adjacent to the pro-peptide. For illustration: a pre-peptide is NGF consists of the sequence comprising the continuous sequence ranging from reside 1 of SEQ ID NO: 1 to residue 18 of SEQ ID NO: 1. The sequences of the respective pre-peptides of precursors of non-human NGF are available, e.g., in the scientific literature, through sequence searches, such as BLAST, using positions 1-18 of SEQ ID NO: 1 as bait, and in public protein databases such as Swissprot. A polypeptide or protein consisting of the pre-peptide and of pro-NGF (or a mutein thereof), wherein the C-terminus of the pre-peptide is directly adjacent to the N-terminus of pro-NGF, can be referred to herein as "pre-pro-NGF (or a mutein thereof)".

The terms "pro-peptide" or "pro-sequence", as used herein, generally interchangeably refer to a polypeptide sequence encoded by part of the NGF open reading frame, N-terminally directly adjacent to mature NGF, but which polypeptide sequence does not include the pre-peptide. For illustration: a pro-peptide is comprised in the wild-type precursor of NGF. The pro-peptide of the precursor of NGF, consists of the sequence comprising the continuous sequence ranging from residue 19 of SEQ ID NO: 1 to residue 121 of SEQ ID NO: 1. The sequences of the respective pro-peptides of non-human pro-NGF are available, e.g., in the scientific literature, through sequence searches, such as BLAST, using positions 19-121 of SEQ ID NO: 1 as bait, and in public protein databases such as Swissprot. A polypeptide or protein consisting of the pro-peptide and of pro-NGF (or mutein thereof) can be referred to herein as "pro-NGF (or mutein thereof)".

"pro-NGF", as used herein, refers to a peptide sequence comprising both the mature part of NGF and the respective pro-peptide, but not the respective pre-peptide. Human pro-NGF consists of the sequence comprising the continuous sequence ranging from reside 19 of SEQ ID NO: 1 to at least residue 239 of SEQ ID NO: 1. Although wild-type human pro-NGF comprises a C-terminal dipeptide (amino acid residues 240 and 241 in SEQ ID NO: 1, bold in FIG. 1), it is preferable that the pro-NGF obtained and used in the present invention does not comprise a C-terminal cleavable peptide encoded by the wild-type NGF open reading frame; such C-terminal cleavable peptide, in the case of human NGF, consists of the two amino acid residues "RA" (240 and 241 in SEQ ID NO: 1). The sequences of non-human pro-NGF are available, e.g., in the scientific literature, through sequence searches, such as BLAST, using positions 19-239 of SEQ ID NO: 1 as bait, and in public protein databases such as Swissprot. Particularly when used in the context "pro-NGF or mutein thereof", or the like, it is intended to mean that "pro-NGF" and the "mutein of pro-NGF" are alternatives, and that the term "pro-NGF" is not itself meant to refer to a mutein of pro-NGF, but a wild-type pro-NGF, such as, in particular wild-type human pro-NGF.

As used herein, the terms "medium" and "growth medium" are used interchangeably to refer to an aqueous mixture suitable for cultivation of cells, particularly host cells, e.g. bacterial cells. The aqueous mixture is typically a solution, although suspensions and colloidal mixtures are also comprised by the term. The medium is typically liquid, although some media can also be temporarily frozen, e.g. for storage purposes; in any case, a medium is used for cell culture when it is liquid. A medium at least one supplement, e.g. antibiotic, is also referred to as "medium". A medium may be e.g. a chemically defined medium or a complex medium. Preferred media are free of animal-derived constituents.

The term "mutation", as used herein, refers to the alteration of the nucleotide sequence of the genome of an organism, virus, or extrachromosomal DNA or other genetic elements. The term also extends to mutations of an amino acid sequence, particularly the amino acid sequence of a gene that carries at least one (non-silent) mutation. Unless specified otherwise, a mutation of the nucleotide sequence is a permanent alteration. In general, a mutation of the nucleotide sequence can result in many different types of change in sequences: mutations in genes can either have no effect, alter the product of a gene, or prevent the gene from functioning properly or completely. Unless specified otherwise, the wild type sequence is used as a reference sequence to describe a mutation. Thus, a mutation "at position" 100 of a polypeptide sequence indicates that the molecule characterized by the mutation does not have the same amino acid residue at position 100 as the wild type polypeptide. Specific types of mutations of a nucleotide sequence and/or an amino acid sequence include alterations such as deletions, substitutions, additions, insertions and splice variants. A "deletion" with respect to a nucleotide sequence refers to the absence of one or more nucleotide(s) in the nucleotide sequence. A "deletion" with respect to an amino acid sequence refers to the absence of one or more amino acid residue(s) in the polypeptide. An "addition" with respect to a nucleotide sequence refers to the presence of one or more additional nucleotide(s) in nucleotide sequence. An "addition" with respect to an amino acid sequence refers to the presence of one or more additional amino acid residue(s) in the related polypeptide. A "substitution" with respect to a nucleotide sequence refers to the replacement of one or more nucleotide(s) by (an) other nucleotide(s) in the nucleotide sequence. A "substitution" with respect to an amino acid sequence refers to the replacement of one or more amino acid residue(s) by (an) other amino acid residue(s) in the polypeptide. Additions, deletions and substitutions to a nucleotide sequence, such as to an open reading frame, may be 5' terminus, the 3' terminus, and/or internal. Additions, deletions and substitutions to a polypeptide, may be at the amino terminus, the carboxy terminus, and/or internal. An "insertion" with respect to a nucleotide sequence and/or a polypeptide sequence is an addition of one or more nucleotides, or one or more amino acid residues, respectively, specifically at an internal position of the respective sequence.

The term "mutein" is generally intended to refer to an amino acid sequence which is different from the wild type sequence. Muteins can contain different combinations of mutations, alone or in combination, including more than one mutation and different types of mutations. Specifically with respect to NGF, and as used in the present disclosure, the term "mutein" (also "NGF mutein" or mutein of NGF") refers to a polypeptide with an amino acid sequence which is different from the wild type NGF sequence, more typically to an amino acid sequence which is not found in nature. Therefore, for illustration, unless the context dictates otherwise, murine NGF (wild type) will not normally be considered an "NGF mutein" although it indeed differs from human NGF (wild type) in several amino acid positions. In the narrow sense, the term "NGF mutein" is specifically reserved for polypeptides not found in nature (i.e. non wild-type). On the level of nucleic acid sequences, a "mutein nucleic acid sequence" is one that encodes a mutein (peptide or protein). In cases of polymorphisms at the nucleic acid sequence which are, however, not reflected at the level of the respective encoded peptide or protein (silent mutations, degeneracy of the genetic code), the term "mutein", on nucleic acid level, preferably specifically refers only to those nucleic acid molecules which encode a mutein, (on polypeptide level).

The terms "multi" and "multiple" as used herein mean a multitude, i.e. any number of two or more.

The terms "nucleic acid" and "polynucleotide" are used interchangeably herein, and refer to both RNA and DNA, including cDNA, genomic DNA, synthetic DNA, and DNA/RNA equivalents containing nucleotide analogs, phosphate analogs and/or sugar analogs. A nucleic acid can be double-stranded or single-stranded (i.e., a sense strand or an antisense strand). Non-limiting examples of polynucleotides include genes, open reading frames, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated nucleic acids of any type and sequence nucleic acid probes, and primers, as well as nucleic acid analogs. Nucleic acids may have any type of three-dimensional structure.

The term "peptide" according to the invention comprises oligo- and polypeptides and refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently to a chain by peptide bonds.

The term "production scale" typically refers to the production of one or more compounds described herein at a preparative scale. Although the term is not strictly limited, one may speak of "production scale" when fermentation is carried out in media volumes of 1 l or more, and/or when purification is carried out on chromatography columns having a column volume of 1 ml or more. The term "laboratory scale", short "lab scale" includes any scale below "production scale". The term "scale up" refers generally to an increase of volume, e.g. an increase of fermentation volume or column volume, for example, but not limited thereto, from lab scale to production scale; a scale up may also refer to the further increase of volume, all within the production scale (for illustration, see e.g. Example 7).

The term "protein" preferably refers to large peptides, preferably to peptides with more than 100 amino acid residues, but in general the terms "peptide" and "protein" are synonyms and are used interchangeably herein, unless the context dictates otherwise.

The term "pharmaceutically active peptide or protein" refers to a peptide or protein that can be used in the treatment of a subject where the peptide or protein would be of benefit, e.g., in ameliorating the symptoms of a disease or disorder. For example, a pharmaceutically active protein can be used to treat a cell or an individual which does not normally express a protein, or not at the desired levels, or which mis-expresses a protein, e.g., a pharmaceutically active protein can compensate for a mutation, or for lack of sufficiently high expression, by supplying a desirable protein. In addition, a "pharmaceutically active peptide or protein" can have a positive or advantageous effect on the condition or disease state of a subject when administered to the subject in a therapeutically effective amount. Preferably, a pharmaceutically active peptide or protein has curative properties and may be administered to ameliorate, relieve, alleviate, reverse, delay onset of or lessen the severity of one or more symptoms of a disease or disorder. A pharmaceutically active peptide or protein may have prophylactic properties and may be used to delay the onset of a disease or to lessen the severity of such disease or pathological condition. The term "pharmaceutically active peptide or protein" includes entire proteins or polypeptides, and can also refer to pharmaceutically active fragments thereof. It can also include pharmaceutically active analogs of a peptide or protein. In the context of the present invention, the term "pharmaceutically active peptide or protein" particularly includes NGF and muteins thereof. For the avoidance of doubt, all muteins of NGF described herein are comprised by this term.

An "open reading frame" or "ORF" is a continuous stretch of codons beginning with a start codon and ending with a stop codon.

According to the present invention, a nucleic acid may encode a peptide or protein. Accordingly, a nucleic acid may contain a coding region (open reading frame (ORF)) encoding a peptide or protein. For example, a nucleic acid may encode and express an antigen or a pharmaceutically active peptide or protein.

The term "subject" relates to a mammal. For example, mammals in the context of the present invention are humans, non-human primates, domesticated animals including but not limited to dogs, cats, sheep, cattle, goats, pigs, horses etc., laboratory animals including but not limited to mice, rats, rabbits, etc., as well as animals in captivity such as animals of zoos. The term "subject" as used herein particularly includes humans.

In the context of the present invention, the term "transcription" refers to a process wherein the genetic code in a DNA sequence is transcribed into RNA. The transcribed RNA may be translated into a peptide or protein:

The term "translation" according to the invention refers to the process by which a messenger RNA directs the assembly of a sequence of amino acids on the ribosomes of a cell to make a peptide or protein. A transcript, generated e.g. by transcription, and comprising a coding strand specific for the peptide or protein, may serve as template for translation.

The term "trypsin", as used herein, generally refers to a proteolytic enzyme classified as EC 3.4.21.4). Trypsin cleaves peptide chains mainly at the carboxyl side of the amino acids lysine or arginine, normally except when either is followed by proline. Without wishing to be bound by theory, it is understood that trypsin is a serine protease, and that trypsin is naturally found in the digestive system of many vertebrates, where it hydrolyzes proteins. Preferred in the present invention is trypsin from recombinant sources. Although, in vivo, trypsin is formed together with a propeptide (termed "trypsinogen"), the term "trypsin", as used herein preferably refers to mature trypsin devoid of any pro-peptide. The use of trypsin for proteolytic cleavage can also be referred to as "trypsin proteolysis" or "trypsinization", and proteins that result from cleavage with trypsin are said to have been "trypsinized".

A "variant" of a precursor of NGF or of a mutein thereof, such as e.g. of a pro-NGF or of a pre-pro-NGF, refers to a polypeptide or protein wherein the amino acid sequence that is not part of the mature NGF (beta-NGF) is characterized by at least one mutation in comparison with a wild-type precursor of NGF or of a mutein thereof, such as with a wild-type pro-NGF or a wild-type pre-pro-NGF; said at least one mutation is preferably found N-terminal to the amino acid sequence of the mature NGF (beta-NGF). Thus, as used herein, a "variant" of a precursor of NGF or of a mutein thereof, as used herein, refers to a peptide or protein wherein the pre-peptide and/or the pro-peptide of a precursor of NGF or of a mutein thereof is characterized by at least one mutation, with respect to the amino acid sequence of the pre-peptide and/or the pro-peptide, for example but without limitation those variants described in WO 2013/092776 A1 and in by US 2018/0086805 A1. For illustration, WO 2013/092776 A1 describes "variants" of pro-NGF wherein the (wild-type) Furin cleavage site is absent due to one or more specific mutations.

The term "vector" or "cloning vector" generally refers to a nucleic acid that can be introduced into a host cell. Example vectors include, without limitation, plasmids, phages and all other types of nucleic acids that can be introduced into a host cell. The term "vector" is to be understood broadly and will comprise vectors which encode a peptide or protein for heterologous expression (such vectors may serve as templates, for the generation of transcripts), and those which do not. Vectors of the first type will contain an open reading frame encoding a protein or peptide (e.g. NGF or mutein thereof, in particular), which may be expressed, when the vector is present in a host cell. Although the type of vector that the skilled person will choose will be dependent on the type of host cell that the skilled person will choose, in a particular case, cloning vectors for all common host cells, including *E. coli*, are commercially available, and the skilled person will thus choose a particular vector in full consideration of the host cell chosen.

The term "wild-type" refers to any sequence, nucleic acid or amino acid sequence in particular, that is found in nature. For illustration, SEQ ID NO: 1 shows the amino acid sequence of a precursor of wild-type human NGF; SEQ ID NO: 2 shows the amino acid sequence of wild-type human NGF.

The present invention is based on several findings, which are interrelated and thus together lead the inventors to arrive at the various aspects of the invention, which will all be described individually in the following. All aspects of the present invention are based inter alia on the finding that the stability and thus the long-term purity of NGF and a mutein thereof can be improved by the aspects and embodiments described herein.

Nerve Growth Factor (NGF) or a Mutein Thereof

The present invention generally relates to the provision of nerve growth factor (NGF) or a mutein thereof, typically in industrially relevant purity and yield. Without wishing to be bound to any particular theory, it is presently understood that NGF is required in vivo for the development and survival of specific neuronal populations, and NGF is therefore also classified as a neurotrophin. Nerve growth factor is a homodimeric peptide that naturally triggers proliferation and homeostasis of neurons.

In the present invention, NGF and each and every mutein described herein, generically and specifically, can also be referred to as a pharmaceutically active peptide or protein.

Certain muteins of NGF, when administered to an animal for example, can also have a function in vivo in the proliferation and homeostasis of neurons, and respective muteins are preferred herein.

The NGF is not particularly limited, but particularly preferred are all types of mammalian NGF, such as e.g. mouse NGF, rat NGF, and, most preferably, human NGF. Preferably, the NGF is human NGF (hNGF, UniProt/SwissProt Number P01138). For the sequence of human NGF (SEQ ID NO: 2) in the context of its precursor (SEQ ID NO: 1), see FIGS. 15A, 15B and 15C and the corresponding legend.

Everything described herein in relation to nerve growth factor (NGF) or a mutein thereof is applicable to each and every aspect and embodiment of the present invention, unless the context clearly dictates otherwise. More particularly, all the muteins described herein may be purified by the process according to the first aspect of the invention, all the muteins described herein are obtainable through the use according to the second aspect of the invention, and all the muteins described herein comply with the third aspect of the invention, and all the muteins described herein may be used according to the fourth aspect of the invention.

Preferably, the NGF or NGF mutein obtainable according to the present invention is characterized by the presence of three disulfide bridges, as is mature wild-type NGF in vivo. The presence of the three disulfide bridges is an indication that the NGF or mutein thereof is properly folded and biologically active.

Preferably, the NGF or NGF mutein obtainable according to the present invention is biologically active. The term "biologically active", with respect to NGF, refers to the biological activity of pro-NGF. The activity may be, for example, determined according to an assay as described by Chevalier et al., 1994, Blood, vol. 83, p. 1479-1485, which is incorporated herein by reference. Regarding biological activity, it is known that NGF induces cell survival through the activation of the Akt pathway and that the activation of cytoplasmic domain of the Tropomyosin-related kinase A (TrkA) promotes cell growth through the activation of the shc pathway (reviewed in Reichardt, 2006, Phil. Trans. R. Soc. B, vol. 361, p. 1545-1564). The induction of cell growth and of cell differentiation and plasticity is also mediated by the activation of PKC pathway through PLCγ (reviewed in Reichardt, above). Preferably, the action of the mutein according to the aspects of the present invention on TrkA is comparable or essentially identical to the one of the respective wild type NGF. For example, an assay for determining the effect of NGF and of a mutein thereof on TrkA has been described in WO 2008/006893 A1, and said assay may be employed in the present invention. The induction of TrkA phosphorylation by a mutein of human NGF characterized by the mutation Pro61Ser (P61S) has previously been shown to be completely similar to that of wild type human NGF (WO 2008/006893 A1). Unless the context dictates otherwise, also the muteins of NGF which are associated with reduced nociceptive activity, such as those described herein (and including, as an illustrative example, those described by Malerba et al. PLOS One, 2015, vol. 10, e0136425), can be referred to as "biologically active", in the context of the present disclosure. The terms "biologically active" and "therapeutically active" with reference to NGF or muteins thereof, are used interchangeably in the present disclosure.

In the present invention it is preferred that the most N-terminal basic residue of wild type NGF is not substituted, also not in a mutein of NGF. For the case of human NGF or muteins thereof this means that the arginine residue at position 9 of SEQ ID NO: 2 (position 130 of SEQ ID NO: 2) is not characterized by a mutation, in other words is "not mutated". In other words, the arginine (R) residue at position 130 of SEQ ID NO: 1 is present. Position 130 of SEQ ID NO: 1 is indicative to define the position, and the skilled person will understand that in different precursors and/or muteins of NGF the number may be different from 130. However, a position equivalent to position 130 of SEQ ID NO: 1 can be identified by the skilled person in any NGF or pro-NGF, or precursor of any of these, by aligning the sequence of the respective NGF or pro-NGF, or precursor of any of these with the sequence of SEQ ID NO: 1. Respective wild-type NGF and muteins thereof can particularly profit from the process according to the present invention, wherein undesired cleavage at said position is avoided as a result of the improvements reported herein.

In typical embodiments, the NGF or mutein thereof according to the present invention is not glycosylated. This applies particularly to NGF obtainable from inclusion bodies, particularly bacterial inclusion bodies.

Preferably, the mutein of NGF is characterized by one or more of the following:
  a) it is therapeutically active;
  b) it is selectively recognized by a specific reagent with regard to endogenous hNGF.

A mutein of human NGF (hNGF) is particularly preferred. Preferred muteins will be described in the following.

Any mutein of NGF, according to the present invention, has typically more than 50%, preferably more than 60%, more preferably more than 70%, more preferably more than 80%, even more preferably more than 90%, and most preferably more than 95% sequence identity with a wild type NGF (reference NGF). The reference NGF may be selected from any naturally occurring NGF, more preferably mammalian NGF; typical examples are human NGF (SEQ ID NO: 2), mouse NGF and rat NGF, among which human NGF (SEQ ID NO: 2) is most preferred as a reference NGF. In other words and more precisely defined, preferably, the mutein of NGF has a sequence identity of 80% or more, more preferably 90% or more, more preferably 95% or more, such as e.g. about 95%, about 96%, about 97%, about 98%, with a respective wild-type NGF (reference NGF). Said wild-type NGF (reference NGF) is not particularly limited, but particularly preferred are all types of mammalian NGF, such as e.g. mouse NGF, rat NGF, and, most preferably, human NGF (SEQ ID NO: 2). The mutein of NGF is preferably a homolog of NGF. Indeed, it is generally recognized that a common rule of thumb is that two sequences are homologous if they are more than 30% identical over their entire lengths (Pearson, 2013, Curr. Protoc. Bioinformatics, 2013, vol. 42, 3.1.1-3.1.8).

Thus, it is particularly preferred that the mutein is a polypeptide having more than 50%, preferably more than 60%, more preferably more than 70%, more preferably more than 80%, even more preferably more than 90%, and most preferably more than 95% sequence identity with wild type human NGF, wherein wild type human NGF characterized by SEQ ID NO: 2. Particularly preferred is a mutein of NGF, wherein the mutein is characterized by more than 50% sequence identity with wild type human NGF characterized by SEQ ID NO: 2, under the proviso that the mutein is characterized by at least one mutation at any of positions 95-101 of SEQ ID NO: 2. Said at least one mutation is preferably a substitution (amino acid substitution). In case of multiple mutations, at least one of those mutations is preferably a substitution. The term "mutation at any of positions 95-101 of SEQ ID NO: 2" means that the respective mutein differs at at least one of said positions from the polypeptide of SEQ ID NO: 2.

In the context of the present invention, "sequence identity" is identified in pairwise sequence alignments as described e.g. by Pearson (2013, Curr. Protoc. Bioinformatics, 2013, vol. 42, 3.1.1-3.1.8).

Preferably the mutein of NGF has a molecular weight between 10 and 17 kDa, more preferably between 11 and 16 kDa, more preferably between 12 and 15 kDa, more preferably between 13 and 14 kDa, such as e.g. 13.5 kDa. Human NGF (wild type), for example, has a molecular weight of approximately 13.5 kDa.

A mutein which can be selectively recognized by a specific reagent with regard to endogenous (wild type) NGF is preferred. Such a mutein which can be selectively recognized by a specific reagent with regard to endogenous (wild type) NGF not particularly limited, as long as an assay, in vitro or in vivo, exists or can be made available that allows for such selective recognition. It is known that, e.g. in humans, endogenous NGF levels are variable, both from individual to individual and in a single individual at various times, and according to stress conditions (see e.g. WO 2008/006893 A1). Thus, for therapeutic applications, it is desirable to use or use a mutein of NGF which is distinguishable from the respective endogenous NGF, and such muteins are particularly preferred in all aspects of the present invention. For example, for therapeutic applications in humans, it is desirable to use or administer a mutein of NGF which is distinguishable from the respective endogenous human NGF.

Preferably, the mutein is a mutein that can be distinguished from a wild-type NGF, e.g. by an immunoreactive molecule, such as by an antibody, nanobody, darpin or the like. Preferably, the immunoreactive molecule is an antibody (e.g. a monoclonal antibody or a synthetic or a biotechnological or a humanized antibody), or a fragment thereof. An antibody or other immune reactive molecule may recognize an epitope. The term "epitope" refers to an antigenic determinant in a molecule such as an antigen, i.e., to a part in or fragment of the molecule that is recognized, i.e. bound, by the immune system, for example, that is recognized by an antibody or other immune reactive molecule. Detection of an epitope specific for any particular antigen normally allows to conclude that that particular antigen is present. In a preferred embodiment, the NGF mutein is characterized by at least one antigen which is not present in wild type NGF (reference NGF). For example, in the case of a mutein of human NGF (hNGF), it is preferred that the mutein of human NGF is characterized by at least one antigen which is not present in wild type hNGF. Such mutein characterized by at least one antigen which is not present in wild type NGF can be specifically recognized, normally with an antibody or other immunoreactive molecule. Optionally, the antibody or other immunoreactive molecule is labelled (e.g. fluorophore-labelled, enzyme labelled etc.) itself, or recognized by a labelled secondary antibody or other immunoreactive molecule, which may be added for that purpose.

According to the present invention, a mutein characterized by at least one antigen which is not present in wild type NGF can be specifically recognized e.g. as follows: For example, an antibody capable of selectively recognizing a mutein of hNGF having a serine at position 61, which is located in in loop III of hNGF, has been described in WO 2008/006893 A1, and such and other antibodies are useful in the present invention to distinguish a respective mutein from the respective endogenous NGF, in this case from wild type human NGF illustrated in SEQ ID NO: 2). Thus, in some embodiments, the mutein is a mutein of human NGF (hNGF) is characterized by at least one amino acid substitution residing in loop III of hNGF, more particularly at least by the absence (e.g. substitution) of proline at position 61, more preferably by the substitution of proline at position 61 (SEQ ID NO: 2) by another amino acid. In a particularly preferred embodiment, proline at position 61 of human NGF is substituted by serine. Proline 61 (P61) corresponds to P182 in SEQ ID NO: 1 (asterisk in FIG. 15 A and FIG. 15 C). Thus, "position 61" in this context refers to position 61 of SEQ ID NO: 2, or to the respective position in a non-human NGF or a mutein of NGF. A respective position, in a non-human NGF or a mutein of NGF, can be determined by aligning the amino acid sequence of the non-human NGF or mutein of NGF with standard tools for pairwise sequence alignment and/or search, such as e.g. BLAST of ClustalW.

Preferably, the mutein of NGF which is distinguishable from the respective endogenous NGF is distinguishable in assays involving an immunoreactive molecule, but essentially indistinguishable regarding the biological activity. For example, it has been described in WO 2008/006893 A1 that murine NGF (mNGF) bears a serine residue at the position corresponding to the proline residue 61 of wild type human NGF (hNGF), and that, in a TFI proliferation assay, hNGF and hNGF-61 dose/response curves were substantially super-imposable. In line therewith, a mutein of human NGF characterized by the absence of proline 61 is a preferred mutein in all aspects of the present invention. A mutein characterized by the absence of proline 61 may or may not be characterized by at least one further mutation, with respect to respective wild type NGF (e.g. human NGF).

In preferred embodiments, the mutein according to the present invention is not associated with undesired immune reactions. Whether a mutein is associated with undesired immune reactions can be tested in vivo, e.g. in animals, including humanized rodents, but it can also be predicted, using tools available to the skilled person, e.g. online, and according to the scientific literature (see e.g. Mai et al., 2015, PLoS One, vol. 10(8): e0135861).

Preferably, the mutein is a mutein of human NGF (hNGF) and is characterized by at least one mutation of the amino acid sequence, which is associated with reduced nociceptive activity, compared to wild-type human NGF (SEQ ID NO: 2), i.e. reduced pain perception, particularly in a mammal, such as a mouse and/or a human, when administered so said mammal. As the p75 receptor is known to be involved in nociceptive activity mediated by NGF, it is preferable that the mutein of human NGF further comprises at least one mutation, preferably at least one amino acid substitution, leading to a reduced interaction of the mutein with the p75 receptor. More preferably the mutation, preferably amino acid substitution, is at any of positions 95-101.

Such mutation may be present in combination with any other feature described herein, including a mutein that can be distinguished from a wild-type NGF, e.g. by an immune reactive molecule, by virtue of a specific antigen which is not found in wild type NGF.

For example, a mutation in hNGF at position 100, with reference to SEQ ID NO: 2 (Arg→Trp, R100W), has been associated with syndromes of pain insensitivity by a genetic analysis (CIPA, Einarsdottir et al, 2004, Human Mol Genet. Vol. 13, p. 799). Thus, generally the mutein preferred in the aspects of the present invention is a mutein of human NGF further comprising at least one amino acid substitution able to substantially reduce its nociceptive activity. In general, the nociceptive activity of NGF or a mutein thereof may be tested as described in WO 2008/006893 A1, applying a concentration of NGF (or mutein thereof) known to be able to induce pain following stimulation ("allodynia"), in the case of NGF, based on a protocol initially described by (Hao et al., 2000, Neurosci. Lett. 286, p. 208-212. Arg100 of wild-type hNGF corresponds to R221 in SEQ ID NO: 1 (+symbol in FIG. 15 A and FIG. 15 C). A preferred mutein of NGF according to the present invention is a mutein of the polypeptide of SEQ ID NO: 2, under the proviso that the mutein is characterized by at least one mutation, preferably amino acid substitution, at any of positions 95-101 of SEQ ID NO: 2.

Preferably, the mutein is characterized by a mutation at position 100, with respect to SEQ ID NO: 2. The term "mutation at position 100, with respect to SEQ ID NO: 2" means that the respective mutein differs at at least one of said positions from the polypeptide of SEQ ID NO: 2. In other words, the mutein is preferably characterized by the absence of an arginine residue at the which corresponds to position 100 of SEQ ID NO: 2. Most preferably, said absence of the arginine residue is a substitution of the arginine residue by another amino acid residue. Unless the context dictates otherwise, "arginine in position 100" refers to the arginine (R) at position 100 of SEQ ID NO: 2.

Thus, most preferably the amino acid substitution is that of the arginine in position 100, even more preferably the amino acid substitution of the arginine in position 100 is with an acidic amino acid or tryptophan. Preferably, said mutein is characterized by substitution of the arginine in position 100. Even more preferably, the amino acid substituting arginine at position 100 is selected from the acidic amino acids glutamic acid or aspartic acid. Most preferably, arginine at position 100 of hNGF is substituted by glutamic acid. In an alternative embodiment the amino acid substitution is that of the glutamine in position 96. In an alternative embodiment the amino acid substitution is that of the tryptophan in position 99. In an alternative embodiment the amino acid substitution is that of the phenylalanine in position 101.

Thus, "position 100" in this context refers to position 100 of SEQ ID NO: 2, or to the respective position in a non-human NGF or a mutein of NGF. A respective position, in a non-human NGF or a mutein of NGF, can be determined by aligning the amino acid sequence of the non-human NGF or mutein of NGF with standard tools for pairwise sequence alignment and/or search, such as e.g. BLAST of ClustalW. Likewise, "position 95-101" in this context refers to the position with the respective residue number, counted beginning at the N-terminus of SEQ ID NO: 2, or to the respective position in a non-human NGF or a mutein of NGF. The respective position is a position corresponding to any one of positions 95-101 of human NGF; such position in a non-human NGF or a mutein of NGF can be identified by such standard tools for pairwise sequence alignment and/or search, in any non-human NGF or mutein of NGF.

More preferably, the mutein is characterized by mutein has more than 50%, preferably more than 60%, more preferably more than 70%, more preferably more than 80%, even more preferably more than 90%, and most preferably more than 95% sequence identity with the wild type NGF (reference NGF) of SEQ ID NO, 2, under the proviso that the mutein is characterized by at least one mutation, preferably amino acid substitution, at any of positions 95-101 of SEQ ID NO: 2. In particular embodiments, said mutein has more than 90% sequence identity with wild type NGF characterized by SEQ ID NO: 2.

Most preferably, the mutein is characterized both by both (i) the absence of proline at position 61 (with reference to SEQ ID NO: 2) and (ii) at least one mutation, preferably amino acid substitution, at any of positions 95-101. A particularly preferred mutein is a mutein of human NGF characterized by the substitutions P61S R100E (termed "NGF P61S R100E"). According to preliminary findings, this mutein is supposed to result in a reduced pain perception as compared to the wild type NGF (Malerba et al. PLOS One, 2015, vol. 10, e0136425).

In preferred embodiments, the mature part of the precursor of NGF contains an even number of cysteine (C) residues, most preferably six cysteine residues, as in SEQ ID NO: 2.

Although the present invention solves difficulties associated with prior art processes (although not recognized by the prior art but rather only when arriving at the present invention, see Example 4), the process of the present invention is combinable also with approaches for increasing the protease cleavage specificity, such as those described by US 2018/0086805 A1 and WO 2013/092776 A1. In particular, the present invention is also applicable to those variants of precursors of NGF and muteins thereof, NGF wherein the original Furin cleavage site of a precursor of NGF ($R^1S^2K^3R^4$, corresponding to positions 118-121 of SEQ ID NO: 1) has been mutated. Preferred mutations are those wherein one or both of ($R^1$ and/or $K^3$ have been substituted by a non-basic amino acid or by histidine, and preferably those wherein $R^4$ (corresponding to position 121 of SEQ ID NO: 1) is the only basic amino acid residue at the position corresponding to the Furin cleavage site in wild type pro-NGF. The term "non-basic amino acid" refers to any amino acid which is not positively charged. The term refers to an amino acid residue other than a basic amino acid. The term excludes amino acids Lysine or Arginine which are amino acids with positively charged side chains. Non-basic amino acids are negatively charged amino acids (Glutamic Acid and Aspartic Acid), amino acids with polar uncharged side chains (Serine, Threonine, Asparagine, Glutamine), amino acids with hydrophobic side chains (Alanine, Valine, Isoleucine, Leucine, Methionine, Phenylalanine, Tyrosine, Tryptophan) and amino acids Cysteine, Glycine and Proline.

Having said that, however, the Furin cleavage site in the precursor of NGF or a mutein thereof (corresponding to positions 118-121 of SEQ ID NO: 1), to be obtained in the present invention, is preferably present, i.e. not altered. For example, in such embodiments, $R^1$ and $K^3$, respectively, are not replaced by other amino acid residues. This could be associated with less regulatory concerns, in certain countries, compared to a method described in the prior art, wherein the original Furin cleavage site of a pro-NGF variant $R^1S^2K^3R^4$ (corresponding to positions 118-121 of SEQ ID NO: 1) has been mutated into $V^1S^2A^3R^4$ ("VSAR method"). Although in that method, trypsin has been described to be capable of cleaving specifically only C-terminally of $R^4$; the present inventors surprisingly found that the production of NGF, and more particular, of muteins thereof as preferred herein, is associated with a further impurity, the des-nona degradation product (see Example 4), which results from a cleavage within the mature portion of NGF (mutein), and which can, therefore, not be prevented by the VSAR method, whether used or not. In contrast, the present inventors have found a process for purification of NGF and muteins thereof, and related aspects, which overcome the shortcomings of the state of the art, including those of the VSAR method.

In the context of the present disclosure, the term "charge variant", with reference to NGF or a mutein thereof, generally refers to a polypeptide comprising at least a part of the amino acid sequence of mature NGF or mutein thereof, and not the entire amino acid sequence of the pro-peptide of NGF or mutein thereof, wherein said polypeptide has, at pH 7.0, a net charge different from said NGF or mutein thereof. Examples of charge variants include those polypeptides which have at least one additional positively or negatively charged amino acid residue, compared to the NGF or mutein thereof, or which lack at least one positively or negatively charged amino acid residue, compared to the NGF or mutein thereof; such charge variants are obtainable e.g. by proteolytic cleavage of a precursor of NGF or mutein thereof at a peptide bond other than the peptide bond that corresponds to the peptide bind between amino acid positions 121 and 122 of SEQ ID NO: 2 (i.e. the native Furin cleavage site). In such examples, typical charge variants include the des-nona variant obtainable by tryptic cleavage C-terminally of residue 9 of SEQ ID NO: 2, as described in the present invention, as well as by undesired cleavage in the (wild-type) pro-peptide of the precursor of NGF, as described for example by WO 2013/092776 A1. In general, charge variants can be separated from the desired NGF or mutein thereof, e.g. for analytical purposes, by chromatography, such as cation chromatography, for illustration see e.g. FIG. 13. As the goal of the various aspects of the present invention is a pure NGF or mutein thereof, the presence of any one or more charge variant(s) in a preparation comprising NGF or mutein thereof is undesired; therefore, any charge variant(s), in the context of the present invention, may also be considered as impurity/impurities.

Nucleic Acids

Nucleic acid molecules encoding the mutein according to the present invention can be generated by standard methods, such as those described e.g. in Current Protocols in Molecular Biology; Eds., F. M. Ausubel et al., Eds., John Wiley Sons: New York, NY 1989. For illustration, and merely to provide a non-limiting example, when it is desired to obtain a mutein, characterized by a specific amino acid sequence, from a recombinant source, a nucleic acid sequence encoding the respective mutein may be generated, e.g. by site-directed mutagenesis and/or by gene synthesis, and the respective nucleic acid sequence may be cloned into a cloning vector. A vector comprising said nucleic acid sequence may then be introduced into a host cell for production of the respective mutein. Specific examples of cloning of NGF muteins are also described in WO 2008/006893 A1 and Malerba et al. PLOS One, 2015, vol. 10, e0136425.

In some embodiments the nucleic acid encoding the mutein according to the present invention is codon-optimized for expression in the desired host cell, such as in a prokaryote, particularly *E. coli*. It will be appreciated that a number of nucleic acids can encode a polypeptide having a particular amino acid sequence. The degeneracy of the genetic code is well known to the person skilled in the art; i.e., for many amino acids, there is more than one nucleotide triplet that serves as the codon for the amino acid. For example, codons in the coding sequence for a given NGF mutein polypeptide can be modified such that optimal expression in a particular species (e.g., *E. coli* or other specific bacterium) is obtained, using appropriate codon bias tables for that species.

Homologous nucleic acid sequences may also be used in the present invention. Hybridization can be used to assess homology between two nucleic acid sequences. A nucleic acid sequence described herein, or a fragment or variant thereof, can be used as a hybridization probe according to standard hybridization techniques. The hybridization of a probe of interest (e.g., a labelled probe) to DNA or RNA from a test source is an indication of the presence of DNA or RNA corresponding to the probe in the test source. Hybridization conditions are known to the person skilled in the art, and can be found in Current Protocols in Molecular Biology, John Wiley & Sons, N.Y., 6.3.1-6.3.6, 1991. Moderate hybridization conditions are defined as equivalent to hybridization in 2× sodium chloride/sodium citrate (SSC) at 30° C., followed by a wash in 1×SSC, 0.1% SDS at 50° C. Highly stringent conditions are defined as equivalent to hybridization in 6× sodium chloride/sodium citrate (SSC) at 45° C., followed by a wash in 0.2×SSC, 0.1% SDS at 65° C.

Process for Production of Nerve Growth Factor (NGF) or a Mutein Thereof

Although certain methods for the production of NGF (e.g. WO2013092776 A1) and of muteins of NGF (e.g. Malerba et al., 2015, PLOS One, vol. 10, e0136425) have been previously described, the present inventors discovered, surprisingly, that previously published processes are insufficient for obtaining the respective protein at high purity. As a solution to these insufficiencies, the present inventors arrived at a new process and related aspects, as described in detail herein.

Thus, in a first aspect, the present invention relates to a process for production of nerve growth factor (NGF) or a mutein thereof.

The process for production of nerve growth factor (NGF) or a mutein thereof according to the first aspect of the present invention preferably comprises the following steps:

(a) obtaining a precursor of NGF or of the mutein thereof,
(d) purification, and the purification in step (d) typically comprises purification on a mixed mode stationary phase. The term "on mixed mode stationary phase" is to be understood broadly and means that a mixture comprising NGF or precursor thereof, together with other molecular species, is exposed to a mixed mode stationary phase, e.g. by chromatography or other suitable process step. Indeed, preferably a mixture comprising NGF or precursor thereof, together with other molecular species, is subjected to chromatography, so that the purification in step (d) comprises purification by mixed mode chromatography.

Purification, in the broadest sense, according to the present invention, means that the NGF or mutein thereof is at least partially separated from other molecular species, including other proteins, such as host cell proteins, precursor and/or degradation products. As a result NGF or mutein thereof which is at least partially purified is obtainable. While the other molecular species may be optionally discarded or not, the NGF or mutein thereof is preferably obtained and retained as a result of the purification.

Preferably, the mixed mode chromatography comprises the use of a stationary phase having a charged group, preferably negatively charged group, and an aromatic group and/or a hydrophobic group.

Each of these steps may itself comprise several actions, which, for simplicity, can also be referred to as steps. For illustration, and as detailed below, step (d) may comprise more than one purification step, e.g. on more than one stationary phase.

Any letter or number used herein in relation to one or more process steps, such as e.g. (a), (b), (c), (d), (d1), (d2), is not to be understood as limiting, but rather for reference. It should not be understood that the sequence of events in the process or use according to the present invention may be limited by alphabetical sequence of letters or the numerical sequence of numbers. Notwithstanding the foregoing, it is strongly preferred that the sequence of events in the process or use according to the present invention is a sequence described herein.

Additional aspects of the mixed mode chromatography, particularly suitable stationary phases, will be described in some more detail below, but these aspects are generally applicable to the present invention. Thus, in particular all those stationary phases, including all embodiments thereof, that are described below to be particularly useful for the mixed mode chromatography in step (d2) are generally useful for the purification of NGF or a mutein thereof according to the present invention, and can be used in all types of embodiments, such as in combination with a step of (d1) capturing chromatography or without. Indeed, Example 2B describes that some advantages can be achieved by using mixed mode chromatography in a variation of a protocol according to the state of the art. Additional improvements can be achieved when the mixed mode chromatography is combined with further improvements and embodiments according to the present invention, such as those exemplified in Examples 5 and 7.

It is also preferred in the process according to the present invention that the precursor of NGF or a mutein thereof is subjected to a step of (c) exposure to a protease.

Said exposure is typically carried out prior to step (d).

"exposure to a protease", unless specified otherwise, means that a precursor of NGF or a mutein thereof is exposed to a protease. For that purpose a protease and the precursor of NGF or a mutein thereof are usually jointly present, e.g. in a liquid. For example, a protease may be added to a liquid comprising the precursor of NGF or a mutein thereof.

It is also preferred that the process according to the present invention comprises a step of (b) re-folding Said re-folding is preferably carried out prior to step (c). Thus, the process of the present invention is preferably characterized in that no chromatographic purification is performed prior to the exposure to protease.

Preferably the process according to the present invention is a process for production of a mutein of human NGF.

According to the present invention, NGF or a mutein thereof is produced as a polypeptide comprising a pro-peptide and the mature portion. In other words, a respective precursor may be described as a fusion protein, characterized by said NGF or a mutein thereof and by a prosequence (pre-peptide); unless specified otherwise, in the fusion protein the pre-peptide is normally found N-terminally of the NGF or a mutein thereof. Said fusion protein corresponds to (in the case of NGF) or resembles (in the case of a NGF mutein) the production of NGF in mammalian cells in vivo. According to the present invention, therefore, the precursor of NGF or mutein thereof has to be subjected to cleavage by a protease, e.g. by limited proteolysis. According to the present invention, the NGF or mutein thereof also has to be purified. Thereby, the NGF or mutein thereof is separated from the respective pre-peptide, from potentially truncated forms of NGF or mutein thereof, from the protease, and from impurities, such as host cell proteins (HCP) and other impurities.

In one embodiment, the entire process described herein is carried out without animal-derived reagents and materials. In one embodiment, the process of the present invention is carried out under good manufacturing practice (GMP). For example, the use of certified animal-free reagents and materials is typically considered important for GMP-compliance of the process.

In one embodiment, the process described herein, following culture of a host cell, is carried out partially or completely at a temperature of 15° C. or less, preferably 0 to 10° C., for example 4 to 8° C. For that purposes, respective process steps may be carried out in a cold room, with respectively pre-cooled material and ingredients (e.g. pre-cooled chromatography columns and pre-cooled buffers and other reagents).

The steps of the process of the present invention shall now be described in detail. However, variations of the steps explicitly described are also possible.

(a) Obtaining a Precursor of NGF or a Mutein Thereof

An aspect of the present invention provides a process for purifying NGF or a mutein thereof, optionally from a host cell culture, wherein a fraction of said host cell culture comprising a precursor of NGF or a mutein thereof is obtained, exposed to protease and purified, as described herein.

Thus, the process of the present invention comprises a step (a) of obtaining a precursor of NGF or a mutein thereof. Preferred muteins are those described herein. Preferably the precursor of NGF or mutein thereof is obtained at a degree of purity wherein the NGF or mutein thereof is substantially free of impurities, such as host cell proteins, as further described below.

Precursors of NGF or of muteins thereof, particularly human pro-NGF, is available commercially. Thus, in one embodiment, the step (a) of obtaining comprises or consists of acquiring a precursors of NGF or mutein thereof from a commercial supplier. However, in preferred embodiments, the precursor of NGF or mutein thereof is produced as part of the process of the present invention. Protein synthesis and isolation from an organism are options, but the most preferred embodiment is the expression in a host cell, most preferably recombinant expression.

A preferred precursor of NGF is pro-NGF, and preferred precursors of muteins are those that comprise the pro-peptide of wild-type NGF, such as wild-type human NGF, or a variant thereof. A variant typically has, in the amino acid sequence N-terminal to the first amino acid residue of the NGF mutein, more than 60% amino acid identity, such as more than 70% amino acid identity, such as more than 80% amino acid identity, such as more than 90% amino acid identity, with the pro-peptide of NGF.

In one embodiment, the precursor of NGF obtained, or of a respective mutein obtained, for the process of the present invention, does comprise the most C-terminal residues of SEQ ID NO: 1 (RA), or a respective C-terminal peptide, e.g.

dipeptide. Such C-terminal peptide can be identified, in non-human NGF or a mutein of any NGF, by aligning the amino acid sequence of said non-human NGF or a mutein of any NGF with SEQ ID NO: 1, e.g. in a pairwise sequence alignment as generally mentioned above. Without wishing to be bound to any particular theory, it is envisaged that in some embodiments the C-terminal dipeptide, is proteolytically cleavable, so that the polypeptide obtained by such cleavage ends with the most C-terminal amino acid residue of mature NGF.

Preferably, however, in an embodiment the most C-terminal amino acid residue of said precursor consists of the most C-terminal amino acid residue of NGF. Thus, in such embodiment, which is much preferred, the precursor of NGF does not comprise the most C-terminal residues of SEQ ID NO: 1 (RA), or a respective C-terminal peptide, e.g. dipeptide. Such a precursor typically ends with the most C-terminal amino acid residue of mature NGF (which is illustrated, by means of example, as the most C-terminal amino acid residue of SEQ ID NO: 2.

An alternative preferred precursor of NGF is pre-pro-NGF, preferably, however, in an embodiment wherein the most C-terminal amino acid residue of said precursor consists of the most C-terminal amino acid residue of NGF. These preferred embodiments are associated with the advantage that no proteolytic cleavage at the C-terminus of the precursor is necessary in order to obtain NGF from the precursor in the context of the present invention. Variants of pro-NGF and of pre-pro-NGF are alternative preferred precursors in the present invention, preferably, however, in an embodiment wherein the most C-terminal amino acid residue of said precursor consists of the most C-terminal amino acid residue of NGF. Preferred precursors of NGF muteins, in this embodiment, are those that comprise the pre-pro-peptide of wild-type NGF, such as wild-type human NGF, or a variant thereof. A variant typically has, in the amino acid sequence N-terminal to the first amino acid residue of the NGF mutein, more than 60% amino acid identity, such as more than 70% amino acid identity, such as more than 80% amino acid identity, such as more than 90% amino acid identity, with the pre-pro-peptide of NGF.

In general, although the step of obtaining precursor of NGF or a mutein thereof can comprise an in vivo step, the present invention does not contemplate an invasion of the human or animal body. Rather, the precursor of NGF or a mutein thereof is typically, according to the present invention, obtained by recombinant expression in a host cell.

Preferably the precursor of NGF or mutein thereof is encoded by the nucleic acid comprised in the host cell by an inducible promoter, so that production of the precursor of NGF or mutein thereof can be induced when desired. In general, generic induction schemes known in the art are suitable for induction of the production.

A precursor of NGF or a mutein thereof is preferably obtainable from recombinant sources, i.e. by recombinant expression.

To that end, a host cell into which a nucleic acid comprising an open reading frame encoding a precursor of NGF or a mutein thereof has been introduced, is cultivated. Thus, preferably the recombinant expression is in a host cell. The term "host cell" is not particularly limited and can refer to any cell which is suitable for recombinant production of a polypeptide encoded by a nucleic acid present in the host cell or introduced into the host cell. Said nucleic acid encodes at least a polypeptide or protein of interest, preferably a precursor of NGF or a mutein thereof. Preferably the host cell is a cell capable of multiplication or clonal expansion. The term "host cells" comprises according to the invention prokaryotic and eukaryotic cells, wherein prokaryotic cells (e.g. *E. coli*) are preferred. A nucleic acid may be present in the host cell in the form of a single copy or of two or more copies and, in one embodiment, is expressed in the host cell.

The open reading frame encoding a precursor of NGF or a mutein thereof may or may not be codon-optimized for expression in the host cell, but preferably is codon-optimized.

Suitable host cells can be selected from prokaryotic and eukaryotic host cells, although prokaryotic host cells are preferred in typical embodiments. In some embodiments, the precursor of NGF or mutein thereof is obtained by recombinant expression in a host cell, more preferably in a bacterial host cell. Gram-negative bacteria are preferred, most preferably *Escherichia coli* (*E. coli*). Preferred prokaryotic host cells include *E. coli*, preferably *E. coli* Rosetta (DE3). More preferably, the precursor of NGF or a mutein thereof is obtained in a conformation other than the native conformation and/or in aggregates, most preferably in inclusion bodies.

Methods of fermentation of respective host cells and of production of desired proteins or polypeptides are known to the person skilled in the art. According to the present invention, any type of recombinant expression is comprised, but particularly preferred are those types wherein the precursor of NGF or a mutein thereof is obtained as insoluble protein, e.g. in the form of inclusion bodies.

The cultivation of the host cell, e.g. in production scale, can also be referred to as fermentation. In general, generic fermentation schemes and protocols are suitable for cultivation of the host cell. For example, a fed-batch scheme was used successfully by the present inventors (see Examples), and others can reasonably be assumed to work as well. It is possible that the yield may differ to some extent depending on the individual cultivation conditions, however, the precursor of NGF or mutein thereof as such can be obtained over a wide range of conditions, and when it is obtained, it can be used in the present invention as herein described.

Preferably, the host cell is a cell that can be cultivated in suspension; such cells include bacteria such as *E. coli*, yeasts such as *S. cerevisiae*, and mammalian and insect suspension cell lines. Most preferably the host cell is *E. coli*. Any strain of *E. coli* may be used, preferred are however strains of *E. coli* which are suitable for protein production. For example, strains designed to enhance the expression of eukaryotic proteins that contain codons rarely used in *E. coli*, such as e.g. Rosetta BL21 (Merck Novagen) and others are suitable. It is less preferred to use host cells that have been designed for oxidative folding in the cytosol, such as *E. coli* Origami (Merck Novagen) and others. Since the process and use of the present invention are adapted also to provide for efficiently folded NGF or mutein thereof, at a time point after expression of the precursor of NGF or mutein thereof, the correct folding inside the host cell is not required, and in many embodiments not desired. For Gram-negative bacterial host cells, in particular *E. coli*, cytoplasmic expression is preferred over periplasmic expression. Cytoplasmic expression, in general, can be achieved when the precursor of NGF or a mutein thereof does not encode a pre-peptide that would be suitable to direct translocation across the cell membrane.

Preferably, the host cell produces the precursor of NGF or mutein thereof in the cytoplasm. Thus, preferably, the precursor of NGF or mutein thereof is produced in the cytoplasm of the host cell. In an alternative, less preferred embodiment, the precursor of NGF or mutein thereof is produced in the periplasm of a Gram-negative bacterium. Indeed, it is one advantage of the present invention that cytoplasmically expressed precursor of NGF or mutein thereof, which is understood to be not properly folded, can nevertheless be folded and purified efficiently, by the process of the present invention. Thus, the folding and processing occurs post-translationally, i.e. in a separate step after the completion of translation.

For fermentation, the cell in a host cell, more preferably bacterial host cell, and most preferably E. coli, is cultivated in a growth medium, and optionally but preferably, production of the precursor of NGF or mutein thereof is induced. Fermentation may be carried out in a complex growth medium or in a chemically defined growth medium ("minimal medium"), or in a medium that comprises both complex and chemically defined constituents. In preferred embodiments, fermentation is carried out in an animal-component free medium. A "complex medium", or a "complex constituent" refers to a growth medium, or a medium constituent (ingredient), respectively, which is not defined by its chemical constituents. Typical complex constituents are obtained, typically without purification, from natural sources. For example, yeast extract and hydrolysates (e.g. tryptic) of certain proteins (e.g. casein) are considered complex constituents. A medium comprising at least one complex constituent is considered a "complex medium".

Optionally fermentation is carried out in a batch process. More preferably, fermentation is carried out in a fed-batch process. A fed-batch is typically characterized in that, at one or more defined time intervals and/or at one or more defined growth states of the host cell culture, a batch ingredient, typically in the form of a liquid ("batch solution"), is added ("fed") to the growth medium. Preferred batch solutions have a total amount of fermentable carbon sources (e.g. total of glucose, sucrose) which is higher than the total amount of fermentable carbon sources of the growth medium.

Particularly for the fermentation of E. coli host cells, but not necessarily limited to the fermentation of E. coli host cells, unless the context dictates otherwise, the following considerations apply: While a complex medium may, in general, promote high specific growth rates, the associated overflow metabolism of E. coli cells might result in formation of toxic side-products (e.g. acetate), whose accumulation in the culture will prevent generation of high cell densities. Also, complex constituents of the feed-solution make it difficult to adjust a defined growth rate within the fed-batch phase of the upstream process and thus, impair the process control. Another obstacle associated with undefined constituents may be their potential batch-to-batch variability and the associated problems to establish a robust and reproducible fermentation process. Therefore, a chemically defined, animal-component free medium composition would be favored for development of a high cell density fed-batch process.

On the other hand, a given bacterial (e.g. E. coli) production strain might require a certain medium additive to facilitate suitable expression yields. Although, such potential additive might be identified through medium-optimization, the use of a complex medium, or at least supplementation (of a chemically defined medium and/or chemically defined fed solution) with a complex constituent, may be selected. In some embodiments, this can be associated with high expression.

Optionally the cultivation of the host cell is carried out in the presence or absence of one or more selective agents, such as antibiotics. For fermentation, the host cell in a host cell, more preferably bacterial host cell, and most preferably E. coli, is cultivated in a growth medium comprising or not comprising antibiotics, depending on the circumstances. Optionally also the fed solution comprises antibiotics. Suitable antibiotics are chosen by the skilled person based on the antibiotic resistance of the host cell; such antibiotic resistance may be conferred by one or more plasmids comprised by the host cell. For illustration, Ampicillin and Chloramphenicol are suitable antibiotics for the host cell of Example 1. Preferably, however, e.g. particularly for large-scale production, supplementation of the growth medium and of the fed solution, if applicable, by antibiotics is not desirable. Moreover, the use of a ß-lactam derivative (i.e. Ampicillin) for production of a drug substance may not be considered acceptable by regulatory authorities.

Optionally but preferably, production of NGF or a mutein thereof, as encoded by the host cell, is inducible. Methods and tools for inducible protein production in host cells are known to the skilled person. For example, as illustrated in the Examples herein, inducible expression by a promoter responsive to Isopropyl-β-D-thiogalactopyranoside (IPTG), which may suitably be added for induction of expression, is suitable, e.g. in bacterial host cells, such as E. coli.

Expression is usually carried out for several hours, or even several days, and preferably at any rate preferably until inclusion bodies are present in the host cell. The presence of inclusion bodies, e.g. in E. coli, can be tested by standard methods.

The amount of precursor of NGF or mutein thereof obtained in the context of the present invention is not particularly limited, and may be, for example, in the range from micrograms up to kilograms.

The purification of the expressed proteins from inclusion bodies usually require two main steps, each optionally divided in sub-steps: the two main steps consist of (1) extraction of inclusion bodies from the host cell (preferably a bacterium), and (2) solubilization of the extracted inclusion bodies.

(1) Preferably, the extraction of inclusion bodies from the host cell is done by standard methods or variations thereof. For that purpose, the cell membrane and/or cell wall of the host cell has to be disrupted. Particularly preferred for that purpose is high-pressure homogenization. The pressure is not particularly limited and may be chosen inter alia in consideration of the type of host cell, based on the standard practice in the art. The inclusion bodies are obtained as part of the fraction comprising the insoluble material obtainable by disruption of the cell membrane and/or cell wall of the host cell. Optionally but preferably said fraction is washed after disruption. To that end, said fraction may for example be resuspended in an aqueous solution (wash solution), such as a buffered solution, at conditions at which the inclusion bodies are not solubilized. Such a wash solution may comprise a detergent, e.g. Triton-X-100 or Tween-20 or others. Some cell debris, such as e.g. cell membrane fragments, may be removed quite efficiently in the presence of such detergent. The inclusion bodies are separated from the wash solution, e.g. by centrifugation, and the wash solution is discarded. Optionally, the wash process is repeated, with an identical or different wash solution. Such a same, or preferably different, wash solution may also comprise chaotropic agent, at least to some extent, however not at concentrations sufficiently high to solubilize the precursor of NGF or mutein thereof—suitable concentrations of chaotropic agent can be tested experimentally at pilot scale, and then applied.

(2) Preferably, the solubilization of the inclusion bodies is done by standard methods or variations thereof. The solubilization of the inclusion bodies is not particularly limited, as long as the precursor of NGF or mutein thereof is solubilized, or solubilized at least to some extent. Typically, solubilization occurs by addition of a liquid which favors the solubilization of the precursor of NGF or mutein thereof ("solubilization liquid"). Typically, the solubilization liquid comprises at least one chaotropic agent and/or at least one detergent. More preferably, the solubilization liquid comprises both at least one chaotropic agent and at least one detergent. Preferred chaotropic agents are urea and or guanidinium and salts and derivatives thereof, such as in particular guanidinium HCl. For chaotropic agents, high concentrations near at orjust below the limit of solubility are normally preferred. For example, if guanidinium (or guanidinium HCl) is used as the only chaotropic agent, the concentration of guanidinium in the solubilization liquid is preferably at least 4 mol/l, more preferably at least 5 mol/l, such as in particular 6 mol/l. For example, if urea is used as the only chaotropic agent, the concentration of urea in the solubilization liquid is preferably at least 4 mol/l, more preferably at least 5 mol/l, more preferably at least 6 mol/l, more preferably at least 7 mol/l, such as in particular 8 mol/l. The present inventors found that it is particular advantageous to solubilize the precursor of NGF or mutein thereof at conditions wherein at least two chaotropic agents are present in the solubilization liquid, for example at conditions wherein both guanidinium (HCl) and urea are present. This is associated with the advantage that the total amount of all chaotropic agent is not limited by the solubility barrier of an individual chaotropic agent. For example, the present inventors found that solubilization is particularly advantageous in the presence of both guanidinium (HCl) and urea. Thus, in a preferred embodiment, the solubilization liquid comprises both guanidinium (HCl) and urea. In that embodiment, the concentrations of each of these chaotropic agents are selected such that both chaotropic agents together are still soluble. For example, a solubilization liquid comprising 6 mol/l guanidinium (HCL) and 2 mol/l urea was used successfully, and is indeed much preferred in the present invention. Other combinations of solubilities are equally possible, e.g. combinations comprising less than 6 M guanidinium (HCl) and more than 2 mol/l urea, as long as both these chaotropic agents are fully solubilized in the solubilization liquid. The solubilization liquid is typically aqueous. The detergent present in the solubilization liquid, if any, is not particularly limited, and any detergent known in the art for such purpose or otherwise suitable for such purpose, such as without limitation, Triton-X100, may be used. Solubilization may be favored, in some embodiments, by mechanical movement (shaking, stirring or the like).

Following solubilization, the liquid mixture comprising the solubilized precursor of NGF or mutein thereof can be subjected to subsequent steps of the process. Preferably the liquid mixture comprising the solubilized precursor of NGF or mutein thereof is subsequently subjected to step (b) as described in detail below. In case the precursor of NGF or mutein thereof is solubilized to some extent only, any non-solubilized inclusion bodies may be subjected again to addition of a liquid which favors the solubilization of the precursor of NGF or mutein thereof. At any rate, preferably, the solubilization of the extracted inclusion bodies is done by standard methods or variations thereof. Such methods have been described in the art, generally and specifically, see e.g. Yang et al., 2011, PLoS One, vol. 6, e22981.

Indeed, it is preferred that the precursor of NGF or of a mutein thereof is obtained in a solution, i.e. in soluble form. In typical embodiments this is the case when the precursor of NGF or of a mutein thereof initially comprised in inclusion bodies has been brought into a solution, e.g. by the addition of a solubilization liquid, as above-described.

(b) Re-Folding

Preferably the process of the present invention comprises a step (b) of (re-)folding the NGF or mutein thereof. This step is an optional step, but it is preferably included. In particular, the step (b) of (re-)folding the NGF or mutein thereof is normally included in those cases where the precursor of NGF has been obtained, in step (a), in a non-properly folded form. Without wishing to be bound to any particular theory, it is understood that a precursor of NGF or mutein thereof in inclusion bodies is not properly folded. Indeed, in particular when the precursor of NGF has been obtained, in step (a), in inclusion bodies, the process of the present invention typically comprises the step (b) of (re-)folding the NGF or mutein thereof. Preferred muteins are those described herein.

When it is said herein that the precursor of NGF or mutein thereof is subjected to (re-)folding and also when it is said that NGF or mutein thereof is subjected to (re-)folding, it is intended in both cases to mean that (at least) the mature part of the NGF or mutein thereof adopts the native conformation. Both these expressions neither specifically exclude that also the section of the precursor of NGF or mutein thereof, which is not part of the mature part, is folded, nor do these expressions require the folding thereof. Without wishing to be bound to a particular theory it can be assumed that the pro-peptide of NGF has a beneficial function to the (re-)folding of NGF or a mutein thereof, but the present invention is not limited to such theoretical concept.

The term "(re-)folding" as used herein is applicable to bringing the NGF or mutein thereof into the native conformation (of NGF or of the mutein thereof) and does not include any implications on whether or not the precursor of NGF or mutein thereof had been correctly folded at a stage prior to solubilizing in the solubilization solution of step (a) or not. Without wishing to be bound to any particular theory, it is generally assumed that the native conformation of a mutein of NGF will resemble the native conformation of NGF, e.g. in the sense that the peptide backbones of NGF and of a mutein thereof are superimposable, particularly when a mutein is distinguished form NGF by amino acid substitutions only, and even more so, when these amino acid substitutions do not disrupt the 3-dimensional structure of the protein.

Presence of the native conformation of NGF or a mutein thereof can be tested e.g. by presence of the same three disulfide bridges as in the native NGF protein.

Preferably, step (b) follows step (a). Preferably, step (b) precedes step (c). Thus, it is particularly preferred that step (b) follows step (a) and precedes step (c).

In many embodiments, the precursor of NGF or of a mutein thereof obtained in step (a) is obtained in a soluble but not properly folded form. This is, for example, the case when the precursor of NGF or of a mutein thereof is obtained in a solution in the presence of at least one chaotropic agent and/or at least one detergent. The following considerations apply in such cases: while it is welcome that the precursor of NGF or of a mutein thereof is obtained in step (a) in a solution, as opposed to a precipitate, the solubilization described above may have occurred in the presence of one or more agents, such as chaotropic agents and or detergents, often at high concentrations, which are not suited to favor the folding of proteins into a native confirmation. Therefore, the presence of such agents comprised in the solubilization solution, at high concentrations, in particular, is typically not desired. In such case, the precursor of NGF or a mutein thereof is subjected to a change of chemical environment. The type of process by which the change of chemical environment is achieved is not particularly limited, as long as the effect of changing the chemical environment is achieved. Preferred embodiments include buffer exchange over a membrane, in particular dialysis, and dilution. The buffer exchange over a membrane can occur by using a liquid suitable for refolding (the "refolding solution") on the side of the membrane that does not comprise the precursor of NGF or mutein thereof. The membrane is not permeable to the precursor of NGF or mutein thereof. The buffer exchange by dilution can occur by adding a volume excess of a liquid suitable for refolding (the refolding solution") to the solubilization solution comprising the precursor of NGF or mutein thereof. In this context, "excess" preferably refers to the 5-fold to 1000-fold volume, such as the 10-fold to 500-fold volume, the 15-fold to 200-fold volume, the 20-fold to 100-fold volume, the 30-fold to 80-fold volume, the 40-fold to 60-fold volume, and most preferably the about 50-fold volume.

By such type of chemical environment, the agents in the solubilization liquid which are unfavorable to (re-)folding of the precursor of NGF or of a mutein thereof are removed or diluted to concentrations at which they do not typically significantly interfere with the (re-)folding of the precursor of NGF or of a mutein thereof.

The refolding solution is not particularly limited, as long as it is suitable for (re)folding of the precursor of NGF or mutein thereof. For example, several refolding solutions are described by WO 2000/022119 A1 and by Rattenholl, 2001, Dissertation zur Erlangung des akademischen Grades doctor rerum naturalium (Dr. rer. nat.), Martin-Luther-Universität Halle-Wittenberg (Germany), and these can be employed in the present invention.

As a general concept, but without limitation, a suitable refolding solution in the context of the present invention will contain at least one reducing agent and at least one protein structure stabilizing agent. The reducing agent is not particularly limited, but water-soluble agents having one or more free thiol groups, such as $C_1$-$C_6$ alkyl thiols, cysteine, glutathione, are preferable, and among these glutathione is most preferred. The protein structure stabilizing agent is not particularly limited, but amino acids (D and L and racemates, but preferably L), more preferably proteinogenic amino acids, nucleotides and guanidinium group containing compounds, including guanidinium HCl, as well as zwitterionic compounds in general, are preferred; most preferred is the amino acid arginine (D and L and racemates, but preferably L), L-arginine in particular. At any rate, the concentration of chaotropic agent, such as guanidinium HCl, in the refolding solution, if any, is typically at least ten-fold lower than during a preceding step of obtaining the precursor in solubilized form. One way of achieving this, together with efficient refolding, is a buffer exchange or dilution, wherein the concentration of the chaotropic agent is reduced; the at least one reducing agent and at least one protein structure stabilizing agent can then be added. For the avoidance of doubt, in the context of the present disclosure, arginine and other proteinogenic amino acids are not considered as chaotropic agents. Most preferred is a refolding solution comprising arginine and glutathione. Suitable refolding solutions have also been described by Rattenholl, 2001, supra, and by WO 2000/022119 A1.

The at least one reducing agent may preferably be comprised in the refolding solution in both reduced and oxidized form, although the refolding solution is preferably prepared with an excess (molar and/or weight excess) of reduced reducing agent. For example, the refolding solution may be prepared with a 1.5-10 fold weight excess, preferably 2-5 fold weight excess, and most preferably ca. 3-fold weight excess of reduced reducing agent vs. oxidized reducing agent.

Optionally the refolding solution comprises one or more salts, such as sodium chloride, for example.

Preferably, the pH of the refolding solution is neutral to basic, preferably in the range of 7.0 to 11.0, more preferably in the range of 8.0 to 10.5, and most preferably in the range of 9.0 to 10.0, such as about 9.5.

The concentration of precursor of NGF or mutein thereof during the step of refolding, i.e. in the refolding reaction, is typically in the range of 1 to 2000 mg, preferably 10 to 1000 mg, more preferably 50 to 500 mg, even more preferably 100 to 400 mg, and most preferably 200 to 300 mg of precursor of NGF or mutein thereof per liter of refolding reaction. The use of higher concentrations than recommended by the prior art is associated with the advantage of reduced cost, particular but not exclusively when highly pure ingredients are used, such as in good manufacturing practice (GMP), because this allows the refolding of relatively larger amount of precursor of NGF or mutein thereof in a given volume of refolding solution. The advantage is quite remarkable, as some of the preferred ingredients of the refolding solution, such as arginine and glutathione, are normally relatively costly, and thus contribute to the total cost of the production of NGF or mutein thereof.

Preferably the step of refolding is carried out at a temperature between 0° C. and 20° C., more preferably between 2° C. and 10° C., most preferably between 4° C. and 8° C.

By the step of refolding, at least a fraction of the precursor of NGF or mutein thereof is obtained in a correctly folded form. In particular, it is preferred that at least the mature part of the precursor of NGF or mutein thereof in said fraction is obtained in the correctly folded form. Various methods for testing protein folding, such as circular dichroism and others are available and can be routinely used in the present invention. For example, correct (re-)folding of the mature part of the precursor of NGF or mutein thereof can also be indirectly determined by investigating, e.g. in a tryptic digest followed by mass spectrometry, for illustration, the presence of the three specific disulfide bonds as in wild-type folded mature NGF, as known from the literature.

As the precursor of NGF or of a mutein thereof is normally subjected to protease digestion at a step later than step (b), a buffer exchange or buffer adaption following step (b) may be desirable, so that the protease digestion can be carried out at the conditions (pH, salt etc. . . . ) that are chosen for the protease digestion.

However, in one embodiment, the present invention is further characterized in that the steps (b) of (re-)folding the NGF or mutein thereof is carried out, at least in part, simultaneously to the step (c) of exposure the NGF or mutein thereof to protease (which step will be described in detail below). In such embodiment the protease (otherwise described in detail below) is typically added directly to the refolding solution. Unless the protease used is very specific (e.g. Furin) or otherwise well-controlled, e.g. by temperature or buffer conditions, this embodiment is, however, less preferred in comparison with the stepwise process, wherein, the protease digestion is carried out in a separate step, after the step of (re-)folding.

(c) Protease Digestion

In contrast to certain prejudice in the art, based on which periplasmic expression of NGF with respective bacteria, rather than the expression of the respective pro-form in inclusion bodies (e.g. Kurokawa et al., 2001, J. Biol. Chem., vol. 276, p. 14393-14399) was proposed, the present inventors have found that indeed production of NGF or a mutein thereof via a respective precursor is suitable. The precursor is proteolytically cleaved off the NGF or mutein thereof, so that the mature NGF or mutein thereof is obtained. Thus, based on the findings of the present inventors, a protease can be very useful in the preparation of NGF and a mutein thereof, as described herein. The suitability of the protease useful in the present invention also for NGF or mutein thereof at high purity is based, inter alia, on the improvements of the present invention regarding purification of NGF or mutein thereof at the step(s) following the protease digestion.

As shown in the examples, a mutein of NGF, which is by at least one mutation, preferably amino acid substitution, at any of positions 95-101 of SEQ ID NO: 2, is efficiently processed by protease in the process according to the present invention. Also in this regard, the present invention provides an advantage which is surprising in view of the discouraging literature reports on processing of painless NGF, in particular (e.g. Larsson et al., Neurobiol. Dis., 2009, vol. 33, p. 221-228).

Thus, the process of the present invention comprises a step (c) of exposure of the precursor of NGF or mutein thereof to protease. Said step can also be referred to as a step of "proteolytic cleavage", "processing", and the like. During step (c) at least one peptide bond of the precursor of NGF or mutein thereof is cleaved, typically by hydrolysis. By such step, the mature NGF or mutein thereof is obtained. Preferred muteins are those described in the present disclosure.

Based on the prior art, but also in view of the difficulties discovered by the present inventors in the process of arriving at the present invention (see e.g. low stability of purified NGF mutein over time, FIG. 10), it initially appeared that the production of NGF and muteins thereof via expression of the respective pro-form in prokaryotic systems, followed by trypsin digestion and purification, would not represent a reasonable production strategy. Indeed, some prior art had encouraged the recombinant production of NGF by an alternative route, namely in the periplasm of bacteria (e.g. Kurokawa et al., 2001, J. Biol. Chem., vol. 276, p. 14393-14399), which would render the use of a protease (added during the process) dispensable. Further prejudice against the use of a protease in the production of NGF or a mutein thereof may be based on initial findings of the present inventors, in particular the formation of a degradation product after refolding, digestion and purification (for illustration see Example 4). Indeed, while it was known that, due to the proximity of 3 basic amino acid residues within the native Furin cleavage site, trypsin does not cut precisely at the sequence Arg-Ser-Lys-Arg ($R^1S^2K^3R^4$), it had been suggested that this shortcoming could be solved by introducing certain mutations into the pro-NGF sequence (US 2018/0086805 A1, WO 2013/092776 A1). Now, the present inventors identified that the solution proposed by these two publications will not satisfactorily work based on the disclosure of these documents, let alone at preparative scale, since a des-nona degradation product of NGF or a mutein thereof will be formed, putatively by tryptic attack within the mature part of NGF or mutein thereof, and formation of said des-nona degradation product cannot suitably be avoided by removing the amino acid residue which is putatively recognized by the trypsin (residue 130 in SEQ ID NO: 1) since this would, as a consequence, alter the amino acid sequence of mature NGF at position 9. For wild type NGF and most muteins NGF this is not acceptable. Therefore, these early results, described inter alia in Example 2, would normally be considered by the skilled person as discouraging, as it would be expected that potential product-variants obtained by trypsinization may be omitted by alternative periplasmic expression, where residual trypsin, which could affect stability of the product, would not be present.

Despite these prejudices and early indicia against the use of a protease, the present inventors have surprisingly arrived at a reliable process in which protease is used. According to one characteristic of the present invention, the process of producing NGF or a mutein thereof is typically characterized in that no chromatographic purification is performed prior to the exposure to protease. This is associated inter alia with the advantage that high purity of NGF or mutein thereof can be obtained even when the total number of chromatographic steps is three or less, such as most preferably two.

The type of protease is not particularly limited, as long as the protease is a protease capable of cleaving the precursor of NGF or of a mutein thereof in such a manner that mature NGF or a mutein thereof is released, or can be released. "released", in this context, means that mature NGF or a mutein thereof is obtained in a form in which is not bound to the pro-peptide or variant thereof by any covalent bond, particularly not by a peptide bond. In one embodiment, the protease is animal-free. Such a protease is preferably a protease derived from a recombinant source. Use of certified animal-free raw material is considered important for GMP-compliance of the process. Suitable animal-free recombinant sources are for example plant cells, fungal cells and bacterial cells, among which fungal cells are preferred. In particular, protease obtainable from recombinant expression in yeast, such as including but not limited to *Pichia pastoris* or *Saccharomyces cerevisiae*, is preferred.

In one embodiment, said protease is a serine protease. In one embodiment, said protease is a protease capable of cleaving a polypeptide chain C-terminally of an arginine residue and/or N-terminally of a serine residue.

In a preferred embodiment, the protease is associated with high cleavage specificity, specifically N-terminal of serine (S) 122 in SEQ ID NO: 1 or the equivalent most N-terminal amino acid reside of mature NGF or any mutein thereof. Optionally, the protease is capable of cleaving the pro-peptide of NGF, or variant thereof, at one or more internal positions, but this is not required. Rather, what is important is that the protease is capable of cleaving the peptide bond that links the pro-peptide of NGF or mutein thereof to the mature part of NGF or mutein thereof. For illustration, in SEQ ID NO: 1, this corresponds to the peptide bond between residues 121 and 122.

Preferably, the protease used is Trypsin (EC 3.4.21.4). Trypsin is available commercially, e.g. from recombinant sources. The exposure to trypsin can also be referred to as "trypsinization".

In an alternative embodiment the protease is Furin.

Preferably the protease is from a recombinant source (recombinantly expressed). Many proteases from recombinant sources are commercially available, also at high purity. In preferred embodiments, porcine trypsin is preferable, optionally recombinantly expressed.

The term "porcine" is not particularly limited and includes all varieties and races of pork, wild and domesticated, particularly *Sus scrofa* and *Sus scrofa domesticus*. Particularly preferred is, in some embodiments, GMP grade trypsin from Roche (Basel, Switzerland), with the following product number: 06369880103. If needed, the amount of trypsin used may be adapted based on the specific activity of the trypsin batch used and on the guidance of the experimental examples herein.

If trypsin is used for manufacture of NGF or mutein thereof, in the process of the present invention, it should be selected such that undesired cleavage is kept at a minimum and that desired purity requirements are met; such trypsin may be selected according to the following criteria.

In one embodiment, the trypsin has low side-activity: Notably, as is generally known, trypsin can be subjected to autolysis. As is known in the art, autolysis of trypsin may result in so called pseudotrypsin, which has a broadened substrate-spectrum and possesses chymotrypsin-like activity.

Preferably, the trypsin is a so-called "modified trypsin"; such modified trypsin is typically obtained by acylation of trypsin's exposed s-amino groups of lysine residues. Such "modified trypsin" is known for its high sequence specificity, i.e. cleavage exclusively C-terminal of (respectively exposed) arginine and lysine residues.

Preferably the trypsin is "sequencing grade" trypsin. The term "sequencing grade" generally indicates that the respective trypsin is of such purity and specificity that it is recommended for tryptic digest of proteins e.g. for mass spectrometry purposes; "sequencing grade" trypsin is nowadays available from numerous commercial suppliers.

Preferably, the trypsin used is characterized by low batch-to-batch variability, in order to enable a reproducible production process. Alternatively, the chosen enzyme should be delivered with a certificate stating the specific activity of the respective batch. The required amount of enzyme may then be based on activity rather than on mass.

While there is literature indicating that an elevated temperature can have a negative impact on the refolding yield and pro-NGF stability, temperature is also a major parameter for specificity of the trypsinization. It was established in the present invention, however, that the trypsinization is rather robust (Example 2) and that trypsin-related impurities in the final product can be avoided by the improvements of the present invention (Example 5).

Based on these observations and improvements, the present invention can, in one preferred embodiment, be further characterized in that steps (b) and (c) are carried out simultaneously. In that embodiment, the protease is added, at a desired time point, to the refolding reaction. The desired time point can be determined in a pilot experiment, depending on the conditions chosen.

In another but not necessarily mutually exclusive embodiment, step (c) is carried out after step (b). In that embodiment, however, it is preferred that step (c) is carried out directly after step (b), i.e. without any intermediate steps. In particular, it is preferred that no step of chromatography, in particular no step of column chromatography, and/or no step of filtration, and/or no step of buffer adjustment, such as adjustment of the conductivity of the buffer including adjustment of the concentration of chaotropic agent in the buffer, is carried out between step (b) and step (c). This characteristic represents an improvement with respect to the prior art, as the process is simplified, without compromising the quality (particularly purity) of the NGF or mutein thereof obtained.

The step of protease digestion is typically carried out in a solution which allows for the cleavage of the precursor of NGF or mutein thereof, so that the mature NGF or mutein thereof is released, but which does not favor unspecific cleavage by the protease. The choice of the solution (pH, salt(s), etc. will normally depend on the type of protease chosen.

For such purpose, step (c) may be preceded, post step (b), by a step of (at least partial) buffer exchange. Various methods suitable for such buffer exchange are known, including dilution and diafiltration. Diafiltration is preferred herein. By the (at least partial) buffer exchange, the concentration of the protein structure stabilizing agent, and of the chaotropic agent (if any) can be further reduced, for example 10-fold or more, such as 100-fold or more, compared to the concentration of such agent(s) in the refolding solution. Without wishing to be bound to a particular theory, it is believed that absence or very low concentration of such agent(s) may help to stabilize the NGF or mutein thereof in the native conformation, so that many, most or all internal arginine and/or lysine residues are not surface-exposed, and this is envisaged to be associated with high cleavage specificity, specifically N-terminal of serine (S) 122 in SEQ ID NO: 1 or the equivalent most N-terminal amino acid reside of mature NGF or any mutein thereof.

The solution in which the protease digestion is carried out, particularly in case the protease is trypsin, preferably has a pH in the range of 6.0 to 9.0, preferably 6.5 to 8.5, more preferably 7.0 to 8.0, even more preferably 7.3 to 7.5, such as about 7.4. The solution in which the protease digestion is carried out, particularly in case the protease is trypsin, preferably comprises at least one divalent or trivalent metal ion, more preferably calcium or magnesium ion, and most preferably calcium ion. In the preparation of said solution, the calcium ion may be provided e.g. in the form of any of its salts, such as in the form of any of its halide salts, more preferably in the form of is chloride salt, i.e. as $CaCl_2$. It is known that calcium ions, for example, can contribute to the specificity of trypsin. The concentration of said divalent or trivalent metal ion in said solution is typically in the range of 0.1 to 10 mM, more preferably 0.4 to 4 mM, and most preferably about 1 mM.

During the protease digestion, the enzyme/substrate ratio is preferably in the range of 0.5 units (U)/mg substrate (precursor of NGF or mutein thereof) to 500 U/mg substrate, more preferably 2 U/mg substrate to 200 U/mg substrate, and more preferably 5 units/mg substrate to 100 U/mg substrate. The protein weight of the precursor of NGF or mutein thereof (substrate) can be calculated based on the concentration (protein weight/volume) which, in turn, can be determined by standard assays, e.g. Bradford, using standard proteins, e.g. bovine serum albumin, for calibration; the units of the trypsin, per ml of trypsin solution (optionally reconstituted trypsin solution, e.g. in the case of a (freeze-)dried trypsin) are in many cases indicated on the respective package of commercially available trypsin. In a non-limiting example, trypsin with a batch specific activity of 500 to 50.000 U/mg may be used.

During the protease digestion, the enzyme/substrate ratio is preferably in the range of 1/10 to 1/10000, more preferably 1/20 to 1/4000, more preferably 1/50 to 1/21000, more preferably 1/80 to 1/400, even more preferably 1/900 to 1/300, and most preferably of 1/100 to 1/200 (each indicated as protein weight/protein weight). The protein weight of the precursor of NGF or mutein thereof can be calculated based on the concentration (protein weight/volume) which, in turn, can be determined by standard assays, e.g. Bradford, using standard proteins, e.g. bovine serum albumin, for calibration; the protein weight of the protease can be calculated based on the concentration (protein weight/volume) which is normally indicated on the package of the particular protease, but can alternatively also be determined by standard assays, e.g. Bradford, as described above.

Theoretical values for parameters of proteins (e.g. pro-NGF, NGF and specific protease used, e.g. specific trypsin) can be calculated e.g. with ExPASy's ProtParam-Tool, which is available at web.expasy.org/protparam/.

It is presently understood that a protease digestion, particularly a trypsinization reaction cannot be feasibly quenched, at preparative scale. As this is the case, it is recommendable to proceed from the step of protease digestion directly to a subsequent step, such as purification. The subsequent purification is intended and suitable, inter alia, to separate the NGF or mutein thereof from the trypsin. Thereby, excessive exposure to trypsin can be avoided. This contributes to the specificity of the digestion according to the present invention, including the minimization of formation of charge variants, such as the des-nona degradation product of NGF or a mutein thereof.

In preferred embodiments, the precursor of NGF or of a mutein thereof useful in the present invention does not comprise a C-terminal cleavable peptide, i.e. in the case of human NGF or a mutein thereof does not comprise RA residues 240-241 of SEQ ID NO: 1 (bold in FIG. 15A), or homologs thereof. In such embodiments, cleavage of the C-terminal cleavable peptide, such as of the C-terminal dipeptide, is not part of the present invention.

(d) Purification

An aspect of the present invention provides a process for purifying NGF or a mutein thereof, optionally from a host cell culture, wherein a fraction of said host cell culture comprising a precursor of NGF or a mutein thereof is obtained, exposed to protease and purified, preferably on at least one stationary phase, as described herein.

The process according to the present invention represents several improvements with respect to the prior art and is based, at least in part, on the experimental findings of the present inventors. While NGF mutein can be obtained in lab scale (Example 1, Example 2), efforts have been undertaken in the present invention in order to improve the product's quality, and these were successful (see Example 5).

In particular, when characterizing NGF mutein obtained according to Example 1 and Example 2, it became evident that a significant amount of charge-variants exist (FIG. 9A, FIG. 9B). Using the pattern of these variants as guide, an improved product quality should be aimed at, and the present inventors reasoned that this may possibly be achieved by adjustment of the purification conditions. The present inventors have arrived at such conditions, as described herein and defined in the claims.

Preferably, the step of purification (d) is carried out using as starting material a composition comprising NGF or a mutein thereof, which has previously been subjected to digestion with a protease, as described above, and more preferably this composition has been subjected to clarification and/or filtration, as described above.

In one embodiment, the concentration of the protein structure stabilizing agent is not adjusted prior to the step of purification (d). Indeed, as the present inventions allows to begin the chromatographic processes using solutions of identical or similar salt composition or conductivities, compared to the preceding step of protease digestion, i.e. without extensive salt change or dilution, the process of the present invention can be considered more effective than prior art processes for the purification of NGF or muteins thereof.

Purification preferably comprises at least one step of chromatography, preferably on a suitable stationary phase. Stationary phases which do not require adjustment of the concentration of the protein structure stabilizing agent are indicated herein. The omission of adjustment of the concentration of the protein structure stabilizing agent, compared to the prior art, is one improvement according to the present invention, which significantly enhances the efficiency of purification. Indeed, while NGF mutein can be obtained in lab scale (Example 2), efforts have been undertaken in the course of arriving at the present invention in order to improve the product's quality (Example 5). Guidance in order to up-scale the process is also given (see Example 7). It is understood that adjustment of the concentration of the concentration of the protein structure stabilizing agent corresponds to an adjustment of the conductivity of the solution comprising (pro-)NGF or mutein thereof, as the case may be.

In particular, based on the guidance herein, after refolding of pro-NGF, reduction of the conductivity is not necessarily required in order to achieve binding onto a stationary phase. This is a significant advantage, since reduction of the concentration of the protein structure stabilizing agent(s), for example, in the refolding buffer leads to significant precipitation of potentially unfolded/misfolded protein (Example 2). This advantage is achievable particularly when the first chromatographic step following protease digestion is or comprises mixed mode chromatography.

In alternative, but less preferred embodiments, the concentration of the protein structure stabilizing agent is adjusted prior to the step of purification (d). While this may be readily be achieved at lab scale by centrifugation, an appropriate clarification/filtration step is suitably implemented, particularly for production scale. Buffer exchange over a membrane, including ultrafiltration and diafiltration, is an option.

Preferably, the step of purification (d) comprises multiple steps, such as two steps, three steps, four steps, and so on. Even more preferably, the step of purification (d) comprises two steps. Preferably at least one of these steps is a chromatographic step.

Preferably, chromatography according to the present invention is by column chromatography. Column chromatography normally comprises a stationary phase. For that purpose, the column is typically pre-filled with the stationary phase prior to step (d). The pre-filling of the column is not part of the core of the present invention but can be carried out by methods known in the art. The main advantage of column chromatography is the relatively low cost and disposability of the stationary phase used in the process.

The term "column chromatography", as used herein, refers to a chromatography method used to purify at least one compound to be analyzed from a liquid which comprises said compound in a mixture with at least one further compound, wherein a liquid comprising said at least one compound to be analyzed and/or to be purified is added to a chromatography column comprising a stationary phase, with the goal that individual compounds comprised in the mixture are retained by the stationary phase differently and separate from each other while they are running at different velocities and/or different binding affinities, so that said compounds elute at separate points in time. A chromatographic column may be for example comprised of a glass column which comprises the stationary phase, as described herein. Typically, a chromatography column will comprise a tap and some kind of a filter (a glass frit or glass wool plug—to prevent the loss of the stationary phase) at the bottom.

Chromatography columns are not particularly limited; from example classical preparative chromatography columns, which are a glass tubes with a diameter from 1 mm to 1000 mm, such as preferably 5 mm to 50 mm, and a height of 1 cm to 5 m, such as preferably 5 cm to 1 m, can be used.

Preferably, the step of purification (d) comprises at least two, such as for example two or three or four, separate purification steps. At any rate, when it is specified herein that whatever is carried out or not carried out prior to the step of purification (d), it is intended to mean prior to the first step of purification, as defined herein; and when it is specified herein that something is carried out or not carried out after to the step of purification (d), it is intended to mean after to the last step of purification, as defined herein. For example, as when it is said above that in one embodiment the concentration of the protein structure stabilizing agent is not adjusted prior to the step of purification (d), then this is intended to mean that the concentration of the protein structure stabilizing agent is not adjusted prior to the first step of purification. The first step of purification can be referred to as "step (d1)".

Preferably, the chromatographic steps can be selected among one or more of the following:

A capture step in which said NGF or mutein thereof is purified, optionally preceded and/or followed by clarification and/or filtration;

An intermediate step said NGF or mutein thereof is further purified, optionally followed by clarification and/or filtration;

A polishing step in which said NGF or mutein thereof is further purified, optionally followed by clarification and/or filtration.

Particularly the intermediate step is optional, and in many embodiments it is not part of the process.

Preferably, the steps of purification include at least one, preferably at least two (or exactly two) chromatographic steps.

Even more preferably, the step of purification (d) comprises two chromatographic steps, or more precisely, the step of purification (d) consists of two chromatographic steps. Further steps, which are non-chromatographic steps, may optionally be present in addition to the two chromatographic steps. Suitably these two chromatographic steps are the following two steps, preferably in sequential order:

(d1) capturing chromatography,
(d2) polishing chromatography.

The terms "capturing" and "polishing" are used herein to refer to steps (d1) and (d2). No limitations should be read into these terms or steps, unless the context dictates otherwise. For example, it is not automatically required that a particular constituent, such as a protein (NGF or mutein thereof, precursor of NGF or mutein thereof, protease and/or host cell protein(s)) bind to the stationary phase of the capturing chromatography, although in practice, said stationary phase will suitably be characterized by selective binding of one or more, but not all of these constituents (proteins).

These steps may be combined, in any order, with steps of filtration and/or clarification, as described below.

Preferably, when the step of purification comprises multiple steps, the multiple steps are steps that differ from each other in terms of chemical and/or physical selectivity. In particular, an orthogonal selectivity is preferred in order to achieve a better purification, e.g. better separation of remaining contaminants.

In particular embodiments, the purification according to the present invention comprises a step of (d1) capturing chromatography as descried below and a step of (d2) polishing chromatography as described below, preferably in that order.

Preferably, the step of capturing (d1) is carried out by chromatography, preferably column chromatography. The stationary phase used for the step of capturing can also be referred to herein as "capturing stationary phase". Preferably the capturing stationary phase is one that enables high selectivity in a broad pH and salt window (as a non-limiting and illustrative example, mixed mode chromatography).

The capturing stationary phase normally comprises a base matrix. The base matrix is typically a water-insoluble material, usually in particle from or gel form. One example of a suitable base matrix is agarose, for example highly rigid agarose.

The capturing stationary phase further comprises a ligand which is capable of binding through electrostatic interactions, preferably cationic interactions, and optionally one or more further types of interactions.

Preferably, the stationary phase used for the step of capturing is not a hydrophobic interaction chromatography (HIC) stationary phase. This is particularly advantageous when the capturing chromatography is run directly after the step of protease digestion, and/or when the concentration of arginine and/or other ions is too high to run cationic interaction chromatography efficiently.

The NGF or mutein thereof obtained from the capturing chromatography, is preferably subjected to a polishing step, as described herein. Thus, the step of capturing (d1) is preferably followed by a step of polishing (d2), in order to obtain purified NGF or mutein thereof.

Preferably, the step of polishing (d2) is carried out by chromatography, preferably column chromatography. The stationary phase used for the step of polishing can also be referred to herein as "polishing stationary phase".

To that end, it is preferred that the eluate of the capturing chromatography (meaning those fraction(s) of the eluate comprising the NGF or mutein thereof) is applied directly, as mobile phase, to the stationary phase of the polishing chromatography. In particular, it is preferred that the eluate of the capturing chromatography which comprises the NGF or mutein thereof is not subjected to any type of buffer exchange, and particular not to dialysis, but is, rather, applied directly to the stationary phase of the polishing chromatography.

The polishing chromatography is typically done using as stationary phase a suitable stationary phase, such as those described below. Said stationary phase is preferably comprised in a chromatography column.

In one embodiment the process according to the present invention consists of two chromatographic steps, (d1) a capturing step and (d2) a polishing step, both as herein described.

Mixed Mode Chromatography

Preferably, said step of capturing (d1) is carried out using a mixed mode stationary phase.

Mixed-mode chromatography (MMC), alternatively termed multimodal chromatography, is a chromatographic method in which constituents of a solution (e.g. proteins) interact with stationary phase through more than one interaction mode or mechanism. Thus, a stationary phase which is capable to bind through more than one type of interaction may also be referred to as "mixed mode stationary phase". Thus, in an embodiment the capturing stationary phase comprises a ligand which is capable of at least hydrophobic and electrostatic interactions.

Preferred ligands of that type of capturing stationary phase comprise at least one hydrophobic group and at least one positively and/or negatively charged group. In another embodiment the capturing stationary phase comprises a ligand which is capable of at least aromatic and electrostatic interactions. Preferred ligands of that embodiment comprise at least one aromatic group and at least one positively and/or negatively charged group.

The ligand is part of the capturing stationary phase, and is preferably covalently bound, directly or indirectly, to the base matrix.

Indeed, although not strictly required, it is generally preferable, in the present invention that the ligand is indirectly bound to the base matrix of the capturing stationary phase through a linker. Thus, in preferred embodiments, which are exemplified herein, the capturing stationary phase comprises (a) a linker and (b) one or more a functional groups. In that embodiment, the ligand preferably consists of (a) linker and (b) one or more a functional groups. All linkers and all functional groups described herein are combinable with each other, unless the context clearly dictates otherwise. A linker may alternatively be referred to as "spacer". By covalently binding to the linker (as more preferred), or to the base matrix (resin) directly (as less preferred), the one or more functional groups are immobilized.

Thus, in typical embodiments the capturing stationary phase comprises a linker. The type of linker is not particularly limited, but preferred linkers are suitably selected from the group comprising the linkers having hydrophilic groups. Linkers with hydrophilic groups, such as for example OH groups, are preferred in many embodiments.

Further suitable ligands will be described in the following, by reference to (a) linkers and (b) functional groups. The capturing stationary phase may comprise, for example, as ligand (a) a linker and (b) a functional group capable of electrostatic and hydrophobic interactions.

For the purposes of introduction and illustration, formula (I) represents an example of a mixed mode ligand. As can be taken from formula (I), the respective ligand comprises an aromatic group and/or hydrophobic, a charged group and a hydrophilic linker. Such ligands are particularly preferred.

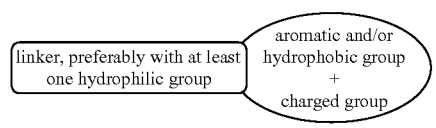

(I)

A group is designated as "charged group" herein when it has a net charge in aqueous environment at pH 7.0. The term comprises both positively charged and negatively charged groups. For illustration, a carboxylic group and a sulfonylic group will be negatively charged groups and a quarternary amine group will be a positively charged group, and the entire group comprising all positively charged groups and all negatively charged groups together are referred to as "charged groups". Among the charged groups, negatively charged groups are preferred for the purpose of the present invention. Negatively charged groups typically have cation exchange properties. Indeed, in a preferred embodiment of the present invention, the polishing step is performed on a stationary phase having cation exchange properties.

In the mixed mode chromatography according to the present invention, those embodiments wherein the stationary phase comprises a negatively charged group are preferred. Most preferred are those wherein the negatively charged group is selected from the group consisting of a carboxylic group and a sulfonylic group. More preferably, the charged group, preferably negatively charged group, is present on the mixed mode stationary phase in addition to an aromatic group and/or a hydrophobic group. Optionally the charged group, preferably negatively charged group, is present on the mixed mode stationary phase together with a linker, wherein the linker provides a covalent linkage between the base matrix (resin) on the one hand, and the charged group, preferably negatively charged group, and the aromatic group and/or a hydrophobic group on the other hand. Such a linker comprises preferably at least one hydrophilic group, as illustrated in Formula (I).

In the above formula (I), those embodiments wherein the charged group is a negatively charged group are preferred. Most preferred are those wherein the negatively charged group is selected from the group consisting of a carboxylic group and a sulfonylic group.

In some preferred embodiments, the capturing stationary phase is selected from the group consisting of "Capto™ MMC", "Capto™ Blue" (Capto™ Blue (high sub) and Capto™ Blue (low)), Capto™ Adhere, and "Blue sepharose fast flow"; all available from GE Healthcare® (Little Chalfont, United Kingdom). Stationary phases having same or similar functional groups, optionally linked to the base matrix (resin) via a linker, from this and other suppliers, may be equally used. Capto® MMC, used e.g. in Example 5, is a mixed mode stationary phase, and alternative mixed mode stationary phases can be selected and used within the disclosure of the present invention as capturing stationary phase.

A particularly preferred stationary phase, in some embodiments, is Capto® MMC. Capto® MMC is a mixed mode stationary phase. It contains a carboxylic group and thus its features partly resemble those of a weak cation exchanger. However, in addition to the ionic interactions several other types of interactions are involved, including hydrogen bonding and hydrophobic interaction. Thus, Capto® MMC comprises a ligand attached to a solid support matrix that may interact with a constituent (e.g. protein) by cation exchange (with its carboxylic group), hydrogen bonding, and hydrophobic interactions. Capto® MMC's ligand is illustrated in Formula (II):

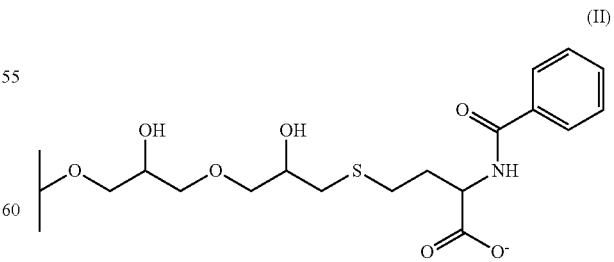

(II)

Capto™ Adhere, is an alternative mixed mode stationary phase. Capto™ Adhere for illustration, like Capto™ MMC, also comprises a ligand which is attached to a solid support matrix. Said ligand, N-benzyl-N-methyl ethanol amine, also interacts by anion exchange, hydrogen bonding, and hydrophobic interactions. Capto™ Adhere's ligand is illustrated in Formula (III):

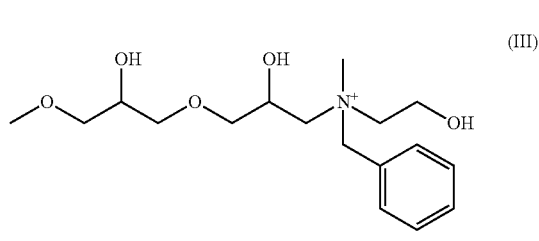 [SMILES: COCC(O)COCC(O)C[N+](C)(CCO)Cc1ccccc1]

Capto™ Blue, for illustration, is also similar to the above stationary phase in that it also comprises a ligand which is attached to a solid support matrix. It is capable to bind through aromatic and electrostatic interactions. Thus, preferred ligands of the first multimodal chromatography stationary phase may also suitably be selected among the following formulas (IV) and (V):

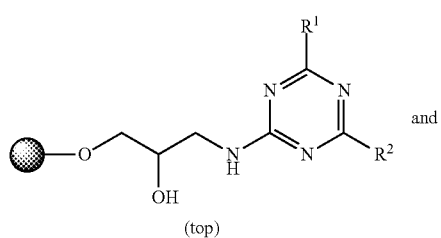

(top)

and

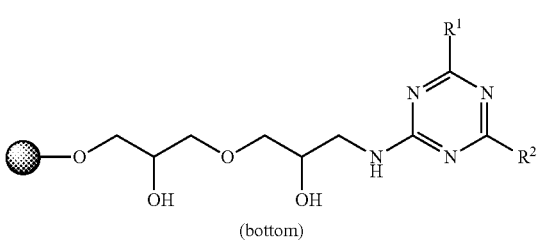

(bottom)

wherein $R^1$ of the substances of formula (V) and (VI) is preferably a functional group of formula (XI):

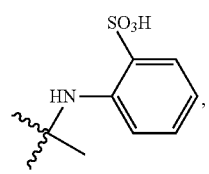

and wherein $R^2$ of the substances of formula (IV) and (V) is preferably a functional group of formula (VI):

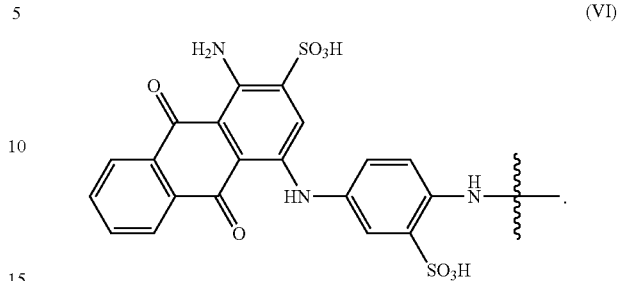

In the present context, the term "Capto™ Blue", unless expressly specified otherwise, is to be understood as encompassing all stationary phases available under the name "Capto™ Blue", in particular both "Capto™ Blue (low sub)" and "Capto™ Blue (high sub)".

In other embodiments the capturing stationary phase is selected from the group consisting of MEP HyperCel™ Mixed-Mode Chromatography Sorbent, which is commercially available form Pall Corporation. MEP HyperCel sorbent operates by a mixed-mode or multi-mode mechanism also described as Hydrophobic Charge Induction Chromatography (HCIC). HCIC is based on the pH-dependent properties of ionizable, dual-mode ligands.

Thus, most preferably said step of capturing (d1) is carried out using a mixed mode chromatography stationary phase. As described above, the mixed mode chromatography stationary phase is preferably one characterized by any one or more of the linkers described above. More preferably, the mixed mode chromatography stationary phase is a stationary phase characterized by a ligand having a negative net charge, at pH 7. For that purpose, for illustration, a ligand of formula (II) is preferred over a ligand of formula (III). Without wishing to be bound to any particular theory, it is presently understood that efficient purification using a mixed mode stationary phase not having a ligand having a negative net charge, at pH 7, for capturing chromatography, would require a mobile phase with a pH above the isoelectric point of NGF or the mutein thereof, and it is generally understood that this is less practical. Therefore, a mixed mode chromatography stationary phase characterized by a ligand having a negative net charge, at pH 7 is preferred. Most preferably, the mixed mode stationary phase is Capto® MMC, as illustrated in illustrated in Formula (II).

Alternative capturing stationary phases which may be used in the present invention include, in addition to the stationary phases described above, particularly a cation exchange stationary phase. So for example, SP Sepharose®, or Capto® S, or other cation exchange stationary phases can be used.

Preferably, however, in line with the above disclosure, the stationary phase used for the step of capturing is not an ion exchange stationary phase in the strict sense, particularly when the capturing chromatography is run directly after the step of protease digestion, and/or when the concentration of arginine and/or other ions is too high to run cationic interaction chromatography efficiently (in this embodiment, the term "ion exchange stationary phase in the strict sense" is to be understood narrowly and does not comprise mixed mode chromatography, which will be described in detail below). The term "ion exchange stationary phase in the strict sense" includes those cation exchange stationary phase and those an anion exchange resins which are not mixed mode resins. It therefore excludes stationary phases having a ligand falling under Formula (I). The present inventors have tested such ion exchange stationary phase in the capturing step, but such attempts were not as efficient for the purification of NGF or mutein thereof as the mixed mode chromatography. In particular, ion exchange stationary phase were not as efficient in a chromatography step directly following the step of protease digestion, wherein a solution comprising the NGF or mutein thereof as well as protease was added to the chromatography column. Without wishing to be bound to a particular theory, the main reason for that may be seen in the relatively high content of arginine in the solution applied to the ion exchange column As far as the stationary phase for the capture chromatography is concerned, said stationary phase is not particularly limited as long as it is suitable for capture chromatography. Preferably said step of capturing (d1) is carried out using SP sepharose as a stationary phase, preferably SP sepharose with a small particle size. Such stationary phases are usually associated with the advantage that an efficient separation of the compound of interest, in the present case NGF or mutein thereof, from other compounds can be achieved.

For elution of NGF or a mutein thereof from the capture stationary phase, a pH change and/or an increase in salt concentration (e.g. NaCl concentration) may be employed for effective elution of bound proteins. Optionally, different salts and additives may be tested or used for elution. Preferably, however, the elution is carried out by pH change. This may be done, following addition of the mobile phase comprising the NGF or mutein thereof, by contacting the capture stationary phase, preferably mixed mode stationary phase, with a mobile phase having a pH different from the pH of the mobile phase comprising the NGF or mutein thereof. Elution by pH change reduces, after elution, the conductivity of the solution comprising the NGF or mutein thereof, compared to the solution which was initially applied to the capturing chromatography column, and is therefore highly advantageous. A distinct advantage associated with the use of mixed mode chromatography in the capture step and elution therefrom by pH change (rather than salt change/ change of conductivity) is the relatively low conductivity of the eluate. Such low-conductivity eluate may be applied, in an advantageous embodiment, directly to a subsequent polishing chromatography step, also when the stationary phase in said phase is an ion exchange stationary phase.

In addition to the guidance herein and the common general knowledge, many commercial suppliers provide published guidance on chromatographic purification of proteins on specific modalities or stationary phase. For example, for the case of Capto® MMC, the following application note may be referred to: "Optimizing elution conditions on Capto® MMC using Design of Experiments", GE Healthcare®, 11-0035-48, Edition AB (2008).

Following elution, eluted fractions comprising NGF or mutein thereof, are suitably pooled.

In the past, NGF, like many other biomolecules, such as proteins, have been purified by processes involving a series of purification steps often involving one or more chromatographic steps, but the cost and efficiency of many processes are dramatically affected by dilutions, pH changes, and other operations necessary to interface various separation steps. The present inventors have arrived at advantages associated with mixed mode chromatography in the first chromatographic step, alone together with other advantages reported herein, which provide for a two-step chromatographic process using solutions of similar salt composition or conductivities, i.e. without requirement for extensive salt change or dilution, which renders, of course, such process advantageous over previously used processes.

Preferably, at no step after the capturing chromatography, protease is added. This bears the advantage that the capturing chromatography already serves for separation from protease added previously, and that an additional step of purification, such as the polishing chromatography described below, is available for further separation from any protease added previously. In other words, in that context, two chromatographic steps, including the capturing chromatography, are available for separation of NGF or mutein thereof from any protease added previously.

Cation Exchange Chromatography

Preferably, the step of polishing is carried out by chromatography. More preferably, the step of polishing is carried out by using a stationary phase that is non-identical to the stationary phase used for capturing. More preferably, the step of capturing is followed by a chromatographic step using a stationary phase with cation exchange properties, such as a cation exchange stationary phase (synonymously CEX stationary phase, cation exchange chromatography stationary phase and the like).

Cation exchange stationary phases are particularly advantageous for proteins with a relatively high isolectric point, such as NGF and a mutein thereof: normally impurities such as endotoxin, nucleic acids, negatively charged proteins do not bind to the cation exchange stationary phase, so that the NGF or mutein thereof can be suitably separated therefrom.

A cation exchange stationary phase is typically characterized by a base matrix and a linker which comprises a negatively charged group. A carboxylic group and a sulfonylic group are negatively charged groups which are particularly preferably in the context of the present invention. However, the cation exchange stationary phase does preferably not comprise a linker falling under general formula (I) above.

So for example, SP Sepharose®, or Capto® S, or other cation exchange stationary phases, can be used. Other cation exchange stationary phases can be routinely tested by the skilled person and used in the process according to the present invention.

One advantage of using a cation exchange in a step subsequent to mixed mode chromatography is that buffer exchange specifically for the purpose to enable the cation exchange chromatography to work, as in Example 2A) are not a prerequisite. As a further advantage, the precipitation specifically due to buffer exchange (Example 2A) can be avoided.

As an alternative to the cation exchange stationary phase herein described, a mixed mode chromatography stationary phase, particularly one having a ligand with a negative net charge at pH 7 may be used, in some embodiments, as stationary phase for the polishing chromatography. Having said that, it is preferred that the stationary phase used in the polishing chromatography is different from the stationary phase used in the capturing chromatography. In one embodiment, the stationary phase used for cation exchange chromatography does not fall under Formula (I).

The stationary phase used for polishing chromatography comprises preferably a stationary phase with small bead size (also known as "high performance" or ("HP") stationary phase. Such high performance stationary phases are usually associated with the advantages that an efficient separation of the compound of interest, in the present case NGF or mutein thereof, from other compounds can be achieved. In contrast to such high performance stationary phases, a stationary phase with large bead size (also known as "fast flow" or ("FF") stationary phase, is less preferred. A relatively small bead size is associated with high resolution. Most preferably, a cation exchange stationary phase with small particle size operated as outlined in the process overview (FIGS. 14A, 14B, 14C and 14D) might be used. For example, SP sepharose (GE Healthcare®) is a suitable cation exchange stationary phase; in one preferred embodiment, SP Sepharose® HP (see Example 5) may be used.

Elution from the polishing chromatography may occur by applying a mobile phase with altered pH and or altered conductivity. Preferred is elution by application of a mobile phase with increased conductivity, compared to the solution initially applied to the polishing stationary phase. Increased conductivity can be achieved by increased salt concentration. NaCl is a typical suitable salt, but other salts can be tested and used as well. Most preferably, the conductivity is increased in a linear manner over time, such as by applying a linear gradient of increasing salt concentration.

Following elution, eluted fractions comprising NGF or mutein thereof, are suitably pooled.

As a result, NGF or mutein thereof with improved purity properties is obtained. The improved purities are evidenced by a reduced amount of charge variants, particularly a reduced amounts of des-nona NGF or mutein thereof.

As a result of the process according to the present invention, NGF or mutein thereof is obtained not only at improved purity, but also at improved yield. The yield is also improved in terms of yield per space and time. "yield per space and time", as used herein, refers to the yield obtainable in a given time in a given space (volume) of refolding reaction. The improved yield is due to, inter alia, the optional significantly higher concentration of the precursor of NGF or mutein thereof in the refolding reaction, compared to the prior art, and to the significantly reduced presence, preferably substantially complete absence, of the des-nona variant of NGF or mutein thereof. The significantly higher concentration of the precursor of NGF or mutein thereof in the refolding reaction is also associated with reduced costs per NGF or mutein thereof obtained by the process of the present invention, as relatively more precursor of NGF or mutein thereof can be refolded in a given volume of a (typically relatively costly) refolding solution.

Clarification/Filtration

The process of the present invention optionally also comprises the subjecting the NGF or mutein thereof to clarification/filtration, at one or multiple stages. Preferred muteins are those described herein. The subjecting the NGF or mutein thereof to clarification/filtration may be combined, in any order, with other steps of purification, in particularly with the chromatographic steps described herein. In particular, subjecting the NGF or mutein thereof to clarification/filtration may be combined, in any order, with the steps of
 (b) (re-)folding,
 (c) purification,
 (d1) capturing chromatography, and/or
 (d2) polishing chromatography,
 all as described above.

In some embodiments, both clarification and filtration are carried out in the process of the present invention, and more preferably the clarification is carried out prior to the filtration. The main purpose of the clarification is the removal of insoluble material (e.g. precipitated protein and cell debris), whereas the main purpose of the filtration is sterilization (sterile filtration).

Thus, preferably, the composition comprising the NGF or mutein thereof is subjected to clarification and/or filtration at least one stage of the process according to the present invention. Preferably the clarification and/or filtration is performed at some stage before, during or after step (d). The clarification and/or filtration can also be referred to as clarification/filtration step. In general, a clarification/filtration step is less preferred at those stages of the process where a particular advantage can be achieved by directly applying the product of a preceding step to the subsequent step. For example, a clarification/filtration step is less preferred following (b) protease digestion and preceding (d1) capturing chromatography, particularly by mixed mode chromatography, because the direct addition of the solution subjected to protease digestion allows, among other advantages, the separation of the protease from the NGF or mutein thereof. In another illustrative example, a clarification/filtration step is less preferred following (d1) capturing chromatography, particularly by mixed mode chromatography, and preceding (d2) polishing chromatography, particularly when elution of the capturing chromatography step is by a pH gradient, because in this case a solution with an advantageously low conductivity, which can be directly subjected to polishing chromatography, is obtained, so that there is no imminent need, normally, for a clarification/filtration step at such stage, and the whole process is more rapid without such step, among other advantage.

Optionally and preferably, the clarification is preceded by a step of buffer adjustment, for example adjustment to a buffer which causes precipitation of insoluble material (e.g. precipitated protein and cell debris); this may be achieved by reducing the amount of chaotropic agent. In one preferred embodiment, the clarification/filtration is carried out after step (b) and before step (c). In another but not mutually exclusive embodiment a step of buffer adjustment may be suitable for reducing the amount of protein structure stabilizing agent. In one less preferred embodiment, such clarification/filtration is carried out after step (c) and before step (d).

In preferred embodiments, the step of clarification/filtration does not involve centrifugation. In some embodiments a respectively characterized step is preferable under GMP considerations.

Optionally, the composition comprising NGF or mutein thereof may be filtered. Filtration is suitably carried out following clarification. This sequence of steps can avoid clogging of the filter material. Particularly suitable are filters which are suited for sterile filtration, and several such filters, with different pore sizes and varying materials are commercially available. For example, a filter with a 0.2 µm membrane is suitable. Regarding filtration, suitable filter materials and filter cartridges are commercially available. For example, suitable filter materials include glass fiber filter. Some suitable filter materials and filter cartridges are described, for illustrative purposes and without limitation, in Example 5C. For example, possible filtration areas per cartridge may be selected without limitation in the range of 0.04 $m^2$ to 1.2 $m^2$. The filtration area may be suitably chosen by the skilled person based on the amount of the composition comprising the (pro-)NGF or mutein thereof, optionally considering the guidance provided in the examples herein.

Tangential flow filtration (TFF) is particularly preferred for filtration of a composition comprising NGF or mutein thereof in the context of the present invention. In general, TFF is known to be a rapid and efficient method for separation and purification of biomolecules. It can be applied to a wide range of biological fields such as immunology, protein chemistry, molecular biology, biochemistry, and microbiology. TFF can be used to concentrate and desalt a composition comprising NGF or mutein thereof, in volumes ranging from 10 mL to thousands of liters. TFF may also or alternatively be used to fractionate and/or separate large from small biomolecules, harvest cell suspensions, and clarify fermentation broths and cell lysates. For illustration, see e.g. Example 2.

Use of a Mixed Mode Chromatography in the Preparation of NGF or a Mutein Thereof Although the production of NGF (e.g. WO 2013/092776 A1) and of muteins of NGF (e.g. Malerba et al., 2015, PLOS One, vol. 10, e0136425) has been previously described, the present inventors surprisingly discovered that previously published processes are insufficient for obtaining the respective protein at high purity. As a solution to these insufficiencies, the present inventors found that mixed mode chromatography and related aspects, as described in detail herein, are suitable to provide the NGF or mutein thereof at advantageous purity.

Thus, in a second aspect, the present invention relates to the use of mixed mode chromatography in the preparation of nerve growth factor (NGF) or a mutein thereof. The mixed mode chromatography is useful in the preparation of NGF or a mutein thereof. The mixed mode chromatography is preferably used in the form of column chromatography. Based on the experiments reported herein, particularly Example 2 and Example 4, it is understood, however without wishing to be bound to a particular theory, that pro-NGF (mutein) binds so tightly to mixed mode chromatography, that it cannot be efficiently eluted except for stringent pH conditions, whereas NGF (mutein) does bind reversibly to mixed mode chromatography, so that it can be recovered efficiently, and thereby separated from precursor of NGF. Therefore, the mixed mode chromatography is particularly useful for purification of (mature) NGF or mutein thereof, which can be eluted from the mixed mode chromatography and thereby obtained.

Preferably the use of mixed mode chromatography is specifically for production of a mutein of human NGF. Preferred muteins are those described herein.

In preferred embodiments, a precursor of NGF or a mutein thereof is exposed to a protease for the purpose of digestion, and the mixed mode chromatography is used in a step subsequent to exposure to the protease. In preferred embodiments, preferably no chromatographic purification of NGF or mutein thereof is performed prior to said exposure to the protease. The second aspect thus preferably includes the use of a protease in the preparation of NGF or a mutein thereof, wherein the protease is used for exposing a precursor of NGF or a mutein thereof in order to digest said precursor, and wherein no chromatographic purification of NGF or mutein thereof is performed prior to said exposure.

Preferred aspects of the process according to the first aspect of the invention equally apply to the second aspect of the invention. Thus, everything that is described above in relation to the first aspect of the invention, including all embodiments and combinations thereof, is also applicable to the second aspect of the invention, as if it were explicitly spelled out also in this section of the specification.

The second aspect, in particular, also comprises the following preferred embodiments:

Preferably, the NGF or mutein thereof is obtained, as described in detail in relation to the first aspect of the invention, preferably in the form of inclusion bodies. In one embodiment, the NGF or mutein thereof may be obtained (a) in the form of a respective i precursor, as described in detail in relation to the first aspect of the invention. In one embodiment, the mixed mode chromatography according to the second aspect of the invention is preceded by (b) refolding and/or (c) exposure of the precursor of NGF or a mutein thereof to protease, both as described in detail in relation to the first aspect of the invention. In one embodiment, the mixed mode chromatography is performed after, and not before, the exposure to protease. The mixed mode chromatography is preferably carried out in a step (d1) of capturing, as described in detail in relation to the first aspect of the invention, and optionally but preferably followed by a step (d2) of polishing, also described in detail in relation to the first aspect of the invention.

The mixed mode chromatography is preferably carried out as described in relation to the first aspect of the invention; in particular, the mixed mode stationary phase is preferably one having a ligand with a positive net charge at pH 7.0, and is more preferably Capto® MMC.

The mixed mode stationary phase is combinable with other steps of purification as described in detail in relation to the first aspect of the invention, such as with a step (d2) of column chromatography, preferably by using a cation exchange stationary phase, e.g. using SP sepharose, preferably SP sepharose with a small particle size, such as SP sepharose FF. In particular, it is preferred that the eluate of (d1) the mixed mode chromatography (meaning those fraction(s) of the eluate comprising the NGF or mutein thereof) is applied directly, as mobile phase, to the stationary phase of (d2) the polishing chromatography. In particular, it is preferred that the eluate of the capturing chromatography which comprises the NGF or mutein thereof is not subjected to any type of buffer exchange, and in particular not to dialysis, but is, rather, applied directly to the stationary phase of the polishing chromatography.

Both wild-type NGF and muteins of NGF can be obtained according to the second aspect of the invention. Preferred muteins are those described in detail above.

Result of the Purification

The first and the second aspect provide NGF or mutein thereof characterized by solubility in aqueous solutions (opposed to insoluble and thus in inclusion bodies) and by low contamination with other proteins, among other advantageous properties, which are described herein or otherwise made available by the present disclosure.

In particular, the process of the present invention (as illustrated, without limitation, in Example 5) is suitable for production at e.g. 100 L scale (referring to the volume of the fermentation). Guidance in order to further up-scale the process is also given (for illustration, without limitation, see Example 7).

Preferably, the NGF or mutein thereof is obtained, by any aspect of the present invention, as a single charge variant. In alternative embodiments, at least 80%, preferably at least 90% of the NGF or mutein thereof is obtained as one single charge variant. The percentage of charge variant(s) may be determined, for example, by the area under the curve in a respective chromatogram (for an illustration thereof, see FIG. 13).

Optionally, the process according to the first aspect of the invention comprises an additional step of adjustment to final protein concentration and/ preparation of a desired formulation. Exemplary compositions are described herein, without limitation. For example, it is preferable that the NGF or mutein thereof is, as a result of the various aspects of the present invention, obtainable in a buffer having a pH between 4.5 and 6.5, preferably between 5.0 and 6.0. In one embodiment, an acetate buffer is a suitable buffer for such purposes, and is therefore particularly preferred. Thus, in one embodiment, the NGF or mutein thereof is obtained in an acetate buffer having a pH between 4.5 and 6.5, preferably between 5.0 and 6.0.

The results of the purification, i.e. the results of the first and second aspects of the invention, shall now be described. These characterize not only the first and the second aspects of the invention by means of result of the respective process and use, but also characterize the third aspect of the invention, as will be detailed in the following.

Mutein of NGF Obtainable by the Process and/or Use According to the Present Invention In a third aspect, the present invention relates to a mutein of NGF obtainable by the process or by the use as described herein. Since the process according to the first aspect, and the use according to the second aspect, provide to the skilled person NGF or mutein thereof characterized by solubility in aqueous solutions (opposed to insoluble and thus in inclusion bodies) and by low contamination with other proteins, among other advantageous properties described or otherwise made available by the present disclosure, the mutein according to the third aspect is also characterized by solubility in aqueous solutions (opposed to insoluble and thus in inclusion bodies) and by low contamination with other proteins, among other advantageous properties described or otherwise made available by the present disclosure.

In return, the properties of the NGF or mutein thereof according to the third aspect of the invention, in particular purity aspects thereof, also apply to the first and second aspect of the invention, because the advantageous purity is obtainable as a direct result of the purification according to the present invention, so that indeed the result of the purification characterizes advantageous features of the process and use according to the present invention.

Preferred muteins regarding the third aspects are those muteins described herein. Preferably, the mutein of NGF obtainable is substantially free of impurities. The term "impurities", as used herein, is to be understood broadly and particularly includes all macromolecules other than the specific NGF or mutein thereof. In particular, the term "impurities" comprises molecules such as host cell proteins, protease such as trypsin, nucleic acids such as DNA and RNA, as well as charge variants of NGF or mutein thereof.

Said NGF or mutein thereof obtainable according to the present invention can also be referred to as a pharmaceutically active protein or peptide. In one embodiment, the NGF or mutein thereof obtainable according to the present invention does not comprise host cell proteins at detectable levels. "detectable levels", in this context, refers to the detectability of host cell proteins by an enzyme-linked immunosorbent assay (ELISA). Respective ELISAs, also in the form of kits, are commercially available from various suppliers, e.g. for certification of good manufacturing practice (GMP), and these may be used in the present invention. Thus, the present invention explicitly also provides NGF or mutein thereof at good manufacturing practice (GMP) grade. Preferably, the NGF or mutein thereof complies with the GMP standards of the US Food and Drug Authority (FDA) and/or with the GMP standards of the European Medicines Authority (EMA).

In one embodiment, the NGF or mutein obtainable according to the present invention does not comprise trypsin (or other protease) at detectable levels. "detectable levels", in this context, refers to the detectability of trypsin (or other protease) by an enzyme-linked immunosorbent assay (ELISA). "trypsin (or other protease)" refers to the protease used in the process according to the present invention, particular at step (c).

In one embodiment, the NGF or mutein obtainable according to the present invention does not comprise pro-NGF or mutein thereof at detectable levels. "detectable levels", in this context, refers to the detectability of pro-NGF or mutein thereof by an enzyme-linked immunosorbent assay (ELISA).

In one embodiment, the NGF or mutein obtainable according to the present invention does substantially not comprise a des-nona variant, as described herein. The des-nona variant may be characterized e.g. by N-terminal sequencing of the NGF or mutein obtained.

In one embodiment, the NGF or mutein thereof obtainable according to the present invention does not comprise endotoxin and/or nucleic acid, such as DNA and RNA. In particular, it is preferred that the NGF or mutein thereof obtainable according to the present invention does not comprise host cell nucleic acids at detectable levels. Detection of nucleic acids can be performed by standard methods known in the art.

The examples reported herein demonstrate that a mutein of NGF with respective properties is indeed obtainable according to the present invention.

In a preferred embodiment, a mutein of NGF at a purity grade of 95% or more, preferably 96% or more, preferably 97% or more, preferably 98% or more, more preferably 99% or more, with respect to the total of all of its charge variants (percentage indicated in area under the curve), is provided.

In a particularly preferred embodiment, the mutein of human NGF characterized by the substitutions P61 S R100E (termed "NGF P61S R100E") at a purity grade of 95% or more, preferably 96% or more, preferably 97% or more, preferably 98% or more, more preferably 99% or more, with respect to the total of all of its charge variants (percentage indicated in area under the curve), is provided.

It is a further advantage of the present invention that relatively high amounts of NGF or mutein thereof are obtainable, in relation to the volume of the refolding reaction. In preferred embodiments, 1 to 1000 mg NGF per L of refolding reaction, such as 2 to 100 mg NGF per L of refolding reaction, 3 to 20 mg NGF per L of refolding reaction or 4-10 mg NGF per L of refolding reaction, are available, by the present invention.

In one embodiment, said a mutein of NGF is in the form of a homodimeric peptide. In another embodiment, said a mutein of NGF is in the form of a monomeric peptide. Mixtures of homodimer and monomer are also possible and equally comprised by the present invention.

The NGF and/or the mutein described herein are regarded as a pharmaceutically active peptide or protein.

Compositions

In some embodiments, the NGF and/or the mutein described herein, as obtainable by the present invention, is comprised in a composition, more preferably in an aqueous solution. Respective compositions, unless obtained directly from the last purification step, e.g. elution from the last chromatographic column (usually the polishing step) and/or filtration, are available through an additional step of adjustment to final protein concentration and/or preparation of a desired formulation. Such additional step may be, for example, a step of clarification or filtration, as described herein. Exemplary compositions useful in the present invention are described herein, without limitation.

Thus, the NGF and/or the mutein described herein may be present in a composition, e.g. in a pharmaceutical composition. The compositions described herein are preferably sterile and preferably contain a pharmaceutically active peptide or protein, as described herein, and optionally of further agents, mentioned or not mentioned herein. The compositions may be in any state, e.g. liquid, frozen, lyophilized, etc.

The compositions described herein may comprise salts, buffer substances, preservatives, carriers, diluents and/or excipients, all of which are preferably pharmaceutically acceptable. The term "pharmaceutically acceptable" describes something non-toxic and/or which does not interact with the action of the active ingredient of the pharmaceutical composition.

Suitable buffer substances for use in the invention include acetic acid in a salt, citric acid in a salt, boric acid in a salt and phosphoric acid in a salt.

In particular, the present invention also relates to a composition comprising NGF or the mutein described herein and/or obtainable as described herein, wherein the composition comprises acetate and/or an acetic acid salt. An acetic acid salt is particularly preferred. Based on literature, acetate buffer is a reasonable starting point for formulation development of NGF (Eng et al., 1997, Anal. Chem., vol. 69, p. 4184-4190). This was confirmed herein, also for an NGF mutein, see e.g. FIG. 10. In a preferred embodiment, it is recommended to formulate NGF (or mutein thereof, in particular) in 20-100 mM, (e.g. ca. 50 mM) acetate buffer, pH 5.0-6.0 (particularly preferred is pH 5.5).

In particular, the present invention also relates to a composition comprising NGF or the mutein described herein and/or obtainable as described herein, wherein the composition comprises acetate and/or wherein the composition has a pH from 4.5 to 6.5, preferably 5.0 to 6.0. In a preferred embodiment, it is recommended to formulate NGF (or mutein thereof, in particular) e.g. against 20-100 mM, (e.g. ca. 50 mM) acetate buffer, pH 5.0-6.0 (particularly pH 5.5).

The concentration of NGF or mutein thereof is not particularly limited. In preferred embodiments the concentration may be in the range of 0.01 to 10 g/l, preferably 0.1 to 1 g/L, such as in particular e.g. 0.7±0.3 g/L.

Suitable preservatives for use in the compositions according to the present invention include those known in the art, among which are for illustration but without limitation benzyl alcohol, benzalkonium and its salts, M-cresol, phenol, chlorobutanol, paraben and thimerosal.

Therapeutic Use of a Mutein of NGF

In a fourth aspect, the present invention relates to the therapeutic use of a mutein of NGF as described in the third aspect of the invention. Thus, the present invention also provides said mutein of NGF for therapeutic use, i.e. for the use in a method for treatment of the human or animal body by therapy. Therapy may include prevention and/or treatment of a condition. In view of the potential for therapeutic use, said mutein can also be referred to as a pharmaceutically active protein or peptide.

INDUSTRIAL APPLICABILITY

The NGF or mutein thereof obtainable as described herein is suitable for a variety of purposes, e.g. for in vitro assays or in animal models for specific diseases in which NGF or a mutein thereof is implicated. Respective NGF and muteins thereof are made available through the process and use according to the present invention, and thus, the respective process and use are meaningful on an industrial scale. For illustration, various uses of NGF and of certain muteins thereof have been described, e.g. in WO 2008/006893 A1.

The following examples and figures are intended to illustrate some preferred embodiments of the invention and should not be interpreted to limit the scope of the invention, which is defined by the claims.

EXAMPLES

Materials and Methods Common to More than One Example

Unless specified otherwise, the following experimental examples concern specifically the mutein of human NGF characterized by the substitutions P61S R100E (termed "NGF P61S R100E", Malerba et al. PLOS One, 2015, vol. 10, e0136425), as well as pro-forms etc. thereof, in the following also generically referred to as "NGF mutein".

NGF P61 S R100E was recombinantly expressed as pro-peptide in *E. coli* Rosetta (DE3) (strain: *E. coli* Rosetta (DE3)/pET11a-hpro NGF P61S R100E), in the form of insoluble inclusion bodies.

Equipment

TABLE 1

List of Equipment used.

| Device | Inventory-No. | Serial No. | Supplier |
|---|---|---|---|
| 1 L Bioreactors (incl. sensors and pumps) | E023, E024 | 07462/09, 07463/09 | Sartorius ® Stedim |
| 10 L Bioreactor | E082 | — | Sartorius ® Stedim |
| 300 V Power Source | E018, E019 | — | VWR |
| Äkta Explorer100a | E011 | 001054 | GE Healthcare ® |
| Äkta Explorer100a | E054 | 18111241 | GE Healthcare ® |
| Autoclave Systec ® VX-120 | E050 | 2512 | Systec ® GmbH |
| Centrifuge Galaxy 14D | E016 | 904090 | VWR |
| Centrifuge Sorvall ® Evolution RC | F683 | — | Sorvall ® |
| Clean bench | E006 | 40970929 | Thermo Scientific ® |
| Electrophoresis chamber Novex Mini Cell | — | — | Invitrogen |
| High pressure homogenizer APV 2000 | F688 | 5-07.791 | APV |
| HPLC, 1100 Series | E053 | — | Agilent |
| Magnetic stirrer MR Hei-Mix S | E013 | 30948231 | Heidolph |
| Magnetic stirrer PC-620D | 686 | — | Corning |
| pH-Meter inlab pH720 | E017 | 9080718 | WTW |
| Photometer Genesys 10uv | E051 | 2L9Q013008 | Thermo Spectronics |
| Pipetus | — | — | Hirschmann Laborgeräte |
| Pump VL 1000 | F606 | 0208004 | Verder |
| Scale | F651 | — | Sartorius ® |
| Scale | E030 | W092934 | Kern |
| Scale | E009 | — | Mettler |
| Shaker IKA KS 4000ic | E049 | — | IKA |
| Vortexer | E012 | 40934086 | VWR |

Protein Parameters of Proteins and Peptides Described Herein

Theoretical values for protein parameters of relevant proteins (pro-NGF, NGF and recombinant porcine trypsin) were calculated with ExPASy's ProtParam-Tool, which is available at web.expasy.org/protparam/. These are shown in Table 2, as follows:

TABLE 2

| Theoretically deduced properties of relevant proteins | | | |
|---|---|---|---|
| | pro-NGF mutein P61S and R100E (with reference to SEQ ID NO: 2) | NGF mutein P61S/R100E (with reference to SEQ ID NO: 2) | porcine Trypsin |
| MW monomeric | 24.8 kDa | 13.23 kDa | 24.4 kDa |
| pI | 9.7 | 8.2 | 7.0 |
| ε | 25168 l/mol/cm | 19668 l/mol/cm | 34295 l/mol/cm |

Analytical Methods
SDS-PAGE and Western Blot

SDS-PAGE and Western Blots were performed using standard procedures. For SDS-PAGE, 12% Bis-TRIS NuPAGE gels (Article No. NP0342BOX from Thermo Fisher™). were operated under reducing conditions at constant Volt (175 V) in NuPAGE MES-running buffer (Article No. NP0002 from Thermo Fisher™). The primary antibody for Western Blot was purchased from Santa Cruz Biotechnology (NGF (H-20) sc-548). Examples of results are shown e.g. in FIG. 9A and FIG. 10.

Analytical CEX-HPLC

CEX-HPLC was performed using a ProPac SCX-10 from Dionex. The column was operated with 50 mM citrate buffer, pH 5.5 at 1 mL/min. For elution, 1 M NaCl (B) was added and a linear gradient over 50 minutes from 0-100% B was executed. An example of results is shown in FIG. 9B.

SE-HPLC

SE-HPLC was performed using a Superdex 200 Increase 10/300 GL from GE Healthcare®. The column was operated in PBS. Product was detected at 280 nm.

Endotoxin, DNA and HCP

Endotoxin, DNA and host cell proteins (HCP) were determined according to standard protocols.

Example 1: Lab-Scale Expression of a Mutein of Human NGF (NGF P61S R100E)

Production Strain

The gene encoding for pro-NGF was cloned to pET11a expression plasmid. The gene was derived from *H. sapiens* and two point mutations (namely P61S and R100E) were introduced into the open reading frame. Subsequently, chemical competent Rosetta (DE3) cells were transformed with the expression plasmid and a single colony was selected (the resulting strain was termed E5901-STRAIN (=*E. coli* Rosetta (DE3)/pET11a-pro NGF P61S R100E NGF RCB C-151101)). Aliquots were stored at <−60° C., in 1.0 mL.

In Example 1, initial fermentation development based on the strain E5901-STRAIN is described.

Equipment

| Device | Inventory-No. | Serial No. | Supplier |
|---|---|---|---|
| Autoclave Systec ® VX-120 | E050 | 2512 | Systec ® GmbH |
| Centrifuge Galaxy 14D | E016 | 904090 | VWR |
| Centrifuge Sorvall ® Evolution RC | F683 | — | Sorvall ® |
| Clean bench | E006 | 40970929 | Thermo Scientific ® |
| Magnetic stirrer MR Hei-Mix S | E013 | 30948231 | Heidolph |
| Magnetic stirrer PC-620D | 686 | — | Corning |
| pH-Meter inlab pH720 | E017 | 9080718 | WTW |
| Photometer Genesys 10uv | E051 | 2L9Q013008 | Thermo Spectronics |
| Pipetus | — | — | Hirschmann Laborgeräte |
| Shaker IKA KS 4000ic | E049 | — | IKA |
| Weight Kern 572 | E030 | W092934 | Kern |
| Weight Mettler AE160 | E009 | — | Mettler |
| 1 L Bioreactors (incl. sensors and pumps) | E023, E024 | 07462/09, 07463/09 | Sartorius ® Stedim |

Growth Media
Complex Medium for Fermentation

The complex medium used for fermentation was composed of: 49.3 g/L yeast extract, 0.61 g/L MgSO$_4$*7H$_2$O, 0.5 g/L NH$_4$Cl, 14.2 g/L K$_2$HPO$_4$*3H$_2$O and 10 g/L glucose. The feed used for this fermentation was composed of 263 g/L yeast extract and 133 g/L glucose.

Minimal Media (MM) for Fermentation

| Constituent | MM I - Final conc. [mM] | MM II - Final conc. [mM] |
|---|---|---|
| Aluminum chloride, hexahydrate | N/A | 0.000063 |
| Ammonium sulfate | 39.4 | N/A |
| Boric acid | 0.005 | 0.000125 |
| Calcium chloride, dihydrate | 2 | 0.000875 |
| Citric acid, monohydrate | 25.2 | 10 |
| Cobalt(II) chloride, hexahydrate | N/A | 0.00075 |
| Cobalt(II) sulfate, heptahydrate | 0.014 | N/A |
| Copper(II) sulfate, pentahydrate | 0.032 | 0.00425 |
| Diammonium phosphate | N/A | 35 |
| Dipotassium phosphate | N/A | 45 |
| Disodium hydrogen phosphate | 7.5 | N/A |
| Ferric chloride, hexahydrate | 0.37 | 0.17 |
| Kanamycin | 0.103 | 0.103 |
| Magnesium sulfate, heptahydrate | 4 | 3 |
| Manganese(II) sulfate, monohydrate | 0.142 | 0.00375 |
| Polypropylene glycol 2000 | N/A | N/A |
| Potassium chloride | 53.6 | N/A |
| Sodium chloride | 8.5 | 40 |
| Sodium dihydrogen phosphate, monohydrate | 31.9 | N/A |
| Sodium molybdate, dihydrate | 0.001 | 0.00005 |
| Zinc sulfate, heptahydrate | 0.073 | 0.000375 |

For the batch phase, both basic media were supplemented with 30 g/L glucose. If not stated otherwise, the feed had the same composition as the respective batch medium, but contained 300 g/L of the respective carbon-source.

LB-Agar Plates with Ampicillin and Chloramphenicol

LB-agar plates were freshly poured. The medium was composed of 10 g/L peptone, 5 g/L yeast extract, 5 g/L NaCl and 15 g/L agar. After autoclaving, the medium was supplemented with 100 µg/ml ampicillin and 30 µg/mL chloramphenicol.

Fermentation

If not stated otherwise, fermentation, in this Example 1, was performed in 1 L stirred glass bioreactors controlled by a Biostat® B unit from Sartorius®. Typically, pO$_2$ was controlled to 30%, cultivation temperature was set to 37° C. and pH was controlled to 7 using 2 M phosphoric acid and 25% ammonium hydroxide. Unless stated otherwise, the batch phase was followed by an exponential feed with $F_0=6$ g/L/h and µ=0.25/h. For practical reasons, all exponential feeds were approximated by two linear feeds. Typically, induction of product expression was executed by addition of 1 mM IPTG and after induction, a constant feed rate of 10 g/L/h was applied. Cell biomass was harvested by centrifugation using a Sorvall® Evolution RC from Thermo Scientific®. The centrifuge was equipped with a SLC-6000 rotor and the culture was centrifuged at 8500 rpm and 4° C. for 30 min.

Relative Quantification of Product in Biomass Samples

At given time-points, culture samples were diluted to an $OD_{600}$ of 10 and the biomass from 100 µL aliquots of this dilution was pelleted. Pellets were resuspended in 150 µl (non-reducing) Laemmli buffer and samples were boiled for 5 min. at 95° C. 10 µL of each sample were analyzed on a 10% Bis-Tris gel from Novex. Electrophoretic separation was performed for 90 min at 125 V and gels were stained with Coomassie. Destained gels were scanned and the abundance of the band corresponding to pro-NGF mutein was quantified by densitometry. To further correct for variabilities in utilized biomass, the intensity of the band corresponding to pro-NGF mutein was normalized to the intensity of a housekeeping protein.

Relative product accumulation was calculated from the increase of the band corresponding to pro-NGF mutein, post and pre-induction. Notably, the measured value represents a specific yield (i.e. normalized to an $OD_{600}=10$). For the absolute yield of a given fermentation, the actual cell-density has to be included in the consideration (cf. below).

Absolute Quantification of Product in Biomass Samples

A pro-NGF (pro-NGF P61 S R100E) mutein standard was obtained from the European Brain Research Institute (EBRI, Rome, Italy). The standard was diluted to a concentration of 65 µg/mL in Laemmli-buffer. The stated protein concentration was defined by EBRI. A standard curve was prepared with 260, 520, 780, 1040 and 1300 ng of pro-NGF mutein standard. Samples were analyzed on the same gel as the standard curve and dilution factor of the sample was considered to calculate the absolute product yield of product at the given time. For illustration, examples of product yields are presented in FIG. 1, and example results of product quantification are presented in Table 2.

Results

Example 1A: Identification of an Optimal Medium Composition

In order to identify a suitable medium for production of pro-NGF mutein with the above-described *E. coli*-production strain, distinct media compositions (cf. Materials and Methods) were assessed for their potential to promote cellular growth and expression yield. Key parameters of fermentation runs are summarized in Table 3. In both tested minimal media, the strain encoding pro-NGF mutein did not grow satisfactorily. In contrast, growth in complex medium or defined medium supplemented with yeast extract was faster and higher cell densities were obtained. Notably, only the fermentation medium used in fermentation run #F01d resulted in significant accumulation of product. Considering that within this medium also highest cell densities were obtained, the absolute product yield with this fermentation set-up is very promising.

TABLE 3

Results of initial medium optimization for fermentation of pro-NGF mutein with the referenced RCB.

| Run # | Batch-Medium*) | Feed-Medium*) | $OD_{600}$ at induction | Duration of induction | $OD_{600}$ at harvest | Relative product accumulation |
|---|---|---|---|---|---|---|
| F01a | Complex Medium | | 114 | 6 h | 94 | <LOD |
| F01b | Minimal medium MM I | | 83 | 6 h | 111 | <LOD |
| F01c | Minimal medium MM II | | 62 | 5 h | 55 | <LOD |
| F01d | MM I + 5 g/L yeast extract | Minimal medium MM I | 98 | 6 h | 149 | 203% |

*)Medium composition according to the recipes in "Materials and Methods". All media were supplemented with Ampicillin and Chloramphenicol.

Example 1B: Productivity without Supplementation of Antibiotics

Previous fermentation and expression results were obtained from cultures fully supplemented with both relevant antibiotics (Ampicillin and Chloramphenicol). Therefore, the effects of omitting the antibiotics (Ampicillin and Chloramphenicol) on product yield were investigated next. Therefore, the four fermentations were conducted using the optimized medium composition. For two of the fermentations (F02a and F02b), the batch-medium as well as the feed were supplemented with Ampicillin and Chloramphenicol, while the main-culture media for the other two fermentations (F02c and F02d) were not supplemented with antibiotics.

No significant decrease of product yield was detected when the fermentation was conducted in main-culture media with or without antibiotics (data not shown).

In addition to determination of the relative product increase upon induction, selected product biomass samples were also analyzed using the pro-NGF mutein standard provided by EBRI, as described in Example 1A (see FIG. 1). Results of these fermentation series are summarized in Table 4.

TABLE 4

Summary of reproduction runs for fermentation of pro-NGF mutein with and without antibiotics.

| Parameter | Fermentation run No. | | | |
|---|---|---|---|---|
| | F02a | F02b | F02c | F02d |
| Batch medium | MM I with 30 g/L glucose and 5 g/L yeast extract; with Ampicillin and Chloramphenicol | | MM I with 30 g/L glucose and 5 g/L yeast extract; without Ampicillin and Chloramphenicol | |
| Feed medium | MM I with 300 g/L glucose; with Ampicillin and Chloramphenicol | | MM I with 300 g/L glucose; without Ampicillin and Chloramphenicol | |
| Fermentation volume | 1 L | | | |
| $pO_2$ | 30% | | | |
| pH | 7.0 | | | |
| Growth-Temperature | 37° C. | | | |
| Feed rate before induction | $F_0$ = 6 g/h, µ = 0.075/h (approximated by two linear feeds) | | | |
| Feed rate after induction | Constant feed: 10 g/L/h | | | |
| Inducer | 1 mM IPTG | | | |
| $OD_{600}$ at induction | 80 | 87 | 61 | 88 |
| Time at inducing conditions | 4 h | | 8 h | |
| $OD_{600}$ at harvest | 115 | 130 | 99 | 128 |
| pro-NGF mutein concentration at harvest [g/L] | n.d. | 2.4 | 1.6 | 1.9 |
| specific pro-NGF mutein yield at harvest [mg/L/$OD_{600}$] | n.d. | 18 | 17 | 15 |

Summary and Conclusions of Example 1

Based on the above, it is concluded that the production strain (E5901-STRAIN, cf. above) was successfully used for fermentation in 1 L scale. While different media compositions have been assessed for their ability to promote bacterial growth and product expression, minimal medium MM I supplemented with 5 g/L yeast extract proved to be favorable in terms of expression yield and obtainable cell density.

In terms of product formation, no significant differences were observed, when the main culture was performed either with or without antibiotics (Ampicillin and Chloramphenicol). If desired, it may be tested at a future stage whether yeast extract, or other complex constituent, is really required to achieve high cell densities and satisfactory product yield; therefore it may be tested to grow the bacteria without yeast extract, or other complex constituent, in the fermentation medium.

Example 2: Lab-Scale Purification, Establishment of Capto® MMC

The precursor of NGF mutein, used in this Example, was obtained in inclusion bodies as described in Example 1. Equipment, Production of a Mutein of Pro-NGF

TABLE 5

List of Equipment used in Example 2.

| Device | Inventory-No. | Serial No. | Supplier |
|---|---|---|---|
| 1 L Bioreactors (incl. sensors and pumps) | E023, E024 | 07462/09, 07463/09 | Sartorius ® Stedim |
| 300 V Power Source | E018, E019 | — | VWR |

TABLE 5-continued

List of Equipment used in Example 2.

| Device | Inventory-No. | Serial No. | Supplier |
|---|---|---|---|
| Äkta Explorer100a | E011 | 001054 | GE Healthcare ® |
| Äkta Explorer100a | E054 | 18111241 | GE Healthcare ® |
| Autoclave Systec ® VX-120 | E050 | 2512 | Systec ® GmbH |
| Centrifuge Galaxy 14D | E016 | 904090 | VWR |
| Centrifuge Sorvall ® Evolution RC | F683 | — | Sorvall ® |
| Clean bench | E006 | 40970929 | Thermo |

TABLE 5-continued

List of Equipment used in Example 2.

| Device | Inventory-No. | Serial No. | Supplier |
|---|---|---|---|
| Electrophoresis chamber Novex Mini Cell | — | — | Scientific ® Invitrogen |
| High pressure homogenizer APV 2000 | F688 | 5-07.791 | APV |
| HPLC, 1100 Series | E053 | — | Agilent |
| Magnetic stirrer MR Hei-Mix S | E013 | 30948231 | Heidolph |
| Magnetic stirrer PC-620D | 686 | — | Corning |
| pH-Meter inlab pH720 | E017 | 9080718 | WTW |
| Photometer Genesys 10uv | E051 | 2L9Q013008 | Thermo Spectronics |
| Pipetus | — | — | Hirschmann Laborgeräte |
| Pump VL 1000 | F606 | 0208004 | Verder |
| Scale | F651 | — | Sartorius ® |
| Scale | E030 | W092934 | Kern |
| Scale | E009 | — | Mettler |
| Shaker IKA KS 4000ic | E049 | — | IKA |
| Vortexer | E012 | 40934086 | VWR |

Details of the manufacturing process according to this Example, including improvements described in Example 2B, are given in the process overview in FIGS. 5A, 5B and 5C.

Unless specified otherwise, analytical methods were as described in the above section "Analytical methods".

Starting Point for Optimization in View of the State of the Art

At the onset, the present inventors reasoned that the process development could, in the absence of indications to the contrary, follow the basic cornerstones of NGF purification as previously reported in the literature. However, it was also borne in mind that, for an efficient production at large scale, adaptations suitable for a later scale up should be considered. Thus, it has been reasoned, based on Rattenholl et al. (supra), on WO2013092776 A1, and on other publications, that NGF and muteins thereof may be obtained at least at a lab-scale process, via pro-NGF (or a respective mutein thereof), employing unspecific digestion using trypsin and subsequent purification, thereby obtaining highly pure mature NGF or mutein thereof.

Example 2A: Purification Based on Previously Described Protocols

*E. coli* cells expressing pro-NGF mutein ("biomass") were produced as described in Example 1, and cells were lysed by addition of lysozyme and subsequent sonication on ice. Inclusion bodies ("IBs") were (1) extracted from the host cells and washed with 6% Triton X100 (in 1.5 M NaCl, 60 mM EDTA) and, and (2) solubilized in 6 M guanidinium HCl ("gHCl"), 0.1 M Tris-HCl pH 8.0, 1 mM EDTA, 100 mM (fresh) DTT. IBs were solubilized for 2 h at room temperature. Afterwards, the pH was lowered to 3-4 by addition of 37% HCl. The thus obtained solution comprising solubilized precursor of NGF mutein ("solubilizate") was dialyzed against 6 M gHCl (pH 3-4).

Refolding of pro-NGF mutein was performed in 0.1 M Tris-HCl, 1 M L-arginine, 5 mM EDTA, 0.61 g/L oxidized glutathione and 1.53 g/L reduced glutathione, pH 9.5 at +4° C. Therefore, 50 µg of protein were added per mL of refold buffer, each hour. After refolding, the reaction was dialyzed against 50 mM sodium phosphate pH 7.0. While the buffer was exchanged, significant precipitation occurred.

Pro-NGF mutein was purified over a consecutive sequence of cation-exchange chromatography (SP Sepharose® HP operated with 50 mM sodium phosphate, pH 7.0 and eluted with a NaCl-gradient) and subsequent hydrophobic-interaction chromatography (Phenyl Sepharose® HP, operated with 50 mM sodium phosphate, 1 M ammonium sulfate pH 7.0). Afterwards, another dialysis was employed to exchange the sample's buffer against 50 mM sodium phosphate, pH 7.0 (note that such second dialysis could, however, be omitted in the process of Example 5). Again significant amounts of product did precipitate throughout the process of reduction of the buffer's conductivity.

The thus prepared pro-NGF mutein was subjected to limited proteolysis by adding 1 mg trypsin per 250 mg pro-NGF. The exposure of pro-NGF mutein to the protease was for 14 h at 2-8° C.

The matured NGF was finally polished over a cation-exchanger (SP Sepharose® XL operated with 50 mM sodium phosphate, pH 7.0 and eluted with a NaCl-gradient). Finally, product was concentrated to 0.5-1 mg/mL and was frozen at <−65° C.

Example 2B: Improvements

In the following, several improvements, compared to Example 2A, as tested and implemented by the present inventors in the course of arriving at the present invention, are described. Unless the context dictates otherwise, all those details which are not expressly indicated were as described above for Example 2A.

Optimization of IB-Solubilization

While low amounts of IBs (as exemplary received from shaking flask cultures) had been previously reported to be readily solved in the solubilization buffer (6 M gHCl, 0.1 M Tris-HCL pH 8.0, 1 mM EDTA, 100 mM (fresh) DTT), the IBs obtained from high cell-density fermentations could not be resolved entirely. This could be solved, by the present inventors, by addition of 2 M urea to said solubilization buffer, which turned turned out to improve the solubilization yield significantly (data not shown). For the avoidance of doubt: the 2 M urea were present in addition to the 6 M gHCl and other ingredients.

Refolding Optimization of the Mutein of Pro-NGF Mutein

It was decided, initially based on Rattenholl et al. (2001, Eur. J. Biochem, vol. 268, p. 3296-3303; Rattenholl, 2001, Dissertation zur Erlangung des akademischen Grades doctor rerum naturalium (Dr. rer. nat.), Martin-Luther-Universitst Halle-Wittenberg (Germany)), but importantly also taking into consideration a later (up)scalability, to perform the refolding with 200 to 500 mg of pro-NGF mutein per liter of refolding reaction, preferably 200 to 300 mg of pro-NGF mutein per liter of refolding reaction. This lead to relatively good yield of solubilized precursor of NGF mutein. In particular it important to consider that by such increased amount of NGF compared to the volume of refolding reaction, and under consideration that the refolding reaction comprises relatively expensive ingredients such as glutathione and arginine, relatively more NGF (mutein) could be refolded per volume of refolding reaction, which should render the refolding economically feasible, also at production scale.

Purification of Pro-NGF Mutein

Purification of the mutein of pro-NGF, after refolding, was done by an approach which utilizes the rather high isoelectric point of pro-NGF and employs a cation exchange stationary phase (namely SP Sepharose®) for purification. In order to run this type of chromatography, for technical reasons, the refolding buffer has to be exchanged against a buffer with low conductivity. While doing this, significant quantities of mutein of pro-NGF precipitated (data not shown). This observation could be attributed to the reduction of the arginine concentration in the buffer.

Therefore, some efforts were taken to replace the capture column by a different one (a column with different selectivity), which could be more tolerant to the presence of arginine in the refolding reaction. In a first attempt to do this, the performance of several r stationary phases was assessed, but none of the approaches resulted in promising results (cf. Table 6). Therefore, the stationary phase used for the capture column was kept as it was defined by the previous process. However, due to the high isoelectric point (pI) of pro-NGF mutein, an increase in the conductivity of the running buffer (by addition of 250 mM L-arginine) was possible without affecting the performance. By this, refolded pro-NGF could be stabilized to a certain extent and the amount of precipitated pro-NGF was reduced. FIG. 2 shows a typical preparative chromatogram of the thus optimized capture step.

TABLE 6

Alternative selectivities tested for capture of pro-NGF mutein, and evaluation thereof.

| Potential capture step | Short description | Evaluation |
|---|---|---|
| Hydrophobic interaction chromatography | Hydrophobic interaction chromatography is not susceptible to conductivity and salt composition of the loaded sample. | If ammonium sulfate or sodium chloride were added to product present in the refolding buffer, protein precipitated heavily. Even addition of small quantities of ammonium sulfate (to a concentration of 0.25M) led to precipitation. Also addition of sodium chloride was not possible without provoking precipitation of product. Therefore, a capture step based on Phenyl- or Butyl-Sepharose ® is not an option. |
| Mixed-mode chromatography | Capto ® MMC is a mixed-mode stationary phase combining hydrophobic properties with those of a stationary phase for cation-exchange. Because binding is not solely mediated by ionic interactions, this stationary phase is more salt-tolerant than classical cation-exchange stationary phase. | Within an initial set-up, a phosphate buffer at pH 5.5 was supplemented with 0.25M L-Arginine and elution was facilitated with a NaCl-gradient. However, no significant amounts of product (pro-NGF mutein) were recovered by this approach. |
| Size exclusion chromatography | Size exclusion chromatography has a good resolution and is independent from the sample-buffer. The typical bottleneck of this type may of chromatography (i.e. its limited capacity) is not applicable since relatively low amounts of product are requested. | Although the preparative chromatogram looked promising, no separation of pro-NGF mutein from impurities could be achieved. This be caused by the existence of pro-NGF mutein as a polydisperse mixture under the investigated conditions. |

Regarding mixed mode chromatography, also in comparison to Example 4, it is understood by the inventors, however without wishing to be bound to a particular theory, that pro-NGF (mutein) does not elute efficiently from mixed mode chromatography, whereas NGF (mutein) does, see below and Example 4.

Protease Digestion to Yield Mature NGF

For manufacture of NGF mutein, the protease (trypsin) is essential and therefore, the inventors reasoned that ideally, the particular trypsin selected should meet the following criteria:

1. Derived from a recombinant source. Certification of animal-free raw material is pivotal for later on required GMP-compliance of the process.

2. Low side-activity of trypsin. Notably, trypsin can be subjected to autolysis. This process may result in so called pseudotrypsin, which has a broadened substrate-spectrum and possesses chymotrypsin-like activity. $Ca^{2+}$ (e.g. 1 mM $CaCl_2$)) may be added to reduce autolysis. However, nowadays typically "modified trypsin" is applied for every protocol, which requires a tight sequence specificity (e.g. for peptide finger printing). This modified trypsin is typically obtained by acylation of trypsin's exposed s-amino groups of lysine residues.

3. Low batch-to-batch variability, in order to enable a reproducible production process. Alternatively, the chosen enzyme should be delivered with a certificate stating the specific activity of the respective batch. The required amount of enzyme may then be based on activity rather than on mass.

Despite a comprehensive search, no trypsin fulfilling both criteria 1 and 2 was identified on the commercial market. The inventors reasoned that criterion 1 is more important. To reduce autolysis, addition of $CaCl_2$ may be sufficient. As a result, a recombinant 'GMP grade' trypsin from Roche (Roche 06369880103, Lot: 11534700) was chosen as raw material for the process. The sequence of this enzyme, which is expressed in *Pichia pastoris*, was derived from *Sus scrofa*. According to its certificate, the utilized trypsin batch has a specific activity of 4997 U/mg (determined according to USP).

Omission of a Second Purification Step Prior to Trypsinization

Within an initial screen searching for optimal enzyme/substrate ratios for the intended trypsinization, pro-NGF mutein obtained from the capture column (see above) was used. In contrast to a previously established process (European Brain Research Institute (EBRI), details not published, based on Rattenholl et al., supra) the present inventors decided not to use an additional hydrophobic interaction chromatography prior to trypsinization. The decision to omit such a second column purification step prior to trypsinization was mainly based on two lines of thinking: On the one hand, product obtained after the capture column was already virtually pure according to SDS-PAGE. On the other hand, the trypsinization itself may help to improve the impurity-profile by digestion of remaining host cell proteins (HCPs).

Table 7 summarizes the matrix of conditions screened within the first round. Results of trypsinization were investigated 12% SDS-PAGE (cf. FIG. 22).

TABLE 7

Layout of the first trypsinization screen. For all conditions, 990 μL of pro-NGF mutein (as eluted from SP Sepharose ® [0.38 g/L in 50 mM phosphate, pH 7.0, approx. 400 mM NaCl, one freeze-thaw cycle prior to trypsinization]) was used. Prior to trypsinization, CaCl2 * 2 $H_2O$ was added to a final concentration of 20 mM. Upon addition of the solid, massive precipitation did occur. However, based on $A_{280}$-measurements no protein did precipitate) were mixed with 10 μL of a respective trypsin solution provided in trypsin-buffer (10 mM HCl, 20 mM $CaCl_2$). After the respective exposure at 2-8° C., the reaction was stopped by addition of Laemmli-buffer.

| Amount of pro-NGF mutein [μg] | Amount of trypsin [μg] | Exposure @ 2-8° C. [hours] | | |
|---|---|---|---|---|
| | | 1 | 2 | 4 |
| 375 | 0.1 | A1 | A2 | A3 |
| 375 | 0.5 | B1 | B2 | B3 |
| 375 | 1.0 | C1 | C2 | C3 |
| 375 | 2.5 | D1 | D2 | D3 |
| 375 | 5.0 | E1 | E2 | E3 |

The results (FIG. 3) indicate that trypsinization reproducibly yields stable NGF mutein over a rather wide range of enzyme/substrate-ratios (i.e. from 1-5 μg trypsin per 375 μg NGF mutein). Timing of digestion is not highly critical. Therefore, stopping of the reaction and the time required to load the reaction to the polishing column is apparently not limiting. This finding is of special importance since the reaction cannot be suitably or economically quenched at preparative scale.

Some additional experiments were conducted in order to refine an optimal enzyme/substrate ratio for the envisaged trypsinization, and it was found that with an enzyme/substrate ratio of 1/100 to 1/200 (protein weight/protein weight), good yields of NGF mutein on the one hand and low amounts of truncated products on the other hand could be obtained reproducibly. It has to be stated that under the utilized conditions (i.e. within phosphate/arginine buffer (pH 7.0) at 2-8° C. and incubated (exposed to protease) for two to six hours) the quality of the digestion was not highly dependent on the enzyme/substrate ratio. This finding is of special importance since the underlying enzymatic digestion is prone to minor variations in the experimental set-up (e.g. alteration of trypsin's activity due to batch-to-batch variability or storage of the enzyme; timing and temperature of the incubation step (exposure to protease); errors in determination of protein concentrations). Moreover, this is also the reason why extended fine-tuning at small scale to further reduce potential truncation products seems to be not meaningful. If an "optimal" condition would be identified in small scale, there is still a good chance to produce a slightly changed product-pattern the next time virtually the same digest is repeated at larger scale.

Polishing Chromatography with the Aim to Obtain Pure NGF Mutein, Following Trypsinization In contrast to a previously established process (European Brain Research Institute (EBRI), details not published, based on Rattenholl et al., supra), which employed a SP Sepharose® stationary phase for polishing of mature NGF mutein (note: SP sepharose is a cation exchange stationary phase), the present inventors searched for a more suitable stationary phase, based on the following considerations: In order to be efficiently loaded to an SP Sepharose® column, a reduction of the conductivity of the NGF mutein-containing solution, such as by buffer exchange is required. It is however known (e.g. Example 2A) that reduction of the ionic strength of the solution does result in precipitation of the target molecule and therefore, a buffer exchange to a low conductivity buffer should be avoided. Moreover, a cation exchange stationary phase was already used for capture of pro-NGF mutein, and an orthogonal selectivity is preferred in order to achieve a better separation of remaining contaminants. A third and final argument against the use of a SP stationary phase for purification of the trypsinization reaction is that potentially remaining pro-NGF mutein would bind to this column and could be separated from mature NGF mutein merely by elution selectivity and not by binding selectivity.

In order to establish such an orthogonal polishing column for purification of mature NGF mutein, it was intended to use a hydrophobic interaction (HIC) column in a first instance. This stationary phase was not only chosen to have an orthogonal selectivity, but also because a buffer exchange to a low conductivity buffer is not necessary. Despite testing of several HIC stationary phase and conditions (e.g. Phenyl- and Butyl-Sepharose® operated with 1 M $(NH_4)_2SO_4$ and 0.5 M $(NH_4)_2SO_4$, respectively), no satisfying polishing step based on HIC could be implemented (data not shown).

However, in a further experimental setup for a polishing step, the mixed mode stationary phase Capto® MMC was tested and could be implemented successfully. It was found that with optimized conditions, the stationary phase binds NGF mutein reversibly and the product can be eluted by increasing pH (cf. FIG. 4A). In contrast, pro-NGF mutein binds irreversibly onto the stationary phase and can be only eluted by using 1 M NaOH as mobile phase (cf. FIG. 4B). Furthermore, it could be shown that trypsin does not bind at all onto the column operated at the same conditions (cf. FIG. 4C). These results provide clear evidence that the Capto® MMC stationary phase is capable of efficiently separating mature NGF mutein from trypsin and from remaining pro-NGF mutein.

Establishment of an Additional Membrane Chromatoqraphy

In order to further deplete endotoxins and DNA, an additional anion-exchange membrane was included in the process. In general, and as is commonly known, membrane chromatography is characterized in that a solution comprising a component to be analyzed or purified (in the present case NGF or mutein thereof) is passed over or through a membrane, which is normally charged. For that purpose, in the present case a STIC-membrane (Sartorius®, Goettingen, Germany) was incorporated at the positions indicated in FIG. 5C. It could be shown that NGF mutein does not bind to the membrane, and thus, a proof of concept was provided that membrane chromatography is suitable for purification of NGF or mutein thereof. For illustration of the incorporation in the entire process, including membrane chromatography, see FIGS. 5A, 5B and 5C.

Reproducibility of the Process According to Example 2

In order to probe the robustness of the process, the process was conducted five times and resulting fractions were analyzed with respect to their yield and purity. Throughout these runs, a steady optimization of process details was pursued and buffer composition, gradients and so on were adopted until the final, optimized process details (see FIGS. 5A, 5B and 5C) were established. The results indicate that in lab-scale approx. 50 to 100 mg NGF mutein can be yielded from one consistent production run. Notably, the product obtained was consistently found, by SDS polyacrylamide gel electrophoresis followed by Coomassie staining or silver staining, to be relatively pure (less than five percent of contaminating host cell proteins and only traces of truncated NGF, data not shown).

For pro-NGF mutein no meaningful method for SE-HPLC could be established. In contrast, SE-HPLC analysis for mature NGF mutein was straightforward and resulted in a homogeneous product peak of approx. 16 kDa which fits with a monomeric state of NGF mutein (data not shown).

Summary and Conclusions

The complete process incorporating the improvements according to Example 2, including membrane chromatography, is schematically depicted in FIGS. 5A, 5B and 5C.

For this process, refolded pro-NGF mutein was captured using a SP Sepharose® FF ("FF" stands for Fast Flow, i.e. a stationary phase with relatively large particles) and was subsequently treated with trypsin to yield mature NGF. For that purpose, the arginine concentration of the refolding reaction was decreased from 1 M (as recommended by the prior art) to 350 mM.

Control of the proteolytic cleavage of pro-NGF mutein to yield mature NGF mutein is considered as most critical factor for the process. Herein, conditions were identified to reproducibly facilitate cleavage with high efficiency on the one hand and prevent formation of degradation products of NGF. The experimental data herein have shown that an apparently robust production process can be established over a rather wide range of enzyme/substrate ratios. For the trypsinization, step yields are apparently good and no significant loss is expected at this stage of the process. The product pattern obtained does apparently not strongly depend from the used reaction conditions (in terms of enzyme/substrate-ratio and time of incubation (time of exposure to protease)). Notably, even if a good yield for polishing of the enzyme is expected, at least 2*x grams of pro-NGF mutein have to be processed in order to deliver x gram of mature NGF mutein.

The purification according to this example is a lean process consisting of merely two chromatographic purification steps. The existing purification process was further optimized and several aspects were adopted for scale-up (see FIGS. 5A, 5B and 5C). Exemplary, previously used methods of cell disruption were replaced by high-pressure homogenization and all dialysis steps could be replaced by tangential-flow filtration. The thus established process is capable to deliver NGF mutein of high purity.

Despite the named challenges, the overall process seems to be capable of delivering product which initially appears to be of reasonable quality. For more detailed analysis, see, however, Example 4.

Example 3: Pooling and Initial Formulation

This example was performed obtained with NGF mutein as described in Example 2.

Formulation of NGF Mutein

Dilution assays confirmed that pro-NGF is instable at L-Arginine concentrations below 250 mM and will start to precipitate (data not shown). In contrast, NGF is a more stable molecule and does not require an additive to stay in solution. Therefore, the polished NGF could be readily diafiltered into PBS at concentrations between 0.5 to 1 g/L.

Pooling of NGF Mutein

Besides improvement of the manufacturing process (initial attempts: Example 2), another aim was to deliver approx. 300 mg of NGF mutein. Strikingly, the data obtained showed that this material cannot be purified within one batch at lab-scale. Therefore, material derived from five reproduction runs was pooled.

Example 4: Stability of NGF Mutein

Stability of NGF mutein obtained as described in Example 2B and FIG. 5 was tested. The background for this testing is the rationale that, for an industrial production at high purity, a possible product heterogeneity (i.e. the fractions of NGF, pro-NGF mutein and possible degradation products) would have to be addressed, and solutions that can contribute to high product purity/low product heterogeneity would have to be identified.

Notably, the process design established in Example 2 (FIGS. 5A, 5B and 5C) requires addition of an unspecific protease at a rather late stage of the process. Although the polishing column was shown to efficiently discriminate between trypsin and NGF mutein, entire removal of the protease is not absolutely guaranteed and a residual probability that traces of the protease remain in the final product remains. Therefore, stability of the obtained NGF mutein was now tested experimentally.

Although no trypsin can be detected on silver-stained SDS-PAGE (cf. FIG. 6), residual protease may be revealed by an indirect approach. If the product produced according to the outlined protocol is stored for 24 hours at room temperature, a slight degradation band becomes evident (cf. FIG. 6). This degradation does likely indicate the presence of trypsin traces in the final product and may indicate that an additional peptide is cleaved off at Arg 9 of the mature protein (des-nona degradation product). Indeed, mass spectrometric analyses confirmed that said slight degradation band corresponds to a des-nona degradation product (data not shown), i.e. to a degradation product of mature NGF which lacks the first nine amino acid residues of mature NGF, in other words, the first nine amino acid residues of SEQ ID NO: 2.

Interestingly, available crystal structures of mature NGF (e.g. PDB-IDs 1 BTG and 1 BET) show proteins that are also devoid of this N-terminal peptide. This may indicate that the N-terminal part of NGF is rather flexible and therefore, more susceptible to tryptic digestion than the core of the molecule, which may be more rigid.

In general, SDS-PAGE analysis of NGF mutein can be done using standard procedures. Gels stained with colloidal Coomassie are normally characterized by a good linearity and can be used for quantification of product (data not shown). Silver staining of SDS-PAGE is a suitable alternative (data not shown).

In order to reduce the likeliness of additional degradation, a more acidic formulation of the final product was tested. As potential buffer for this purpose acetate buffer at pH 5.5 was chosen. On the one hand, this buffer seems to be a good choice for NGF (Eng et al., 1997, Anal. Chem., vol. 69, p. 4184-4190), and on the other hand, the activity of potentially remaining trypsin should be reduced by at least 50% as compared to PBS. In order to evaluate stability and activity of the product in the recommended buffer experimentally, a small amount of product was buffer-exchanged and aliquots were incubated (exposure to protease) at 25° C. and 4° C., respectively. Exposure to protease was stopped at several time points by addition of Laemmli buffer and freezing of the respective samples. The results (FIG. 7 shows exemplary degradation at 25° C.) indicate that formulation in the acetate buffer indeed did result in a significantly enhanced product stability.

Even at 25° C. NGF mutein did not completely degrade after 10 days. However, some degradation is observed in both buffers. This indicates that the selection of the formulation buffer alone is helpful, but not sufficient, for stability of NGF mutein over time.

In order to get further insight into the observed degradation, purified NGF mutein (Example 2B) was analyzed by CEX-HPLC as outlined in the 'Analytical Methods' section. The analytical chromatogram revealed that the purified product does not represent a single peak of NGF mutein, but likely differentially charged molecules are present (cf. FIG. 8).

Example 5: Trypsinization Prior to Chromatography, Switching the Column Sequence and Other Improvements The present Example is based on Example 2, however with several important differences, which will be described below. Some of these differences take into consideration the results of Example 4 and aim at avoiding drawbacks observed.

While, in Example 2, refolded pro-NGF was captured using a SP Sepharose® FF and was subsequently treated with trypsin to yield mature NGF, which required that the arginine concentration of the refolding reaction was decreased from 1 M to 350 mM (see there), the present inventors considered the following: On the one hand, a further reduction of the arginine concentration would lead to a more pronounced precipitation at this stage. On the other hand, using these conditions the employed capture column possessed a low capacity and did hardly improve the product's purity profile.

Among the most important differences is the fact that trypsin was added directly to the refolding reaction and the sequence of the purification columns was reversed. The combination of these differences was arrived at by the present inventors based on the observation that Capto® MMC stationary phase efficiently removes residual trypsin from the reaction (Example 2) and the fact that it has a higher salt-tolerance as compared to SP Sepharose®.

The present inventors reasoned as follows: by using a SP Sepharose® with a small particle size (i.e. SP Sepharose® HP) and selecting an adequate gradient, reduction of product-related impurities (i.e. charge-variants, des-nona degradation product) should be achievable within the polishing step. Notably, with these adaptations, the same columns as compared to the previously established process (Example 2) are utilized, merely their sequence is switched. Moreover, the total amount of column purification following exposure to trypsin is increased from one to two. This Example was conducted in order to test whether depletion of residual protease could be more efficient and/or whether a NGF mutein can be obtained at higher purity (i.e. with less host cell proteins and/or less charge variant contamination, including remarkably less des-nona degradation product).

Example 5A: Fermentation

In order to generate starting material for the extended process development and to assess reproducibility of the fermentation process at an intermediate scale, a 10 L fermentation according to the previously outlined protocol (Example 1) was conducted. The fermentation process scaled well and observed in-process controls (mainly growth curve and product formation) were found as expected from development at 1 L scale. Product formation was induced, by addition of IPTG, at an $OD_{600}$ of 86 and lasted for eight hours until a final $OD_{600}$ of 106 was reached. Notably, quantification of expression yield was not possible due to a lack of adequate reference material.

Harvested Biomass was disrupted by two cycles of high-pressure homogenization at 1000 bar and IBs were recovered from cell debris by centrifugation. The IBs were washed four times and afterwards, aliquots were frozen for further experiments. In total, 250 g inclusion bodies (IBs) were recovered from the fermentation.

Example 5B: Direct Trypsinization of the Refolding Reaction

It has previously been reported that the mature form of the NGF mutein NGF P61 S R100E is not susceptible towards further trypsin cleavage at 4° C. (Malerba et al., 2015, PLOS One, vol. 10, e0136425). To probe how stable the target product is under refolding conditions, different ratios of enzyme to protein were tested and the resulting product pattern was analyzed by SDS-PAGE. Therefore, the refolding reaction was set-up as reported in Example 2 with the overall protein concentration determined by Bradford. The proteolytic cleavage was conducted for 4 hours at 2-8° C. In addition to the parameter described above, also the influence of the arginine concentration on proteolytic cleavage was tested by diluting the refolding reaction prior to addition of the protease.

The results visualized by SDS-PAGE did not reveal any significant differences between the distinct conditions assessed (data not shown). For all conditions, pro-NGF mutein was digested below the limit of detection and significant amounts of NGF mutein were formed. The impurity pattern of the single reactions was not significantly impacted by the amount of trypsin added, which suggests that trypsin can neither improve the quality of the product by digesting host cell proteins nor will influence its yield by digesting significant amounts of product.

Interestingly, however, for none of the trypsinization reactions conducted at the stage of the refolding reaction, formation of des-nona degradation product of NGF mutein was observed. This stands in sharp contrast to nearly all digestions previously done (cf. Example 2). Thus, by adding trypsin early, directly to the refolding reaction and prior to the first chromatographic purification, NGF mutein can be obtained essentially without contamination by the des-nona degradation product of NGF mutein.

Example 5C: Clarification and Filtration of the Refolding Reaction

After reducing the arginine concentration of the refolding reaction from 1 M to 333 mM, significant precipitate is formed. This can be efficiently removed with a glass fiber filter possessing a nominal pore size of 1.2 µm (e.g. GF+from Sartorius®). In addition, this glass fiber possesses a positive charge and thus, could eventually support depletion of endotoxins and DNA.

Yet, establishment of the required filter area is complicated by the available filter cartridge sizes. Being available with a rather small spread between possible filtration areas per cartridge (0.04 $m^2$ for the smallest cartridge and 1.2 $m^2$ for the largest cartridge), high volumes have to be processed throughout process development to eventually elucidate how much volume can be processed by unit of filter area. While it was shown for a previous intermediate scale that a volume corresponding to approx. 70 L of refolding reaction can be readily processed with a filtration area of 0.4 $m^2$, the minimal area required for this purpose was not readily established. To further narrow the required specific filter area down, an additional intermediate scale with approx. 60 L refolding volume was conducted. This time, GF+ cartridges with a nominal membrane area of 0.04 $m^2$ were employed. To filter the entire refolding reaction, 8 of these cartridges were required. The thus clarified product was readily filtered over 0.2 µm membranes.

As an alternative approach to determine the required filtration area, a syringe filter with 1.2 µm nominal retention rate and a filtration area of 5.3 $cm^2$. With one piece of this type of filter, approx. 3 mL of diluted refolding reaction (corresponding to 30 mL of refolding reaction) could be processed. Yet, scalability of results obtained with this syringe filter is questionable.

Example 5D: Establishing Capto® MMC as Capture Column

In order to improve the process (Example 2) further, it was assessed, if the refolding reaction can be directly loaded on a capturing column based on Capto® MMC. Yet, it was found that NGF mutein does not bind to the column under the conditions of the refolding reaction and therefore, as a solution, reduction of the arginine concentration achieved through a 1 to 3 dilution is required.

Initially, the capacity of the Capto® MMC capture column was estimated by loading a respective 5 mL and a 28 mL column with varying volumes of NGF mutein. While the capacity was not significantly affected by the residence time, it was found that, for the capturing column, approximately 5 mL Capto® MMC per L of refolding reaction should be employed.

As shown previously, the Capto® MMC achieves separation of product from non-product related impurities (especially from pro-NGF and trypsin) mainly by a differential binding selectivity (Example 2). To probe whether an additional purity gain can be accomplished, the performance of a stationary phase with smaller particle size (i.e. Capto® MMC ImpRes) was tested and the effect of various pH-gradients was assessed. However, no significant additional improvement of product purity could be achieved by these approaches, and for the sake of a lean production process, elution with a step gradient into a single product fraction is desirable. An Example thereof is shown in FIG. 11.

Example 5E: Polishing of NGF Using SP Sepharose® HP

For polishing of NGF, the present inventors reasoned that a cation exchange stationary phase (CEX stationary phase) with small particle size operated as outlined in the process overview (FIGS. 14A, 14B, 14C and 14D) might be used. In this example, SP Sepharose® HP was used.

FIG. 13 shows a representative preparative chromatogram of such a polishing step and summarizes analytical methods employed to evaluate the quality of distinct fractions.

Interestingly, the SP Sepharose® HP, operated as polishing column, is capable to deplete potentially truncated NGF mutein (des-nona degradation product of NGF mutein according to amino acid sequence) and charge-variants of the target molecule (see FIG. 12c and FIG. 13). Notably, the des-nona degradation product of NGF mutein was only detected for product obtained according to the protocol of Example 2/FIGS. 5A, 5B and 5C (trypsinization of pre-purified NGF), but not for product obtained according to the protocol of Example 5/FIGS. 14A, 14B, 14C and 14D. When trypsinization was done directly in the refolding reaction, virtually no formation of the des-nona degradation product of NGF mutein was observed. It is tempting to speculate, without however wishing to be limited to any particular theory, that this might be caused by a change of reaction conditions and a more rigid NGF confirmation under the altered trypsinization conditions.

Thus, the present inventors could show that a correctly operated preparative CEX (SP Sepharose® HP) with adequately defined pooling criteria might be able to improve the quality of purified NGF (or mutein thereof, in particular).

Summary and Conclusions

In summary, this Example shows that switching the column sequence is advantageous, particularly when trypsin is directly added to the refolding reaction (i.e. wherein no chromatographic purification is performed prior to the exposure to protease).

The present inventors, in Example 5, added trypsin directly to the refolding reaction. The following considerations are theoretical and intend to provide a molecular explanation, but they should not be understood to limit the invention to any particular theory: since unfolded pro-NGF mutein should be more prone to proteolytic cleavage than correctly folded pro-NGF mutein, the early addition of protease, as shown in Example 5, may help to reduce the amount of precipitate. In addition host cell proteins (HCPs) might be removed enzymatically and thus, the purity of NGF (or mutein thereof) could potentially be further improved.

Aspects of the present invention, as established in Example 5, including the switched column sequence and early protease digestion (Example 5), are represented in a schematic overview of the final manufacturing process, in FIGS. 14A, 14B, 14C and 14D.

Example 6: Potency Bioassay

A bioassay measuring the potency of NGF P61 S R100E to proliferate TF-1 cells was established. The measured potency corresponds to the potency of NGF (data not shown).

Example 7: Considerations for Further Upscale

This Example is based on the disclosure of FIGS. 14A, 14B, 14C and 14D, but comprises considerations suitable for an up-scale. These considerations are based on results from process development at the scale of Examples 1-4 and take process-logistics of later scale and equipment into account. Key considerations are:

Fermentation

Fermentation is conducted at 100 L scale and will yield 2 to 4 kg of IBs.

Based on limitations of the refolding volume, a fraction, e.g. approximately one third, of the resulting IBs is further processed, per time. The process is repeated with the remaining fractions.

Trypsinization

By showing that the trypsinization is rather robust, set-up of conditions for the intended up-scale can be guided rather by process logistics than by requirements of NGF (mutein). Refolding and trypsinization at the intended scale may therefore follow the following key facts:

Refolding is performed at a final volume of 500 L at 2-8° C.

Approx. one third of the IBs obtained from a 100 L fermentation is solubilized in 10 L volume. The protein concentration in this solubilizate is determined by Bradford.

The IB solubilizate is continuously added to the pre-cooled refolding buffer to give a final concentration of approx. 300 mg protein per L.

After incubation (exposure to protease) overnight, the refolding reaction is concentrated to approx. 25 L and afterwards, is diluted to decrease the arginine concentration from 1 M to 333 mM. Thereby, a significant precipitate forms and approximately 40% of protein remains in solution.

In order to save process time, 0.8 g trypsin (corresponding to 1/100 of the expected total protein amount at this stage) can be directly added to this product. While being incubated (exposed to protease) for 4 hours at 2-8° C., the precipitate may be removed by filtration.

Clarification/Filtration

Glass fiber filtration (e.g. GF filtration, Sartorius®, Goettingen, Germany) cartridges with a nominal pore size of 1.2 µm are a good choice for clarification of the product after dilution of the refolding reaction. The filtration are should be chosen according to the volume. Other options for clarification may also be explored.

Capturing Purification

For purification of NGF from a refolding volume of 500 L, the following capturing column may be used:

Column with 14 cm diameter packed with Capto® MMC to a final column volume of 4-5 L. This corresponds to a bed height of approximately 27 cm.

The column is operated with 50 L 350 mM Arg, 20 mM $iPO_4$, pH 6.0 and 50 L 350 mM Arg, 50 mM $iPO_4$, pH 9.5, respectively. Elution with the second buffer is executed as single step.

The column is to be operated with a volumetric flow rate of not more than 0.5 L/min, which corresponds to a residence time of 8 min.

With this volumetric flow rate, operation of the column including column preparation and cleaning, will take 5 h, i.e. one working day has to be reserved for this step.

Polishing Purification

Considering the amount of product expected and typical capacities of employed stationary phases, column size at the polishing stage may be limited rather by technical equipment at an individual production facility than by the specific capacity of the stationary phase. Therefore, a column with 7 cm diameter may be packed with SP Sepharose® HP to a final column volume of 0.8-1.0 L. This corresponds to a bed height of approximately 23 cm.

The column will be operated with 20 L 50 mM $iPO_4$ (note: $iPO_4$ stands for inorganic phosphate buffer), pH 6.0 and 20 L 0.5 M NaCl in 50 mM $iPO_4$, pH 6.0, respectively.

The column is to be operated with a volumetric flow rate of not more than 0.2 L/min, which corresponds to a residence time of 5 min. With this volumetric flow rate, operation of the column including column preparation and cleaning, will take approx. 5 h.

Fractionation of eluate from the polishing column is advisable. Fractionation should be done with a volume of 0.5 CV per fraction or according to the peak-shape.

In contrast to SDS-PAGE, which is not capable to reveal differences between the distinct fractions, CEX-HPLC is a suitable method for analysis of the thus generated fractions.

Formulation

Parameters for formulation of NGF (or mutein thereof, in particular) in e.g. 100 L scale can be defined based on the findings herein. Based on the results established throughout the initial process development, it is recommended to formulate NGF (or mutein thereof, in particular) e.g. against 50 mM acetate buffer, pH 5.5, for example at a concentration of 0.7±0.3 g/L.

Summary and Outlook

The present inventors have shown that by trypsinization at an early stage, i.e. before the first chromatographic step, preferential digestion pro-NGF mutein is achievable.

Notably, under none of the tested conditions a previously observed truncated form of mature NGF mutein (des-nona degradation product) was observed, if the trypsinization was performed directly after refolding (Example 5). As NGF mutein, in contrast to pro-NGF mutein, was not observed to be heat-sensitive, this adopted process might also allow the chromatographic purification and polishing to occur at room-temperature, which would be highly beneficial in terms of process logistics. However, for the refolding being effective and likely also for trypsinization, environmental conditions at 2-8° C. are required.

According to the present invention, an earlier existing purification process (e.g. WO 2008/006893 A1, Malerba et al. PLOS One, 2015, vol. 10, e0136425) was amended and thereby optimized. Exemplary, a filtration strategy to clarify the refolding reaction was established and it was shown that the product's quality can be improved by the details described herein, e.g. application of a cation-exchange chromatography using adequate pooling criteria.

BRIEF DESCRIPTION OF THE FIGURES

FIG. 4A: Chromatogram of 5 mL Capto® MMC column with initial pH elution gradient over 15 CV (column volumes), followed by a salt elution step and ended by CIP.
Load: Trypsinized pro-NGF mutein="NGF" (~11 mg) in 150 mM Arg, 10 mM CaCl, 50 mM iPO$_4$ pH 6.0
Buffer A: 250 mM Arg, 50 mM iPO$_4$ pH 6
Buffer B1 (pH elution): 250 mM Arg, 50 mM iPO$_4$ pH 9
Buffer B2 (salt elution) 1 M NaCl, 250 mM Arg, 50 mM iPO$_4$ pH 9
CIP: 1M NaOH FIG. 4B: Chromatogram of 5 mL Capto® MMC column with initial pH elution gradient over 15 CV, followed by a salt elution step and ended by CIP.
Load: 100 mL refolded pro-NGF mutein (0.05 g/l) in 250 mM Arg, 10 mM iPO$_4$ pH 6
Buffer A: 250 mM Arg, 50 mM iPO$_4$ pH 6
Buffer B1 (pH elution): 250 mM Arg, 50 mM iPO$_4$ pH 9
Buffer B2 (salt elution) 1 M NaCl, 250 mM Arg, 50 mM iPO$_4$ pH 9
CIP: 1M NaOH FIG. 4C: Chromatogram of 5 mL Capto® MMC column with initial pH elution gradient over 15 CV, followed by a salt elution step and ended by CIP.
Load: 15 mL of Trypsin (0.5 g/l) in 250 mM Arg, 50 mM iPO$_4$ pH 6
Buffer A: 250 mM Arg, 50 mM iPO$_4$ pH 6
Buffer B1 (pH elution): 250 mM Arg, 50 mM iPO$_4$ pH 9
Buffer B2 (salt elution) 1 M NaCl, 250 mM Arg, 50 mM iPO$_4$ pH 9
CIP: 1M NaOH FIGS. 5A, 5B and 5C: Outline of the process according to Example 2, including improvements described in Example 2B.

FIG. 6: Degradation of product stored at room temperature may reveal the presence of residual trypsin in the final product. Shown are two samples stored for 24 hours at room temperature (Lane 1) or in frozen condition (Lane 2), respectively.

FIG 9A: Exemplary SDS-PAGE of NGF. Note that in Lane 1 a truncated form of the product (des-nona degradation product of NGF mutein) can be detected by this method. Depending on composition of the final formulation, residual trypsin within the product might result in formation of this undesired side-product over time.

FIG. 9B: Exemplary CEX-HPLC chromatogram of a NGF preparation. On SDS-PAGE, the first eluting species is clearly identified as slightly truncated form of NGF, while the other peaks possess the same migration behavior. Therefore, the latter eluting species is likely a charge variant of the main-product. Note that the actual pattern of NGF-variants observed in CEX-HPLC depends on the process used to obtain the respective preparation.

FIG. 12A: Preparative chromatogram.

FIG. 12B: SDS-PAGE of selected fractions.

FIG. 12C: Overlay of CEX-HPLC chromatograms of selected fractions

FIGS. 14A, 14B, 14C and 14D: Outline of a production process according to the present invention (for details and illustration see Example 5).

FIGS. 15A, 15B and 15C: Human Nerve Growth Factor and its precursors as encoded and expressed in humans.

FIg. 15A: SEQ ID NO: 1: Sequence of pre-pro human NGF as encoded by the respective human Open Reading Frame.

Figure 1:
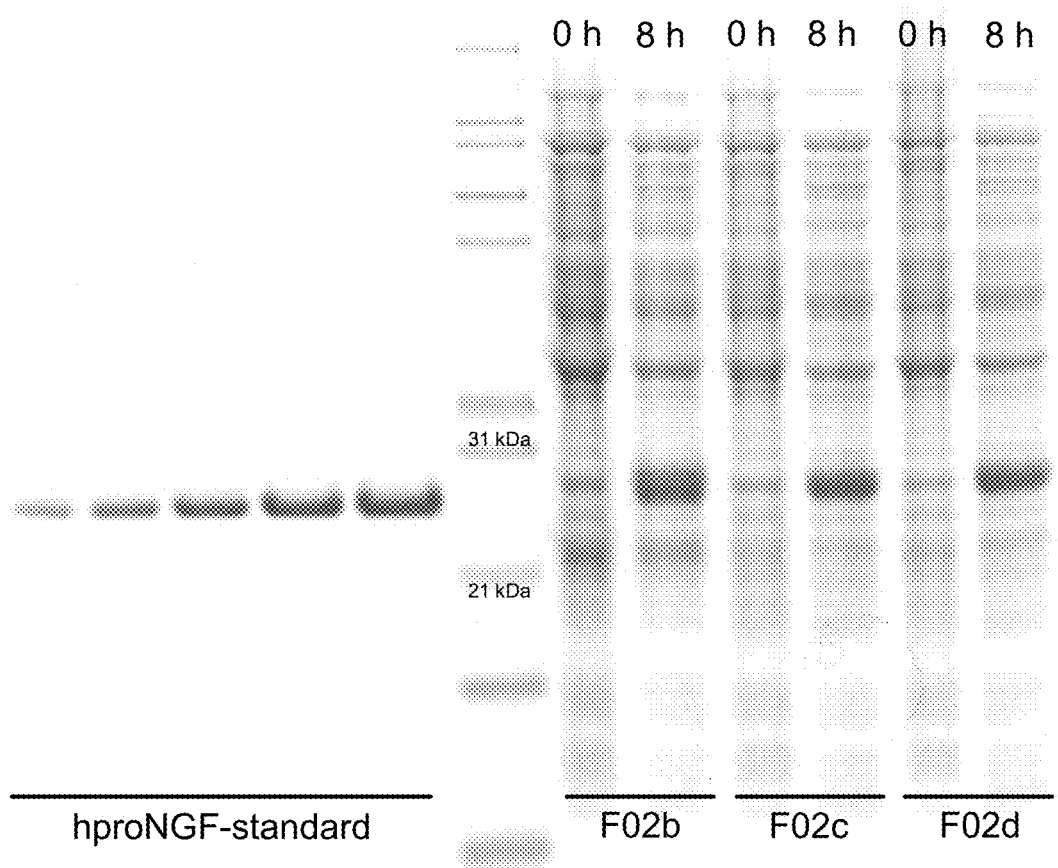
FIG. 1: Quantification of product in biomass samples using a pro-NGF mutein standard provided by the European Brain Research Institute (EBRI): The standard was applied with 60, 520, 780, 1040 and 1300 ng, respectively. Shown are biomass samples from Example 1 (for details see there): one fermentation with (F02a) and two fermentations without (F02c and F02d) antibiotics in the main culture. For each fermentation, a sample at the time of induction (0 h) and a sample at the time of harvest (8 h post induction) were analyzed.
Figure 2:
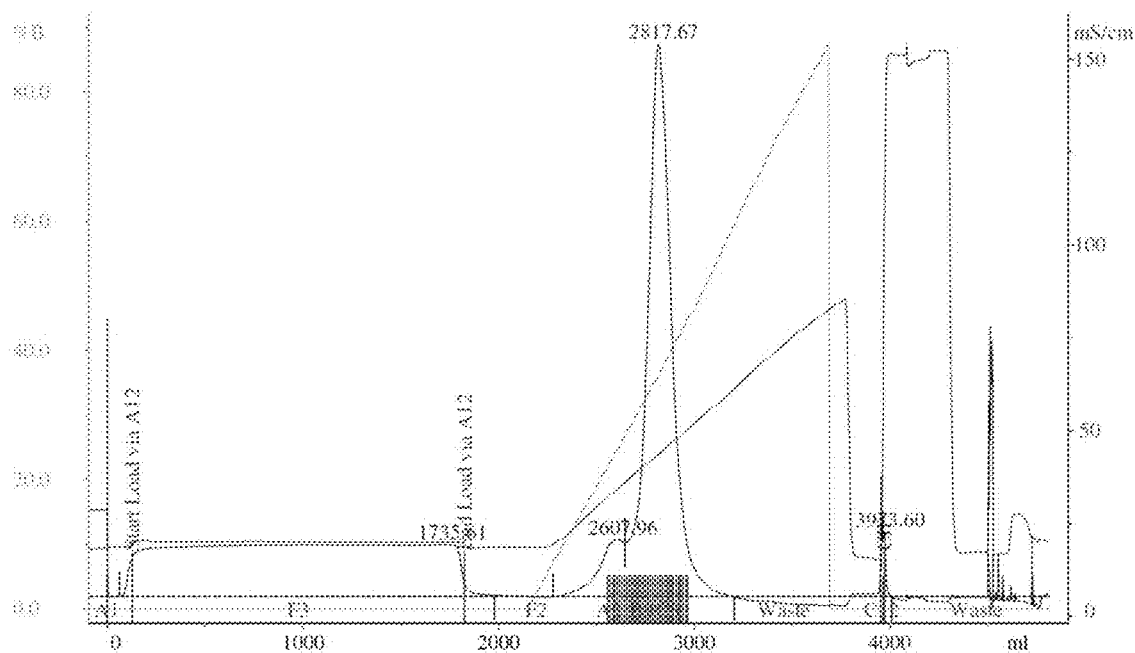
FIG. 2: Chromatogram of 114 mL SP Sepharose® FF column with NaCl elution gradient over 12.5 CV, followed by CIP. Load: 1.7 L of refolded pro-NGF mutein in 250 mM Arg, 10 mM iPO$_4$ pH 7.0; Buffer A: 250 mM Arg, 10 mM iPO$_4$ pH 7.0; Buffer B (salt elution) 1M NaCl, 250 mM Arg, 10 mM iPO$_4$ pH 7; CIP: 1M NaOH.
Figure 3:
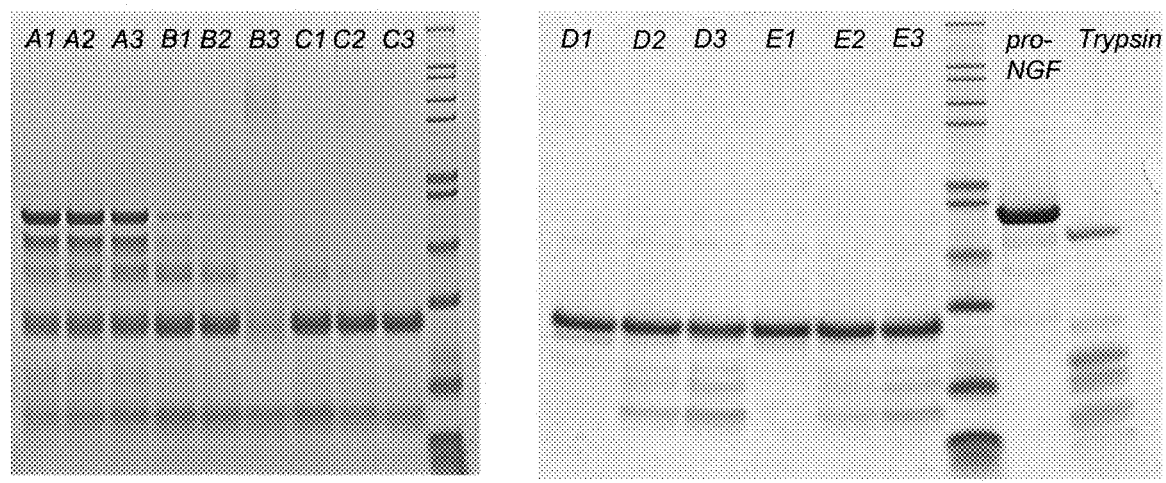
FIG. 3: Results of the first trypsinization screen. The italic codes (same codes in FIG. 3 and Table 7) denote abbreviations used for identification of the respective sample. The matrix conditions outlined in Table 7 were analyzed on a 12% SDS-PAGE operated with MES-buffer. Additionally, the utilized substrate (pro-NGF mutein) and trypsin were applied as controls. The molecular weight marker contains standard proteins of 200, 116, 97, 66, 55, 36, 31, 21, 14, 6 and 3 kDa size.
Figure 4A:
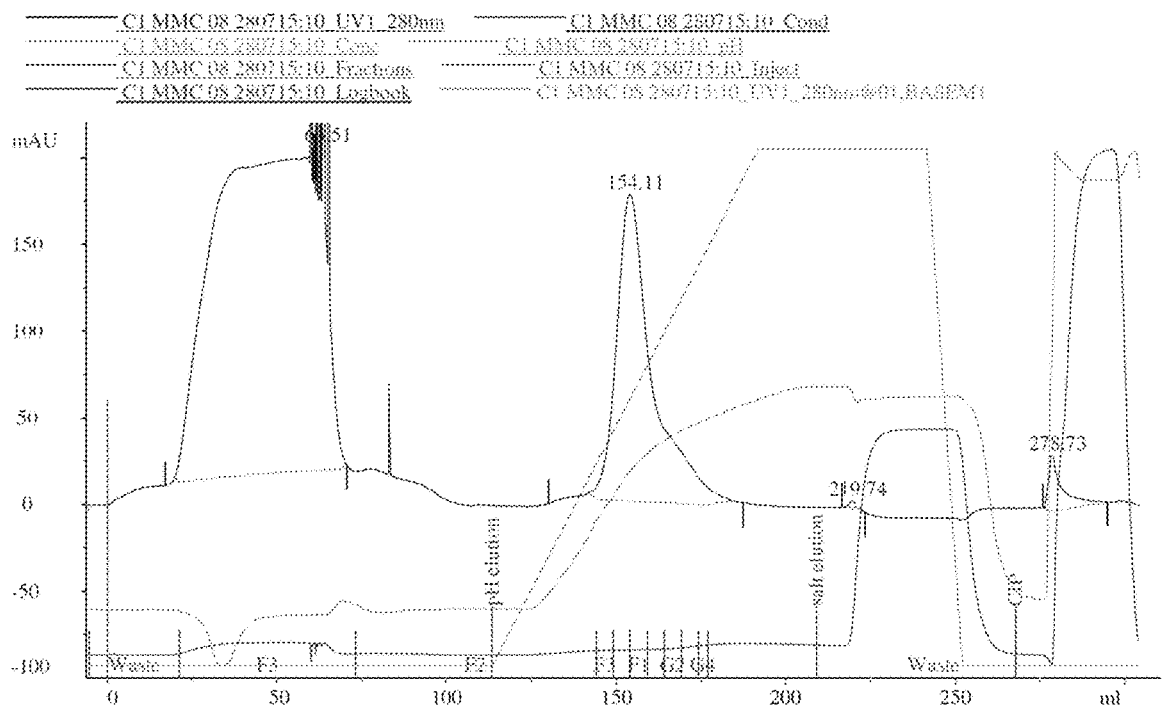
FIGS. 4A, 4B and 4C: Analytical chromatograms of different proteins
Figure 4B:
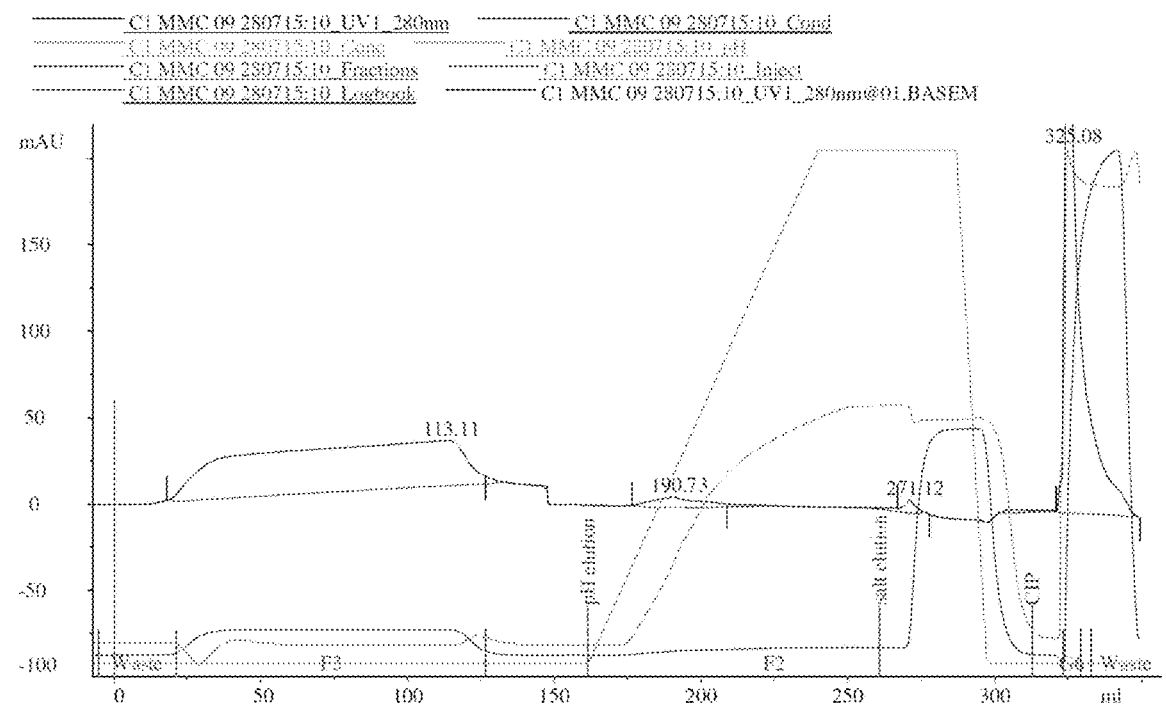
Figure 4C:
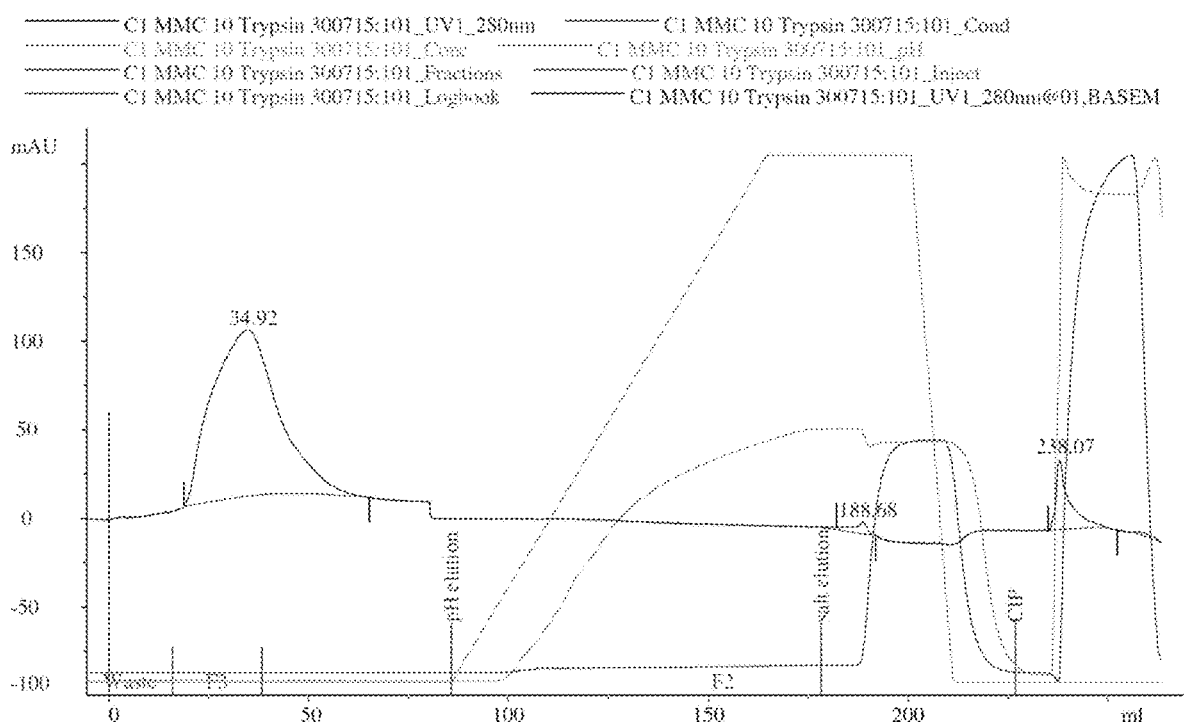
Figure 5A:
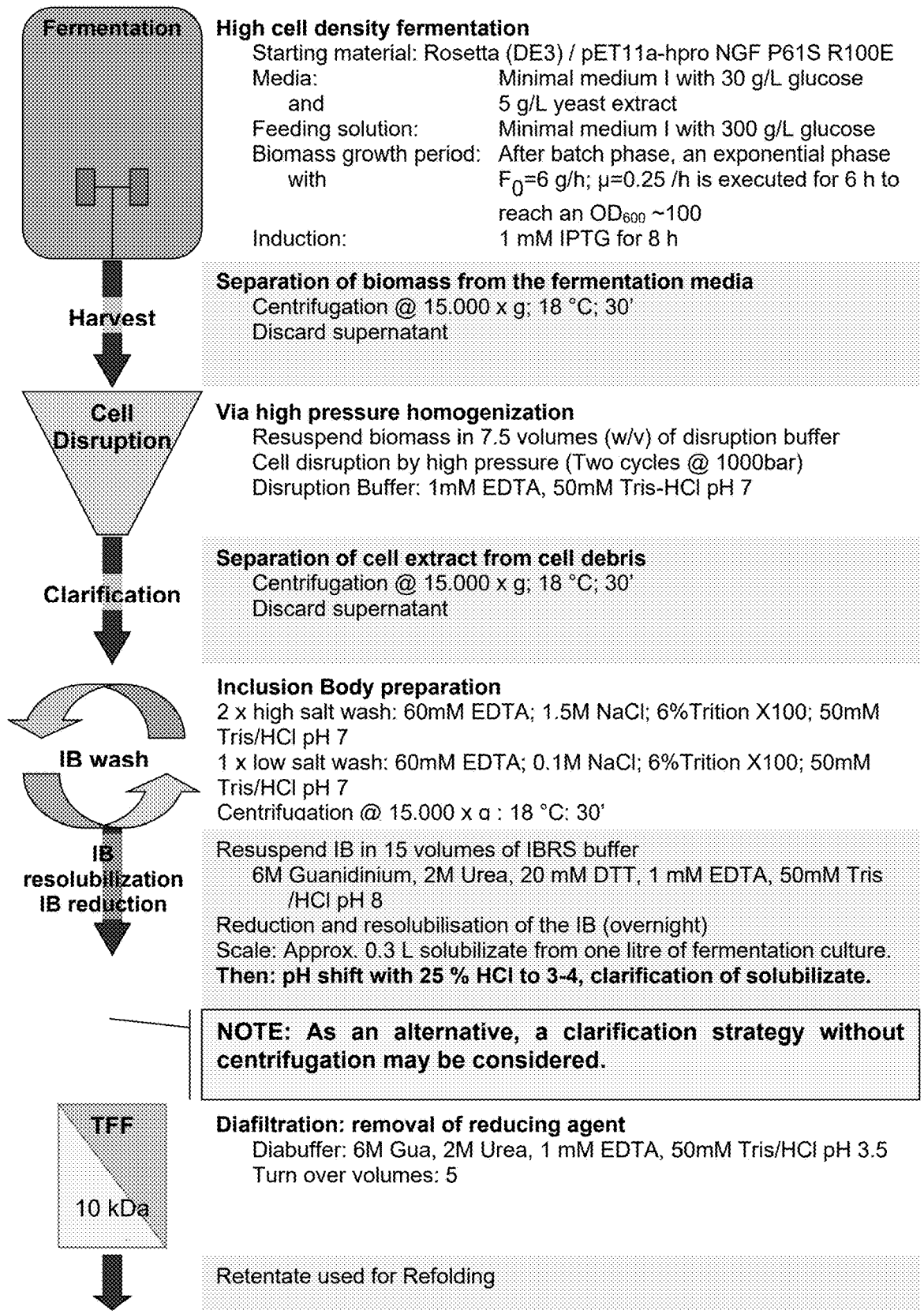
Figure 7:
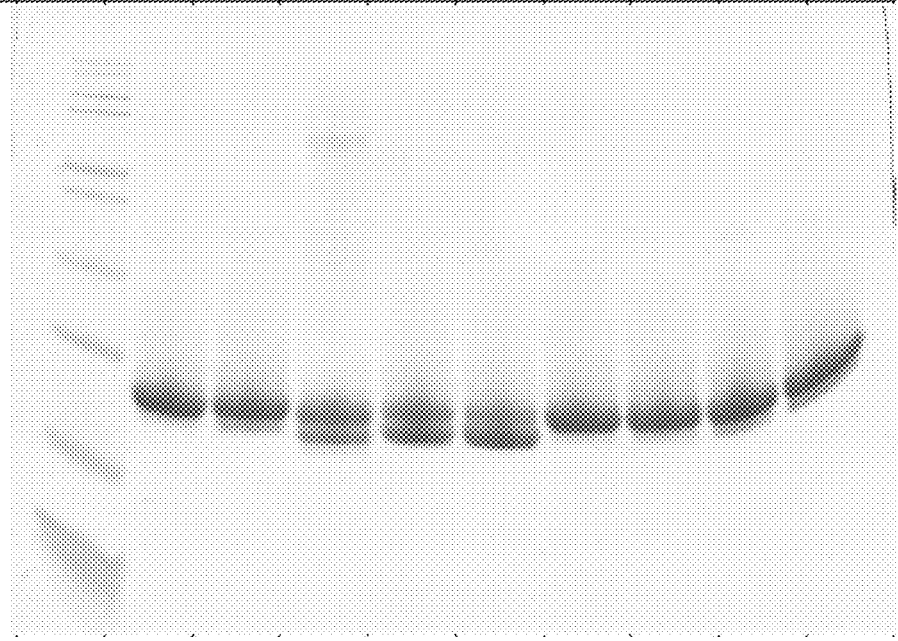
FIG. 7: Degradation of product stored at room temperature may reveal the presence of residual trypsin in the final product. Shown are two samples stored for 24 hours at room temperature (Lane 1) or in frozen condition (Lane 2), respectively.
Figure 8:
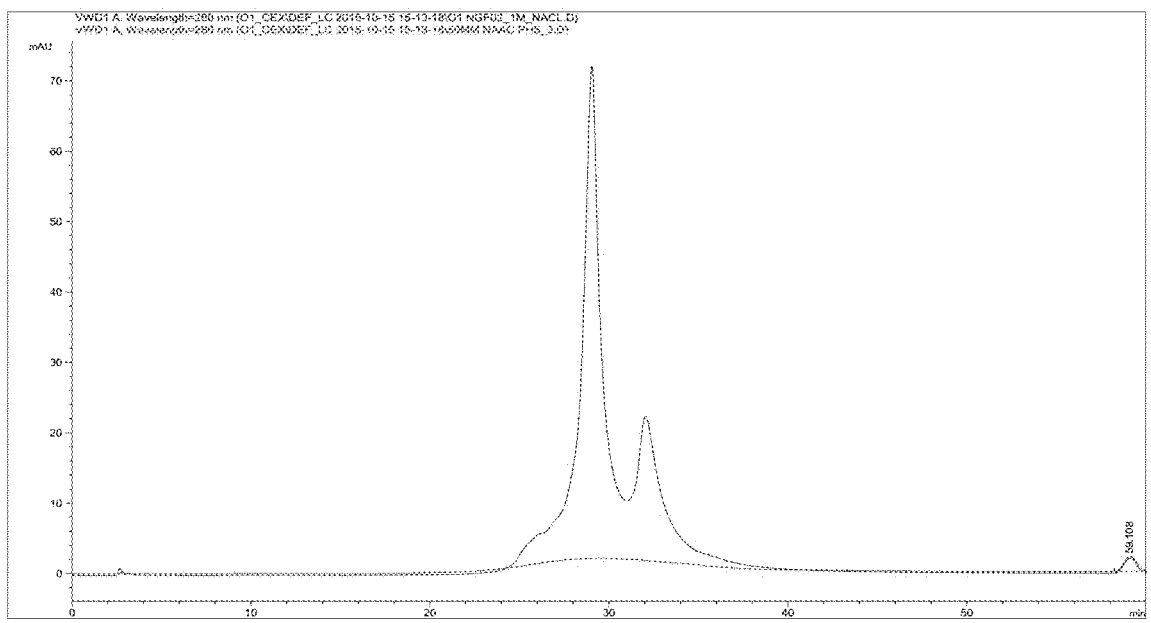
FIG. 8: Analytical CEX-HPLC of purified NGF mutein reveals the presence of charge isomers in the final product. The red line represents the blank chromatogram.
Figure 9A:
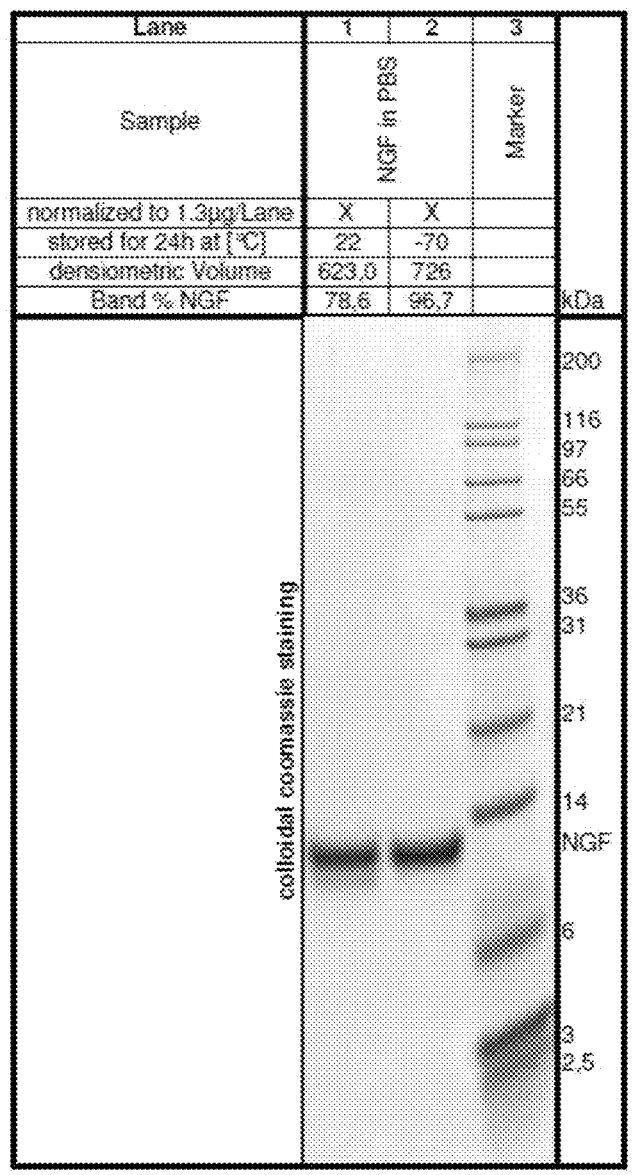
FIGS. 9A and 9B: Purity tests of NGF mutein
Figure 9B:
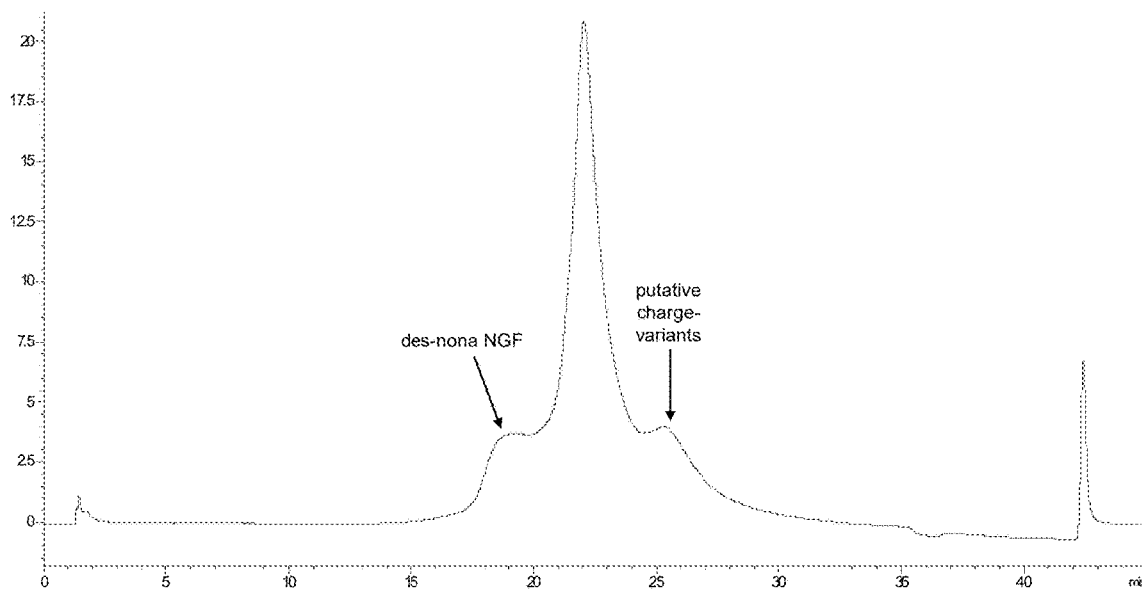
Figure 10:
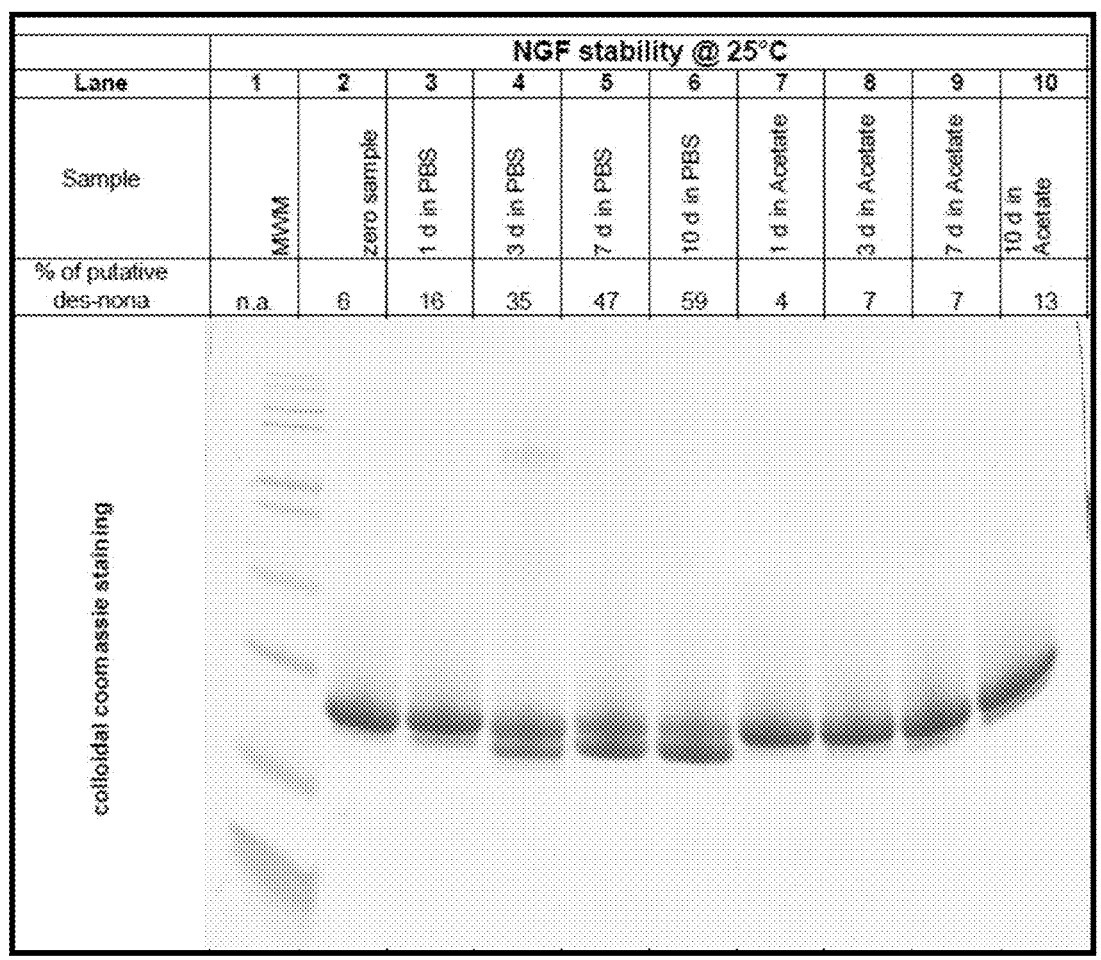
FIG. 10: Shown are two different formulations (PBS vs. 50 mM acetate buffer, pH 5.5) of the same NGF mutein preparation stored for seven days at 25° C. The acidic pH of the acetate formulation might suppress residual trypsin activity and therefore, could explain the higher product stability.
Figure 11:
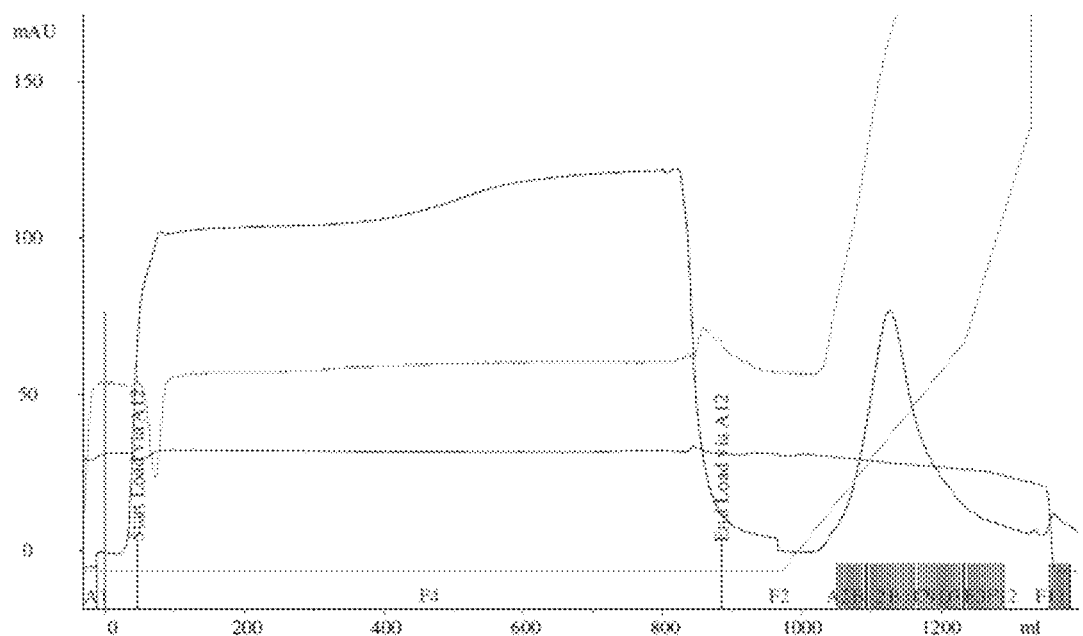
FIG. 11: Representative preparative chromatogram using Capto® MMC as capture column.
Figure 12A:
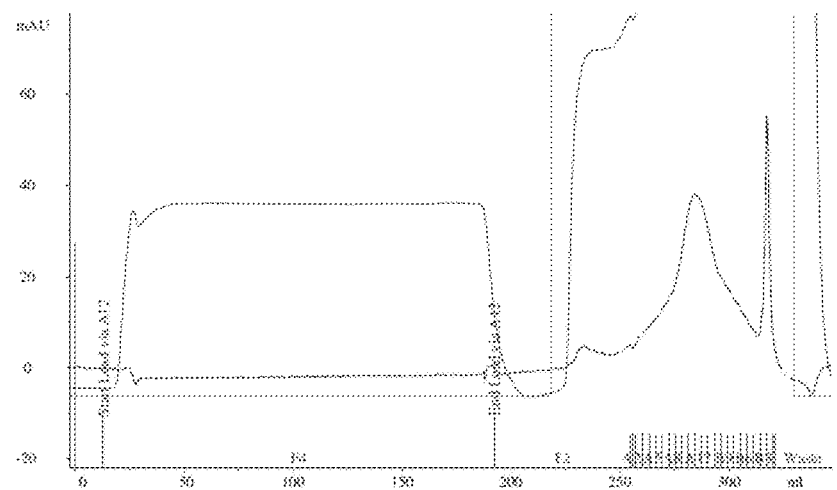
FIGS. 12A, 12B and 12C: Representative example for usage of SP Sepharose® HP as polishing column.
Figure 12B:
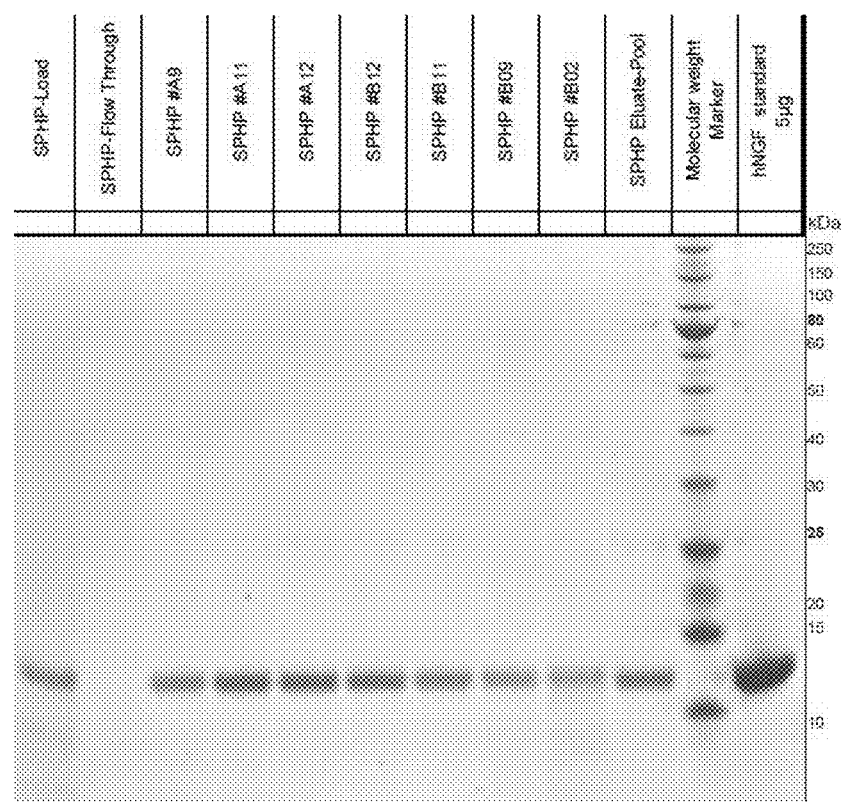
Figure 12C:
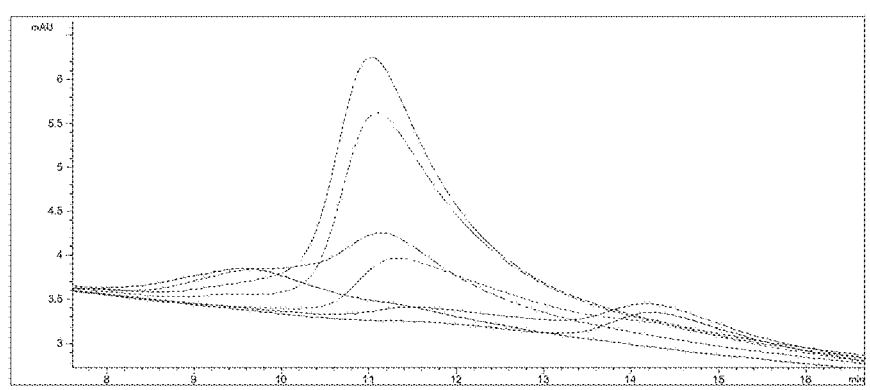
Figure 13:
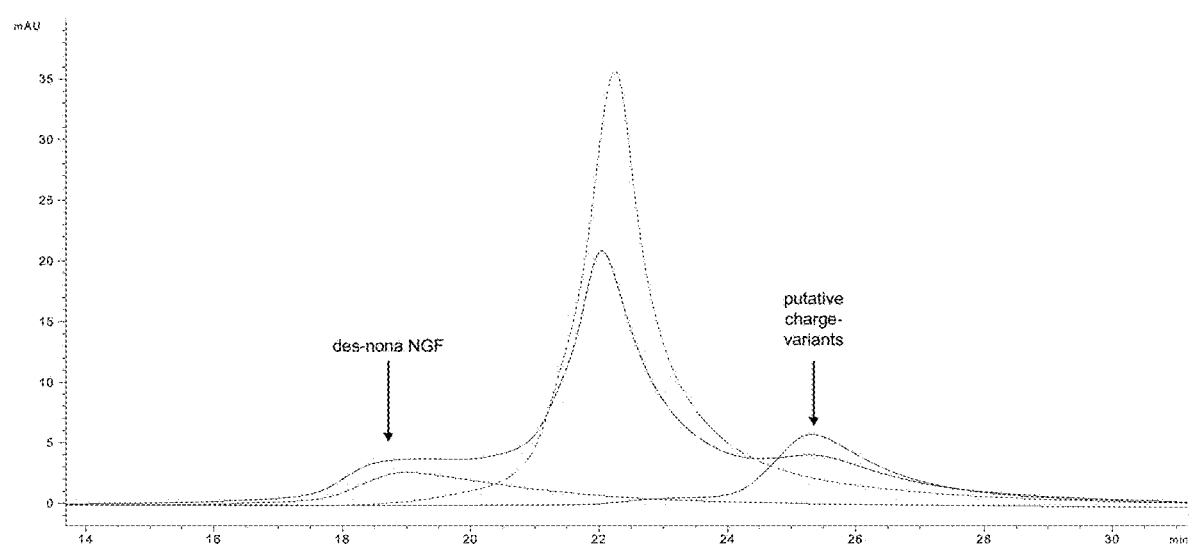
FIG. 13: CEX HPLC reveals the resolution of the described polishing column based on SP Sepharose® HP. The chromatogram with the second-highest peak at ca. 22 min represents the load onto this polishing column, while the three other chromatograms represent distinct elution fractions. On SDS-PAGE, the first eluting species is clearly identified as slightly truncated form of NGF, while the other fractions are characterized by the same migration behavior. Therefore, the latter eluting species is a putative charge variant of the main-product.
Figure 14A:
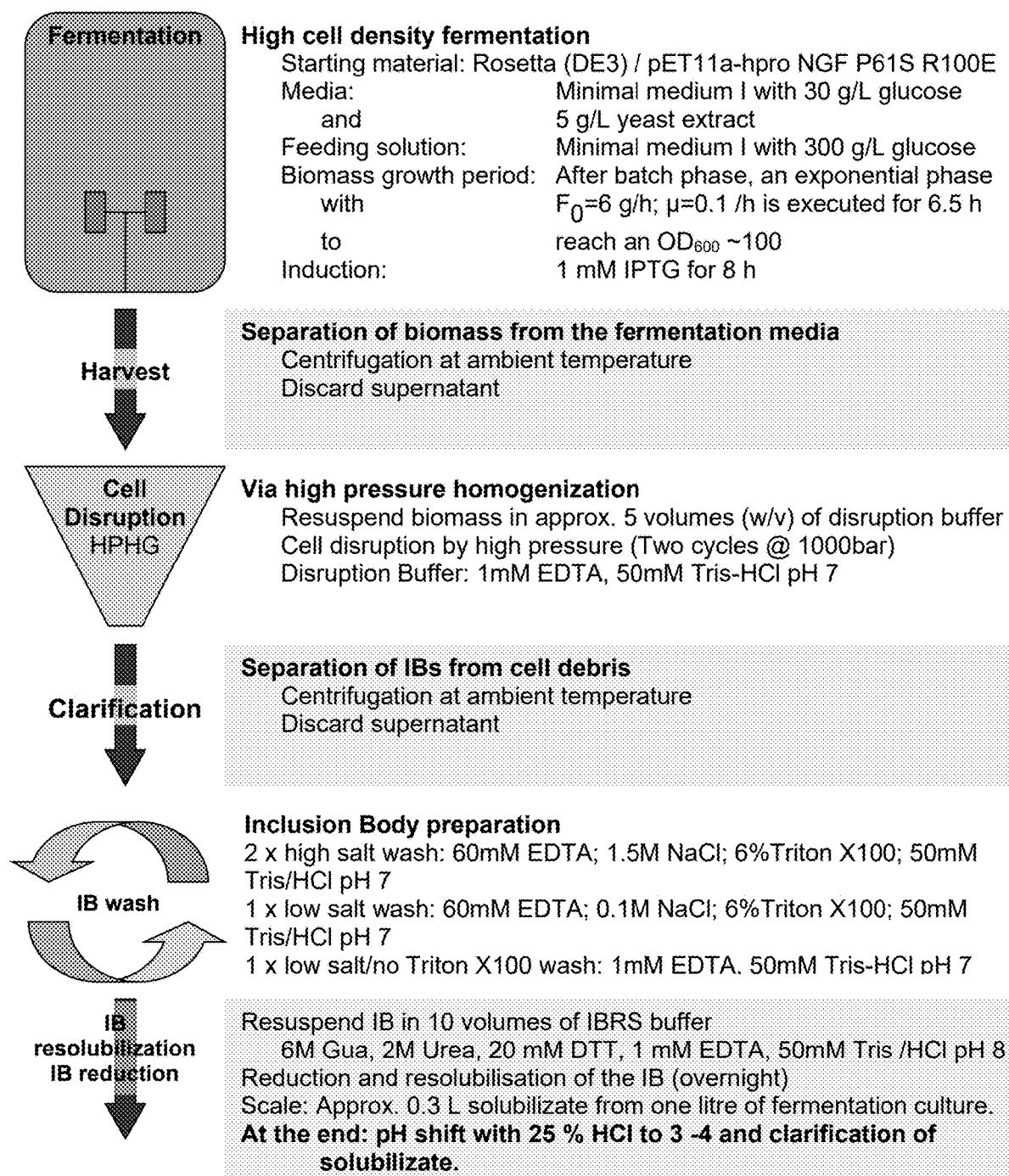
Figure 14D:
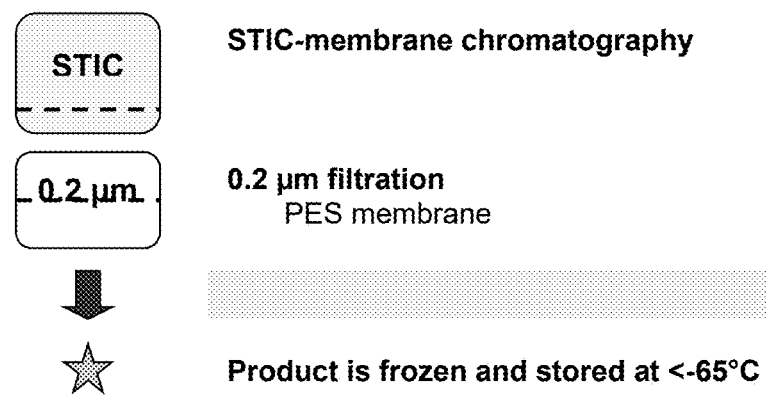

Pre-peptide: amino acid positions 1-18; pro-peptide: amino acid positions 19-121; mature NGF: amino acid positions 122-239; C-terminal dipeptide: amino acid positions 240-241.

Disulfide bonds (in the correctly folded mature part): linking amino acid positions 136↔201, 179↔229, 189↔231.

Furin cleavage site (RSKR): amino acid positions 118-121.

Asterisk (*) and cross (+) have the same meanings as in FIG. 15 C.

FIG. 15B: Schematic overview of pre-peptide, pro-peptide and mature NGF.

FIG. 15C: SEQ ID NO: 2: Sequence of mature human NGF.

Asterisk (*)=position 61 in mature human NGF; cross (+): position 100 in mature human NGF.

The invention claimed is:

1. A process for production of a mutein of nerve growth factor (NGF),
wherein the mutein is characterized by more than 90% sequence identity with SEQ ID NO: 2 and
the mutein comprises at least one mutation at any of positions 95-101 of SEQ ID NO: 2,
wherein the process comprises the following steps:
(a) obtaining a precursor of the mutein, wherein the precursor comprises a non-properly folded form,
(b) re-folding the non-properly folded form thereby producing a re-folded precursor of the mutein,
(c) proteolytically cleaving the re-folded precursor of the mutein to produce the mutein of NGF, wherein the proteolytic cleavage is prior to step (d), and
(d) purifying the mutein of NGF, wherein the purification comprises the following steps in order:
(d1) capturing comprising using mixed mode chromatography, and
(d2) polishing comprising using cation exchange chromatography.

2. The process according to claim 1, wherein the mutein is characterized by substitution of arginine in position 100.

3. The process according to any one of the preceding claims, wherein step (a) comprises recombinant expression of the precursor of the mutein in a host cell.

4. The process according to claim 1, wherein the precursor of the mutein is obtained in inclusion bodies.

5. The process according to claim 1, wherein the proteolytic cleavage comprises a protease selected from trypsin or furin.

6. The process according to claim 1, wherein the mixed mode chromatography comprises the use of a stationary phase having a charged group, and an aromatic group and/or a hydrophobic group.

7. The process according to claim 1, wherein the mutein comprises a substitution of the proline at position 61 of SEQ ID NO: 2 by another amino acid.

8. The process of claim 7, wherein the substitution of proline at position 61 of SEQ ID NO: 2 is a serine.

* * * * *

SEQUENCE LISTING

```
<160> NUMBER OF SEQ ID NOS: 4

<210> SEQ ID NO 1
<211> LENGTH: 241
<212> TYPE: PRT
<213> ORGANISM: Homo sapiens

<400> SEQUENCE: 1

Met Ser Met Leu Phe Tyr Thr Leu Ile Thr Ala Phe Leu Ile Gly Ile
1               5                   10                  15

Gln Ala Glu Pro His Ser Glu Ser Asn Val Pro Ala Gly His Thr Ile
                20                  25                  30

Pro Gln Ala His Trp Thr Lys Leu Gln His Ser Leu Asp Thr Ala Leu
            35                  40                  45

Arg Arg Ala Arg Ser Ala Pro Ala Ala Ile Ala Ala Arg Val Ala
    50                  55                  60

Gly Gln Thr Arg Asn Ile Thr Val Asp Pro Arg Leu Phe Lys Lys Arg
65                  70                  75                  80

Arg Leu Arg Ser Pro Arg Val Leu Phe Ser Thr Gln Pro Pro Arg Glu
                85                  90                  95

Ala Ala Asp Thr Gln Asp Leu Asp Phe Glu Val Gly Gly Ala Ala Pro
            100                 105                 110

Phe Asn Arg Thr His Arg Ser Lys Arg Ser Ser Ser His Pro Ile Phe
        115                 120                 125

His Arg Gly Glu Phe Ser Val Cys Asp Ser Val Ser Val Trp Val Gly
    130                 135                 140

Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
                165                 170                 175

Thr Lys Cys Arg Asp Pro Asn Pro Val Asp Ser Gly Cys Arg Gly Ile
            180                 185                 190

Asp Ser Lys His Trp Asn Ser Tyr Cys Thr Thr Thr His Thr Phe Val
```

```
              195                 200                 205
Lys Ala Leu Thr Met Asp Gly Lys Gln Ala Ala Trp Arg Phe Ile Arg
    210                 215                 220
Ile Asp Thr Ala Cys Val Cys Val Leu Ser Arg Lys Ala Val Arg Arg
225                 230                 235                 240
Ala

<210> SEQ ID NO 2
<211> LENGTH: 118
<212> TYPE: PRT
<213> ORGANISM: Homo sapiens

<400> SEQUENCE: 2

Ser Ser Ser His Pro Ile Phe His Arg Gly Glu Phe Ser Val Cys Asp
1               5                   10                  15
Ser Val Ser Val Trp Val Gly Asp Lys Thr Thr Ala Thr Asp Ile Lys
                20                  25                  30
Gly Lys Glu Val Met Val Leu Gly Glu Val Asn Ile Asn Asn Ser Val
            35                  40                  45
Phe Lys Gln Tyr Phe Phe Glu Thr Lys Cys Arg Asp Pro Asn Pro Val
        50                  55                  60
Asp Ser Gly Cys Arg Gly Ile Asp Ser Lys His Trp Asn Ser Tyr Cys
65                  70                  75                  80
Thr Thr Thr His Thr Phe Val Lys Ala Leu Thr Met Asp Gly Lys Gln
                85                  90                  95
Ala Ala Trp Arg Phe Ile Arg Ile Asp Thr Ala Cys Val Cys Val Leu
                100                 105                 110
Ser Arg Lys Ala Val Arg
        115

<210> SEQ ID NO 3
<211> LENGTH: 4
<212> TYPE: PRT
<213> ORGANISM: Homo sapiens

<400> SEQUENCE: 3

Arg Ser Lys Arg
1

<210> SEQ ID NO 4
<211> LENGTH: 4
<212> TYPE: PRT
<213> ORGANISM: Artificial Sequence
<220> FEATURE:
<223> OTHER INFORMATION: Cleavage site

<400> SEQUENCE: 4

Val Ser Ala Arg
1
```